United States Patent
Lv et al.

(10) Patent No.: US 12,410,124 B2
(45) Date of Patent: Sep. 9, 2025

(54) CARBAMATE-SUBSTITUTED STYRYL SULFONE COMPOUNDS, PREPARATION METHOD AND USE THEREOF

(71) Applicant: HUAXIASHENGSHENG PHARMACEUTICAL BEIJING CO., LTD., Bejing (CN)

(72) Inventors: Xinan Lv, Beijing (CN); Junyi Liu, Beijing (CN); Shouxin Zhou, Beijing (CN); Xiang Ao, Beijing (CN); Zhizhong Ma, Beijing (CN)

(73) Assignee: Huaxiashengsheng Pharmaceutical Beijing Co., Ltd., Beijing (CN)

( * ) Notice: Subject to any disclaimer, the term of this patent is extended or adjusted under 35 U.S.C. 154(b) by 862 days.

(21) Appl. No.: 17/628,017

(22) PCT Filed: Jul. 18, 2019

(86) PCT No.: PCT/CN2019/096502
§ 371 (c)(1),
(2) Date: Jan. 18, 2022

(87) PCT Pub. No.: WO2021/007840
PCT Pub. Date: Jan. 21, 2021

(65) Prior Publication Data
US 2022/0267263 A1 Aug. 25, 2022

(51) Int. Cl.
*C07C 317/28* (2006.01)
*C07D 207/08* (2006.01)
*C07D 213/643* (2006.01)
*C07D 265/30* (2006.01)
*C07D 307/54* (2006.01)
*C07D 333/36* (2006.01)

(52) U.S. Cl.
CPC .......... *C07C 317/28* (2013.01); *C07D 207/08* (2013.01); *C07D 213/643* (2013.01); *C07D 265/30* (2013.01); *C07D 307/54* (2013.01); *C07D 333/36* (2013.01)

(58) Field of Classification Search
None
See application file for complete search history.

(56) References Cited

FOREIGN PATENT DOCUMENTS

| CN | 103936637 A | 7/2014 |
|---|---|---|
| CN | 104230770 A | 12/2014 |
| CN | 104230770 B | 11/2017 |
| WO | WO 2001/026645 A1 | 4/2001 |
| WO | WO 2002/069892 A2 | 9/2002 |
| WO | WO 2006/025924 A1 | 3/2006 |

OTHER PUBLICATIONS

Ning et al., Journal of Enzyme Inhibition and Medicinal Chemistry (2016), 31:3, pp. 464-469.*
Office Action issued in Chinese Application No. 201980098207.8, dated Feb. 22, 2023.
Chun, H., "Carbonate Derivatives", Organic Chemistry, China Medical Science and Technology Press, Jul. 31, 2013, pp. 359-360.
Yousheng, C., "Preparation of Amides", "Organic Synthesis", Jiangxi Science and Technology Press, May 31, 2018, p. 49.
International Search Report and Written Opinion issued in International Application No. PCT/CN2019/096502, mailed on Apr. 20, 2020.

* cited by examiner

*Primary Examiner* — Brian J Davis
(74) *Attorney, Agent, or Firm* — Knobbe, Martens, Olson & Bear, LLP

(57) ABSTRACT

Carbamate-substituted styryl sulfone compounds have a structure of general formula (I). The compounds not only has a significantly enhanced acetylcholinesterase inhibitory activity compared with carbamates as positive drugs, but also has a significantly enhanced therapeutic effect on Parkinson's disease compared with caffeic acid phenethyl ester compounds having similar structures.

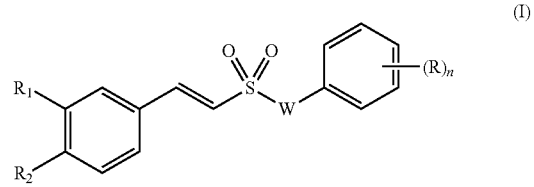

17 Claims, No Drawings

CARBAMATE-SUBSTITUTED STYRYL SULFONE COMPOUNDS, PREPARATION METHOD AND USE THEREOF

TECHNICAL FIELD

The invention falls into the technical field of pharmacochemistry, and specifically relates to carbamate-substituted styryl sulfone compounds, preparation method and use thereof.

BACKGROUND

Parkinson's disease is a common clinical degenerative disease of the central nervous system. It mainly occurs in middle-aged and elderly people aged 65 years or older, and the incidence rate shows a trend of increasing year by year with age. The prevalence among people aged 65 years or older in China is about 1.7%. Parkinson's disease is caused by a variety of factors. Current researches believe that its risk factors include age factor, genetic factor, environmental factor, etc. The pathogenesis is mainly related to cerebrospinal fluid biology, p38 pathway, oxidative stress, immune inflammation, and abnormal neural pathways, etc.

In terms of cerebrospinal fluid biology, the selectively phosphorylated alpha-synuclein (p-α-s) in the cerebrospinal fluid of the patients with Parkinson's disease is much higher than that of the patients without Parkinson's disease. A lot of studies have found that p-α-s is involved in the formation of Lewy body which serves as one of the main pathological features of Parkinson's disease. Studies have also found that the content of the tyrosine hydroxylase (TH) as the marker of the dopaminergic neuron in the mouse model of Parkinson's disease is significantly lower than that in the normal control group.

The main mechanism leading to Parkinson's disease is the apoptosis of dopamine neurocytes in the substantia nigra. The p38 mitogen-activated protein kinase (p38 MAPK) is a potent effector of neurocyte apoptosis caused by various stimuli. The p38 MAPK is inactive in the dephosphorylated state. When the cells are subjected to various stimuli, MKK3 and MKK6 genes can rapidly mediate the phosphorylation of p38 MAPK to form pp38, so as to trigger inflammatory reaction, cell differentiation, cell cycle arrest, and cell apoptosis through a variety of pathways and regulatory manners. The postmortem autopsies of patients with Parkinson's disease have found pp38 in the brain tissue, and the active form of pp38 is also found in animal models and cell models of Parkinson's disease. More and more evidences suggest that pp38 is involved in the progression of Parkinson's disease mainly through the neuroinflammative reaction and the induction of neuron apoptosis.

The oxidative stress theory occupies an important position in the study on the mechanism of Parkinson's disease. It can provide a good explanation for the delayed and accumulated nerve damage. Oxidative stress refers to the case that highly active molecules such as reactive oxygen free radicals and reactive nitrogen free radicals are excessively produced in the body when the body is subjected to various harmful stimuli, so that the oxidation level exceeds the removal of oxides and the oxidation and anti-oxidation systems are out of balance, thereby resulting in tissue damage. The postmortem autopsies of patients with Parkinson's disease have found that some markers for oxidative damage in the substantia nigra are significantly increased, while the level of reduced glutathione having an antioxidant effect is decreased by 30-60%. The phase II detoxifying enzyme is an endogenous protective protein that plays a protective role by catalyzing the conversion of free radicals into non-toxic products and increasing their water solubility to facilitate the elimination of free radicals. The phase II detoxifying enzyme includes heme oxygenase-1 (HO-1), glutamate cysteine ligase catalytic subunit (GCLC), etc. A plenty of studies have shown that they have a neuroprotective effect in Parkinson's disease.

The neuroinflammation is a double-edged sword. On one hand, under normal circumstances, microglial cells and astrocytes maintain the homeostasis in the normal tissues of the central nervous system. On the other hand, when they overproduce inflammatory factors, these inflammatory factors amplify their respective toxicities, and ultimately lead to the damage, degeneration, and even death of neurons. The microglial cells are the main in situ immune cells that implement defense responses in the brain. The activated microglial cells express different surface antigens such as CD11b. The activated microglial cells can damage dopaminergic neurons through a variety of ways. The astrocytes are the largest glial cells with the largest number and widest distribution in the central nervous system. Their specific marker is glial fibrillary acidic protein (GFAP). The activated astrocytes can also damage the dopaminergic neurons through a variety of ways.

Most studies believe that Parkinson's disease is a typical neurodegenerative disease caused by chemical neurotransmitter abnormalities, and the main pathological feature is the reduction of dopaminergic neurons in the substantia nigrastriatum system. The activity of choline transferase decreases in the cortex such as frontal lobe, temporal lobe, parietal lobe, and right hippocampus of patients with Parkinson's disease, and cholinergic neuron damage may be the main biochemical mechanism of cognitive dysfunction and dementia in Parkinson's disease. Many studies have shown that cholinesterase inhibitors, especially acetylcholinesterase inhibitors, are beneficial to improve the prognosis of dementia patient with Parkinson's disease and enhance the cognitive function. Rivastigmine is a carbamate drug that exerts pharmacological effects through reversibly inhibiting the hydrolysis of acetylcholine by acetylcholinesterase. It has been approved for treating mild to moderate dementia related to Parkinson's disease.

Due to the complex and diverse pathogenesis, current therapeutic drugs mainly focus on a single target, and it is necessary to select appropriate drugs in the early stage of the disease according to the symptoms of the patient for therapy alone or in combination. Common drugs include dopamine drugs (levodopa, carbidopa), dopamine receptor agonists (cabergoline, pramipexole), dopamine retention agents (selegiline, entacapone), anticholinergic drugs (benzhexol hydrochloride), and other drugs (amantadine), and some drugs are still in clinical trials, such as anti-inflammatory agents (minocycline, pioglitazone), antioxidants (coenzyme Q10, edaravone), cholinesterase inhibitors (donepezil, rivastigmine), excitatory amino acid receptor antagonists (memantine), etc. Many of these drugs are only used to improve the complications of Parkinson's disease, such as dementia. For Parkinson's disease itself or in the middle and advanced stages of Parkinson's disease, the symptom controlling effects of existing therapeutic drugs are often limited, and there is still a strong clinical demand for new therapeutic drugs. Therefore, it has important social significances and economic values to develop an efficient and multi-targeted drug for the treatment or prevention of Parkinson's disease.

The styryl sulfone compounds obtained from the modifications based on the natural product caffeic acid phenethyl ester is a kind of compounds with multi-targeted neuroprotective activity. On the basis of caffeic acid phenethyl ester, the stability in vivo is enhanced and the ability to penetrate the blood-brain barrier is improved, while the anti-oxidative activity, anti-inflammatory effect, inhibitory effect on excitotoxic damage and the like are maintained or enhanced. Some compounds, their preparation methods, and biological activities are described in the patent CN104230770B. This patent does not provide targeted verifications on the therapeutic effects of related compounds on Parkinson's disease. It is only speculated from the anti-oxidative activity test results and membrane permeability evaluation results to potentially have therapeutic effects on a variety of neurodegenerative diseases including Parkinson's disease. The cholinesterase inhibitors are a class of drugs that can bind to cholinesterase and inhibit the activity of cholinesterase. Their functions are to accumulate the acetylcholine released from cholinergic nerve endings, which shows enhanced M-like and N-like effects to have a function of exciting cholinergic receptors, so such a class of drugs is also called as cholinomimetic drugs. It can be divided into two categories: the first category involves readily reversible or transient cholinesterase inhibitors, such as rivastigmine, neostigmine, physostigmine, etc., whose common feature lies in the existence of carbamate functional group; and the second category involves hardly irreversible or irreversible cholinesterase inhibitors, such as organophosphates, including agricultural pesticides and chemical war gases, which have strong toxicities to the human body so that it is difficult to be developed into drugs. On one hand, these compounds can inhibit the hydrolysis of acetylcholine by acetylcholinesterase, increase the concentration of acetylcholine, and protect cholinergic neurons, thereby improving the dementia symptoms related to Parkinson's disease; and on the other hand, it has been proven that the long-term exposures to a variety of carbamate compounds may increase the probability of Parkinson's disease. Even for FDA-approved rivastigmine, the most common adverse reactions also include tremor (incidence rate exceeding 5%). In addition, compared with the control group, there are various degenerative adverse reactions such as deterioration of Parkinson's disease and hypokinesia or dyskinesia.

SUMMARY

The technical problem to be solved by the invention is to introduce carbamate functional groups on the basis of styryl sulfone compounds with neuroprotective activity, thereby obtaining a new type of compound that can be used to treat and/or prevent Parkinson's disease, and provide the preparation method and use in preparing medicaments for treating and/or preventing Parkinson's disease. The original design aim of the invention is to introduce the inhibitory activity of the carbamate functional group on acetylcholinesterase, without affecting the multi-targeted neuroprotective activity of caffeic acid phenethyl ester compound as much as possible, so as to obtain a new drug both delaying the progression in the course of Parkinson's disease and improving the dementia symptoms of Parkinson's disease. Through the test results, we surprisingly find that the target compound not only has a significantly enhanced inhibitory activity on acetylcholinesterase as compared with carbamate-type positive drugs, but also has a significantly enhanced therapeutic effect on Parkinson's disease as compared with caffeic acid phenethyl ester compounds with similar structures. According to the published prior art, this discovery is not predictable. The invention solves above technical problem through the following technical solutions.

In one aspect, the invention provides a compound of general formula I or pharmaceutically acceptable salts thereof:

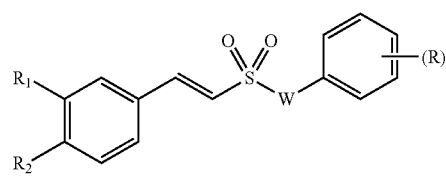

I wherein, at least one of $R_1$ and $R_2$ is independently selected from: carbamoyloxy unsubstituted or substituted by one or two $R_3$;

the other one of $R_1$ and $R_2$ is independently selected from: carbamoyloxy unsubstituted or substituted by one or two $R_3$, $C_{1-6}$ alkoxy unsubstituted or substituted by one to six halogen, $—N(R_4)_2$ or $—OR_5$, $C_{1-6}$ alkylacyloxy or $C_{7-10}$ arylacyloxy unsubstituted or substituted by one to six halogen, $—N(R_4)_2$ or $—OR_5$, sulfonyloxy substituted by $C_{1-3}$ alkyl or $C_{6-8}$ aryl, $—OSi(R_6)_3$, and $—OH$;

W is $C_{1-6}$ alkylene or $C_{2-6}$ alkenylene unsubstituted or substituted by one to three halogen, nitro, $C_{1-6}$ alkyl, $—N(R_4)_2$ or $—OR_5$;

each R is independently selected from halogen, nitro, $—OR_7$, $—N(R_4)_2$, and $C_{1-6}$ alkyl, $C_{6-10}$ aryl or $C_{5-9}$ heteroaryl, unsubstituted or substituted by one to six halogen, nitro, $—N(R_4)_2$ or $—OR_5$;

n is an integer from 0 to 5;

wherein, each $R_3$ is independently selected from: $C_{1-6}$ saturated alkyl, $C_{2-4}$ alkenyl, $C_{2-4}$ alkynyl, $C_{6-10}$ aryl, $C_{5-9}$ heteroaryl, $C_{1-6}$ alkylacyl or $C_{7-10}$ arylacyl, unsubstituted or substituted by one to six halogen, nitro, $—N(R_4)_2$ or $—OR_5$; sulfonyl substituted by $C_{1-3}$ alkyl or $C_{6-8}$ aryl; or two $R_3$ together with the nitrogen atom to which they are attached form a 5- to 7-membered nitrogen-containing saturated heterocyclyl (for example, 1-pyrrolidinyl, 1-piperidyl, 4-morpholinyl or 1-piperazinyl) unsubstituted or substituted by one or two $R_6$;

each $R_4$ is independently —H or $C_{1-6}$ saturated alkyl;

each $R_5$ is independently selected from —H, $C_{1-6}$ saturated alkyl, $C_{2-4}$ alkenyl, $C_{6-10}$ aryl, and $C_{5-9}$ heteroaryl;

each $R_6$ is independently selected from $C_{1-6}$ alkyl, $C_{1-6}$ alkoxy and $C_{6-8}$ aryl, unsubstituted or substituted by one to six halogen;

each $R_7$ is independently selected from H; $C_{1-6}$ saturated alkyl, $C_{2-4}$ alkenyl, $C_{2-4}$ alkynyl, $C_{6-10}$ aryl, $C_{5-9}$ heteroaryl, $C_{1-6}$ alkylacyl or $C_{7-10}$ arylacyl, unsubstituted or substituted by one to six halogen, $N(R_4)_2$ or $OR_5$; sulfonyl substituted by $C_{1-3}$ alkyl or $C_{6-8}$ aryl; and $Si(R_6)_3$.

Preferably, at least one of $R_1$ and $R_2$ is independently selected from carbamoyloxy unsubstituted or substituted by one or two $R_3$; the other one of $R_1$ and $R_2$ is independently selected from: carbamoyloxy unsubstituted or substituted by one or two $R_3$, $C_{1-6}$ alkoxy unsubstituted or substituted by one to six halogen or $OR_5$, $C_{1-6}$ alkylacyloxy unsubstituted or substituted by $—N(R_4)_2$ or $—OR_5$, sulfonyloxy substituted by $C_{1-3}$ alkyl or $C_{6-8}$ aryl, and $—OSi(R_6)_3$;

More preferably, at least one of $R_1$ and $R_2$ is independently selected from carbamoyloxy, N-methylcarbamoyloxy, N,N-dimethylcarbamoyloxy, N,N-diethylcarbamoyloxy, N-methyl-N-ethylcarbamoyloxy, N-methyl-N-(2- methoxyethyl)carbamoyloxy, N-(5-methyl-2-nitroanilino)carbamoyloxy, N-(2-methyl-5-nitroanilino)carbamoyloxy, N-(p-methoxyphenyl)carbamoyloxy, N-(p-methylaminophenyl)carbamoyloxy, N-methyl-N-phenylcarbamoyloxy, N-methyl-N-p-chlorophenylcarbamoyloxy, N-methyl-N-p-bromophenylcarbamoyloxy, N-methyl-N-p-iodophenylcarbamoyloxy, N-thienylcarbamoyloxy, N-furylcarbamoyloxy, N-methyl-N-mesylcarbamoyloxy, and N-methyl-N-p-tosylcarbamoyloxy.

The other one of $R_1$ and $R_2$ is independently selected from carbamoyloxy, N-methylcarbamoyloxy, N,N-dimethylcarbamoyloxy, N,N-diethylcarbamoyloxy, N-methyl-N-ethylcarbamoyloxy, N-methyl-N-(2-methoxyethyl)carbamoyloxy, N-(5-methyl-2-nitroanilino)carbamoyloxy, N-(2-methyl-5-nitroanilino)carbamoyloxy, N-(p-methoxyphenyl)carbamoyloxy, N-(p-methylaminophenyl)carbamoyloxy, N-methyl-N-phenylcarbamoyloxy, N-methyl-N-p-chlorophenylcarbamoyloxy, N-methyl-N-p-bromophenylcarbamoyloxy, N-methyl-N-p-iodophenylcarbamoyloxy, N-thienylcarbamoyloxy, N-furylcarbamoyloxy, N-methyl-N-mesylcarbamoyloxy, and N-methyl-N-p-tosylcarbamoyloxy, or selected from methoxy, ethoxy, t-butoxy, trifluoromethoxy, 2,3-dibromobutoxy, 2-methoxyethoxy, 2-benzyloxyethoxy, acetyloxy, propionyloxy, pivaloyloxy, methoxyacetyloxy, 4-methoxybutyryloxy, 3-aminopropionyloxy, 2-aminopropionyloxy, mesyloxy, ethylsulfonyloxy, p-tosyloxy, trimethylsiloxy, triphenylsiloxy, chloromethyl(dimethyl)siloxy, and dimethoxy(phenyl)siloxy;

Preferably, W is $C_{1-6}$ alkylene or $C_{2-6}$ alkenylene unsubstituted or substituted by one or two halogen, nitro, $C_{1-6}$ alkyl or $—OR_5$;

More preferably, W is selected from $—CH_2—$, $—CH_2CH_2—$, $—CH_2CH_2CH_2—$, $—CH(F)—$, $—CH(Cl)—$, $—CH(Br)—$, $—CF_2—$, $—CH(Cl)CH_2—$, $—CH_2CH(Cl)—$, $—CH(Cl)CH(Cl)—$, $—CH_2CH(Cl)CH_2—$, $—CH(NO_2)—$, $—CH_2CH(NO_2)—$, $—CH_2CH(NO_2)CH_2—$, $—CH(CH_3)—$, $—CH(CH_3)CH_2—$, $—CH(OCH_3)—$, $—CH_2CH(OCH_2CH_3)CH(OCH_2CH_3)—$, $—CH_2CH(OCH_2C_6H_5)CH_2—$, $—CH_2CH(OH)—$, $—CH=CH—$, $—CH_2CH=CHCH_2—$, $—CH=CHCH_2—$, $—CH=C(CH_3)—$, and $—CH(Cl)CH=CHCH_2—$;

Preferably, each R is independently selected from halogen, nitro, $—OR_7$, $—N(R_4)_2$, and $C_{1-6}$ alkyl or $C_{6-10}$ aryl unsubstituted or substituted by one to six halogen, nitro or $—OR_5$;

More preferably, each R is independently selected from fluoro, chloro, bromo, iodo, nitro, hydroxy, methoxy, ethoxy, isopropoxy, t-butoxy, 2,2,2-trifluoroethoxy, 2-methylaminoethoxy, N,N-dimethylaminomethoxy, allyloxy, phenoxy, benzyloxy, p-methylaminobenzyloxy, 3,4-dimethoxybenzyloxy, formyloxy, acetyloxy, dimethylaminoacetyloxy, benzoyloxy, phenylacetyloxy, p-methoxyphenylacetyloxy, trimethylsiloxy, triphenylsiloxy, chloromethyl(dimethyl)siloxy, dimethoxy(phenyl)siloxy, amino, methylamino, ethylamino, diisopropylamino, methyl, ethyl, isopropyl, t-butyl, trifluoromethyl, phenyl, benzyl, phenethyl, p-chlorophenyl, p-nitrophenyl, and 3,4-dimethoxyphenyl;

Preferably, n is an integer from 0 to 3;

Preferably, each $R_3$ is independently selected from: $C_{1-6}$ saturated alkyl, $C_{6-10}$ aryl or $C_{5-9}$ heteroaryl, unsubstituted or substituted by one to six halogen, nitro, $—N(R_4)_2$ or $—OR_5$; and sulfonyl substituted by $C_{1-3}$ alkyl or $C_{6-8}$ aryl;

Preferably, in a specific embodiment, at least one of $R_1$ and $R_2$ is independently selected from carbamoyloxy unsubstituted or substituted by one or two $R_3$; the other one of $R_1$ and $R_2$ is independently selected from: carbamoyloxy unsubstituted or substituted by one or two $R_3$, $C_{1-6}$ alkoxy unsubstituted or substituted by one to six halogen or $OR_5$, $C_{1-6}$ alkylacyloxy unsubstituted or substituted by $—N(R_4)_2$ or $—OR_5$, sulfonyloxy substituted by $C_{1-3}$ alkyl or $C_{6-8}$ aryl, and $—OSi(R_6)_3$;

W is $C_{1-6}$ alkylene or $C_{2-6}$ alkenylene unsubstituted or substituted by one or two halogen, nitro, $C_{1-6}$ alkyl or $—OR_5$;

each R is independently selected from halogen, nitro, $—OR_7$, $—N(R_4)_2$, and $C_{1-6}$ alkyl or $C_{6-10}$ aryl unsubstituted or substituted by one to six halogen, nitro or $—OR_5$;

n is an integer from 0 to 3;

wherein each $R_3$ is independently selected from: $C_{1-6}$ saturated alkyl, $C_{6-10}$ aryl or $C_{5-9}$ heteroaryl, unsubstituted or substituted by one to six halogen, nitro, $—N(R_4)_2$ or $—OR_5$; and sulfonyl substituted by $C_{1-3}$ alkyl or $C_{6-8}$ aryl.

In a more specific embodiment, the compound of general formula I is selected from the following compounds:

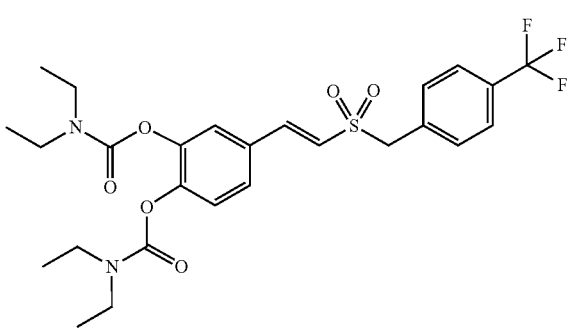

Compound B1-1

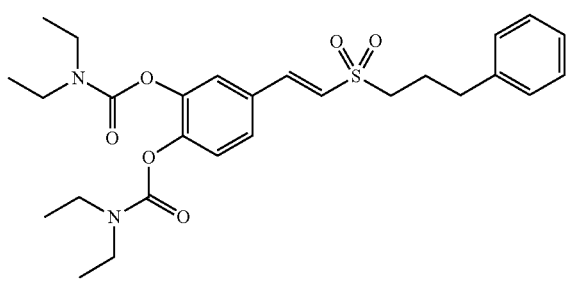

Compound C1-1

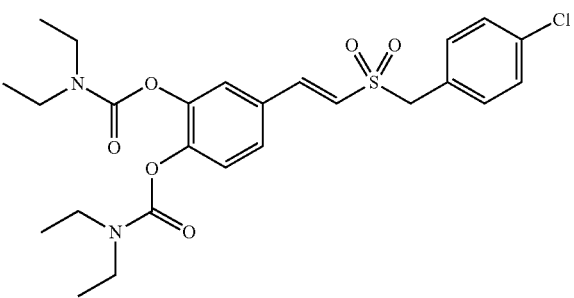

Compound D1-1

Compound G1-1
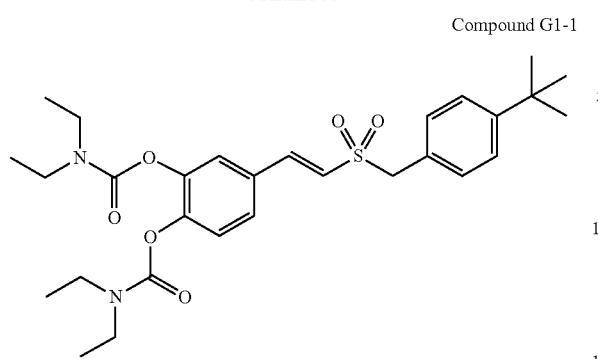
Compound H2-4
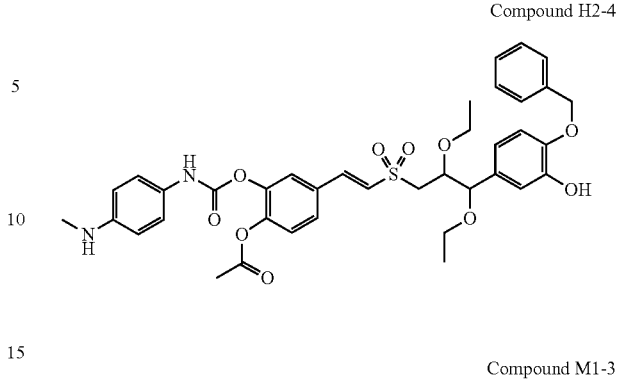
Compound E2-2
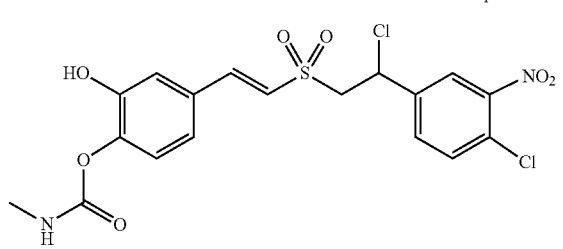
Compound M1-3
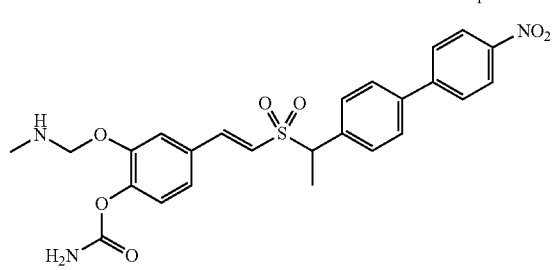
Compound K3-3
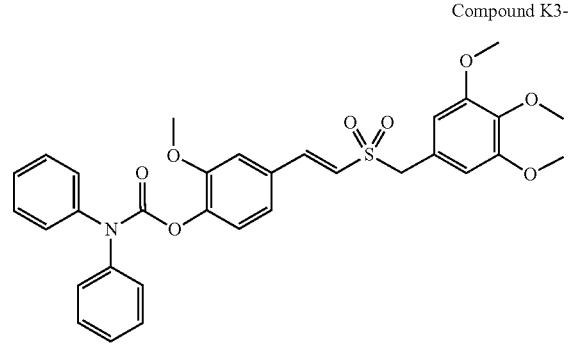
Compound L1-4
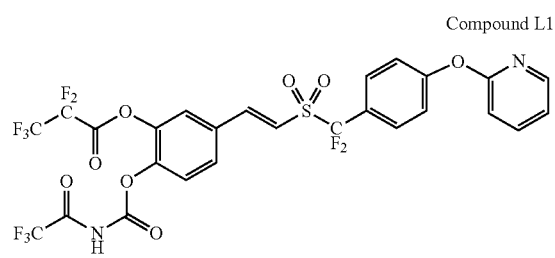
Compound K1-3
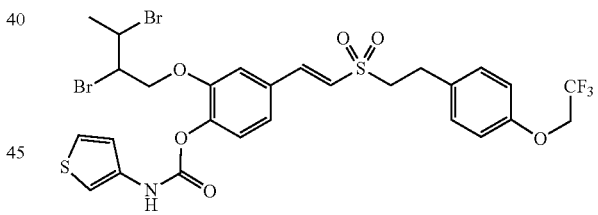
Compound K1-4
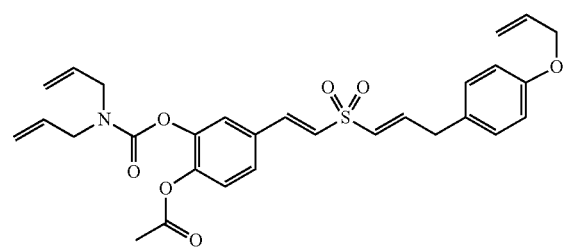
Compound J1-4
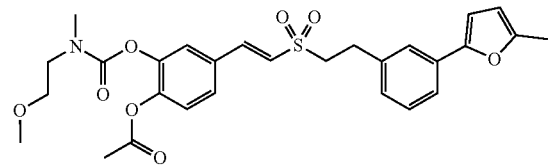
Compound P1-7
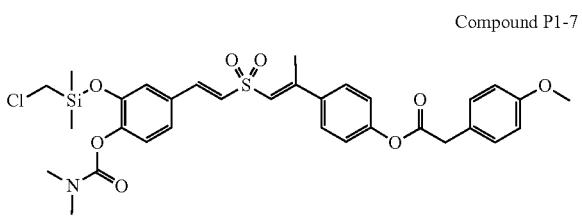
Compound A1-3
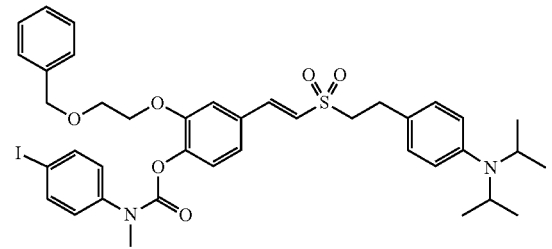

-continued

Compound M1-1

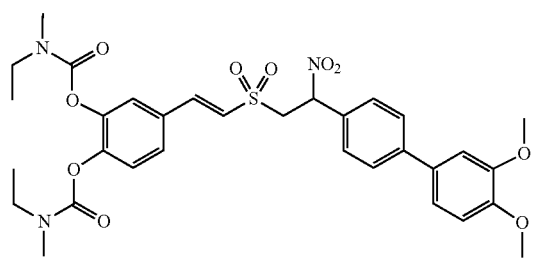

Compound P1-3

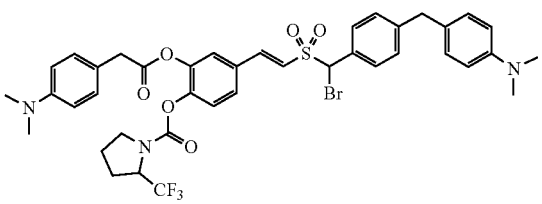

Compound M1-5

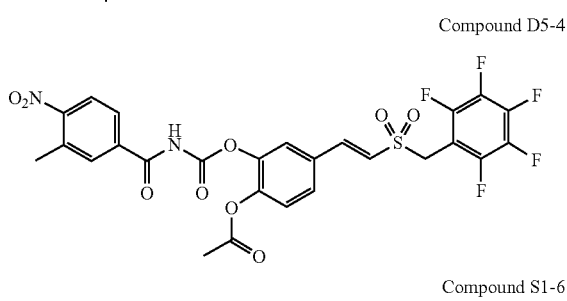

Compound R1-5

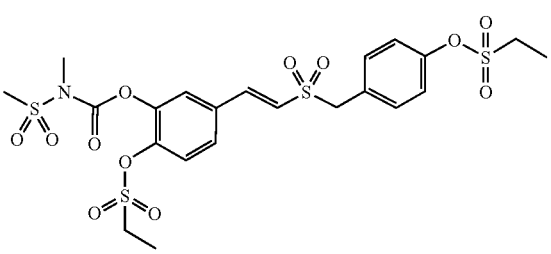

Compound D5-4

Compound S1-6

-continued

Compound S6-6

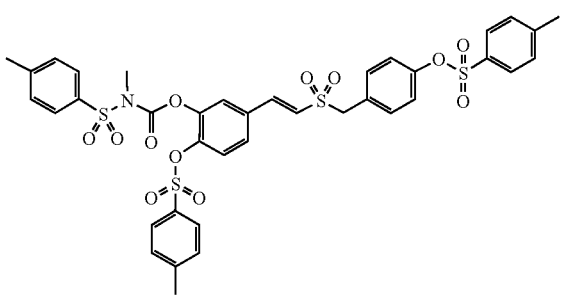

Compound P1-1

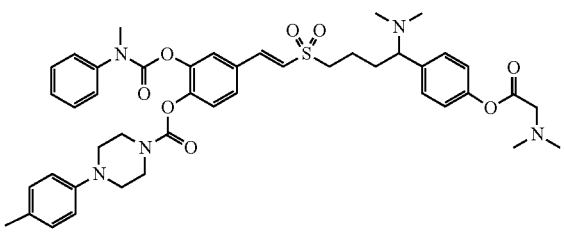

On the other hand, the invention provides a method for preparing the above compound of general formula I, comprising the following steps:

a) reacting a compound of general formula II with solid phosgene under an alkaline condition to produce a compound of general formula III;

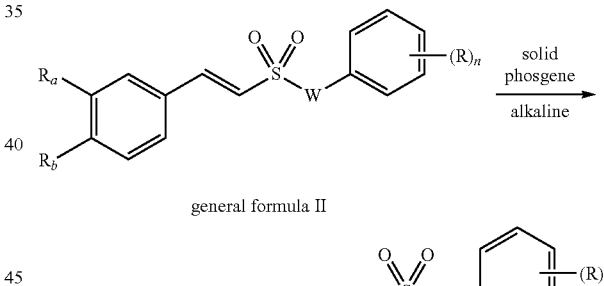

general formula II general formula III b) reacting the compound of general formula III with $NH_3$, $R_3NH_2$ or $(R_3)_2NH$ to produce the compound of general formula I, and

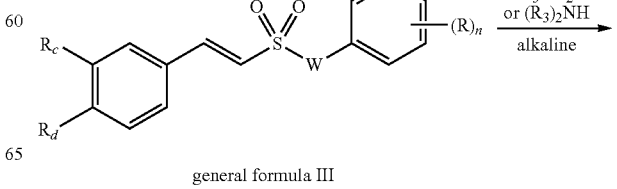

general formula III

-continued

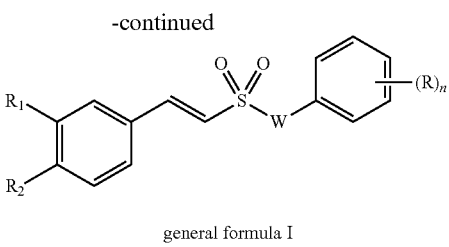

general formula I c) optionally, converting the compound of general formula I into its pharmaceutically acceptable salt;

wherein at least one of $R_a$ and $R_b$ is independently —OH; the other one of $R_a$ and $R_b$ is independently selected from: —OH, $C_{1-6}$ alkoxy unsubstituted or substituted by one to six halogen, —N(R$_4$)$_2$ or —OR$_5$, $C_{1-6}$ alkylacyloxy or $C_{7-10}$ arylacyloxy unsubstituted or substituted by one to six halogen, —N(R$_4$)$_2$ or —OR$_5$, sulfonyloxy substituted by $C_{1-3}$ alkyl or $C_{6-8}$ aryl, and —OSi(R$_6$)$_3$;

at least one of $R_c$ and $R_d$ is independently —OCOCl; the other one of $R_c$ and $R_d$ is independently selected from —OCOCl, $C_{1-6}$ alkoxy unsubstituted or substituted by one to six halogen, —N(R$_4$)$_2$ or —OR$_5$, $C_{1-6}$ alkylacyloxy or $C_{7-10}$ arylacyloxy unsubstituted or substituted by one to six halogen, —N(R$_4$)$_2$ or —OR$_5$, sulfonyloxy substituted by $C_{1-3}$ alkyl or $C_{6-8}$ aryl, —OSi(R$_6$)$_3$, and —OH;

wherein the definitions for W, R, n, $R_3$, $R_4$, $R_5$, and $R_6$ are as recited above.

Preferably, the base used in step a) is a moderately alkaline or weakly alkaline inorganic or organic base. Inorganic bases such as sodium hydroxide, potassium hydroxide, sodium bicarbonate, sodium carbonate, sodium acetate, and cesium carbonate can all be used, and the amount and concentration can be adjusted according to the strength of the base. If the organic base does not contain amino, primary amine and secondary amine structures can also be used, such as pyridine, triethylamine, 4-dimethylaminopyridine, DBU (1,8-diazabicycloundec-7-ene), DBN (1,5-diazabicyclo[4.3.0]non-5-ene), and MTBD (7-methyl-1,5,7-triazabicyclo[4.4.0]dec-5-ene).

Preferably, in step b), base may be absent and the reaction is completed depending upon the alkalinity of the raw material NH$_3$, R$_3$NH$_2$, or (R$_3$)$_2$NH per se, or the moderately alkaline or weakly alkaline inorganic or organic base used in step a) may be added in an appropriate amount to promote the completion of the reaction. In another aspect, the invention also provides a pharmaceutical composition, comprising a compound of general formula I or pharmaceutically acceptable salts thereof as above, as well as at least one pharmaceutically acceptable carrier.

The pharmaceutical composition of the compound of the invention can be administrated in any of the following manners: oral administration, spray inhalation, rectal administration, nasal administration, buccal administration, topical administration, and parenteral administration, such as subcutaneous, venous, intramuscular, intraperitoneal, intrathecal, intraventricular, intrasternal or intravenous administration. The pharmaceutical composition of the invention can be administrated alone or in combination with other neuroprotective drugs. The animals to be treated include mammals, reptiles, crustaceans, amphibians, fishes, and poultries. The main range is mammals, especially human.

When administrated orally, the compound of the invention can be prepared into any orally acceptable formulation form, including but not limited to tablets, capsules, aqueous solutions, or aqueous suspensions. Among them, the carrier used in the tablet may include filler, lubricant, disintegrant, and binder. The filler may include, but not limited to, starch, pregelatinized starch, dextrin, powdered sugar, lactose, mannitol, and microcrystalline cellulose. The lubricant include, but not limited to, stearic acid, calcium stearate, magnesium stearate, talc powder, oxidized vegetable oil, polyethylene glycol, sodium lauryl sulfate, micronized silica gel, and talc powder. The disintegrant may include, but not limited to, croscarmellose sodium, crospovidone, starch and its derivatives, low-substituted hydroxypropyl cellulose, and effervescent disintegrant. The binder may include, but not limited to, hydroxypropyl cellulose, povidone, starch syrup, dextrin, powdered sugar, syrup, mucilage, cellulose and derivatives thereof. The diluent used in the capsule formulation generally includes lactose and dried corn starch. The aqueous suspension formulation is used by mixing the active ingredient with a suitable suspension. The suspension may include, but not limited to, wetting agent, flocculant, and deflocculant. Optionally, some sweeteners, aromatics, or coloring agents can be added to above oral formulation forms.

In the case of topical administration, especially for treating affected surfaces or organs that are easily accessible by topical external application, such as ophthalmic, dermatic or lower intestinal neurological diseases, the compound of the invention can be prepared into different formulations for topical administration according to different affected surfaces or organs. The details are as follows:

In the case of ophthalmic topical administration, the compound of the invention can be formulated into a formulation form of micronized suspension or solution. The carrier used is isotonic sterile saline with a certain pH, and a preservative such as benzyl alkoxide chloride may or may not be added. For the ophthalmic use, the compound can also be prepared into an ointment form such as petrolatum ointment.

In the case of dermatic topical administration, the compound of the invention can be prepared into an appropriate form of ointment, lotion, or cream formulation, in which the active ingredient is suspended or dissolved in one or more carriers. The carrier that can be used in the ointment formulation include, but not limited to: mineral oil, liquid petrolatum, white petrolatum, propylene glycol, polyethylene oxide, polypropylene oxide, emulsifying wax, and water; and the carrier that can be used in the lotion or cream include, but not limited to: mineral oil, sorbitan monostearate, Tween 60, cetyl ester wax, hexadecenyl aromatic alcohol, 2-octyldodecanol, benzyl alcohol, and water.

The compound of the invention can also be administrated in the form of sterile injection formulation, including sterile injection water or oil suspension or sterile injection solution. Among them, the usable carrier or solvent include water, Ringer's solution, and isotonic sodium chloride solution. In addition, the sterile non-volatile oil can also be used as the solvent or suspension medium, such as monoglyceride or diglyceride.

In another aspect, the invention provides the use of the compound of general formula I or pharmaceutically acceptable salts thereof or the pharmaceutical composition as mentioned above in the manufacture of a medicament for antioxidation, anti-inflammation, neurocholinesterase resistance, or neuroprotection;

Preferably, the invention provides the use of the compound of general formula I or pharmaceutically acceptable salts thereof or the pharmaceutical composition as mentioned above in the manufacture of a medicament for treating and/or preventing Parkinson's disease.

In yet another aspect, the invention provides a method for treating Parkinson's disease, comprising administrating the above-mentioned compound of general formula I or pharmaceutically acceptable salts thereof or the above-mentioned pharmaceutical composition to a patient in need thereof.

The compound of general formula I of the invention has valuable pharmacological properties, especially pharmacological activities such as antioxidation, anti-inflammation, and neurocholinesterase resistance, as well as neuroprotective properties, and can be used for the treatment and/or prevention of Parkinson's disease.

In addition, it should be pointed out that the dosage and method for administering the compound of the invention depend on many factors, including the age, weight, gender, and natural health status of the patient, the active strength, administration period, and metabolism velocity of the compound, and the severity of the condition. The specific dosage and method is decided by the attending physician according to the specific conditions of the patient.

DETAILED DESCRIPTION OF THE PREFERRED EMBODIMENTS

In order to further illustrate the invention, a series of Examples are provided below. These Examples are completely illustrative, and only used to describe the invention in detail and should not be construed as limiting the invention. Unless otherwise specified, in the following Examples, the expression "the solvent is subjected to rotary evaporation under reduced pressure" generally refers to "the solvent is evaporated to dryness with a rotary evaporator under the condition of reduced pressure by a water pump."

The starting materials in the invention can be synthesized by the method in CN104230770B or according to methods known in the art, or can be directly purchased from reagent companies such as J&K Scientific Co., Ltd., Aladdin Reagent (Shanghai) Co., Ltd., and Beijing Ouhe Technology Co., Ltd.

Example 1: Preparation of (E)-4-{2-[(4-trifluoromethylphenyl)mesyl]ethenyl}-1,2-phenylenebis(diethylcarbamate) (Compound B1-1)

Step 1. Preparation of (E)-4-{2-[(4-trifluoromethylphenyl)mesyl]ethenyl}-1,2-phenylenebischloroformate (Compound B1-1-a)

Compound B1-1-a

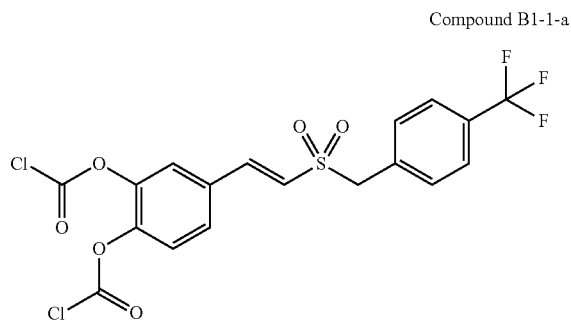 [SMILES: O=C(Cl)Oc1ccc(/C=C/S(=O)(=O)Cc2ccc(C(F)(F)F)cc2)cc1OC(=O)Cl]

The solid phosgene (475 mg, 1.6 mmol) was dissolved in dichloromethane (10 mL), cooled to 0° C. in an ice-water bath, and a solution of (E)-4-{2-[(4-trifluoromethylphenyl) mesyl]ethenyl}benzene-1,2-diol (860 mg, 2.4 mmol) in dichloromethane (20 mL) was slowly dropwise added over 30 min. After stirring for 15 min, a solution of pyridine (0.40 mL, 5.0 mmol) in dichloromethane (5 mL) was slowly dropwise added over 15 min. In the process of the above dropwise addition, the temperature of the reaction solution should be controlled to be no higher than 5° C. After the dropwise addition was completed, the reaction solution was allowed to be naturally warmed to room temperature, and reacted under stirring for 2 h. The reaction solution was washed with pre-cooled water (25 mL×3 times), dried over anhydrous magnesium sulfate and then filtered, and the filtrate was concentrated under reduced pressure to obtain Compound B1-1-a, as a yellowish oily liquid, which can be used in the next step without purification.

Step 2. Preparation of (E)-4-{2-[(4-trifluoromethylphenyl)mesyl]ethenyl}-1,2-phenylenebis(diethylcarbamate) (Compound B1-1)

Compound B1-1

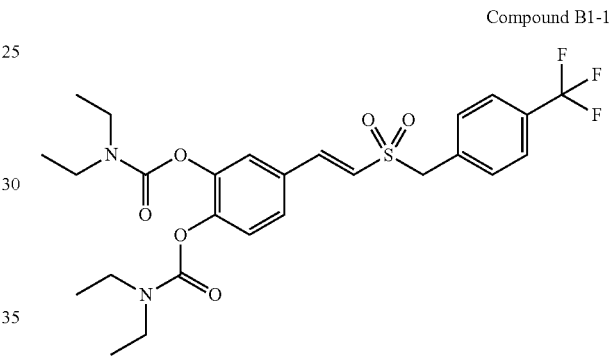

Compound B1-1-a obtained in step 1 was dissolved in tetrahydrofuran (5 mL), and added to a solution of diethylamine (0.52 mL, 5.0 mmol) in tetrahydrofuran (10 mL) at 0-5° C. The reaction solution was slowly warmed to room temperature and stirred overnight. After the reaction was completed under TLC monitoring, 30 mL of water was added, and extracted with diethyl ether (25 mL×3 times). The organic phases were combined, successively washed with 0.01 mol/L aqueous hydrochloric acid solution, saturated sodium bicarbonate aqueous solution, and saturated sodium chloride aqueous solution (each 50 mL), dried over anhydrous magnesium sulfate and then filtered, and the filtrate was concentrated under reduced pressure. The residue was purified by silica gel column chromatography (n-hexane/ethyl acetate system, v/v=9:1), to give a beige white solid product, i.e., Compound B1-1 (606 mg, yield: 45% over two steps).

Melting point: 107-109° C.

$^1$H NMR (CDCl$_3$) δ:1.19 (t, 12H, J=8.1 Hz, NCH$_2$CH$_3$), 3.23 (q, 8H, J=8.1 Hz, NCH$_2$CH$_3$), 4.65 (s, 2H, SO$_2$CH$_2$), 7.06-7.17 (m, 3H, CH=CHSO$_2$, ArH), 7.35-7.41 (m, 3H, ArH), 7.52 (m, 2H, ArH), 7.88 (d, 1H, J=15.0 Hz, CH=CHSO$_2$); $^{13}$C NMR (CDCl$_3$) δ:12.7 (NCH$_2$CH$_3$*4), 42.4 (NCH$_2$CH$_3$*4), 62.8 (SO$_2$CH$_2$), 118.7 (CH=CHSO$_2$), 120.6 (ArC), 121.7 (ArC), 124.2 (CF$_3$), 125.8 (ArC), 126.1 (ArC*2), 128.8 (ArC*2), 129.5 (ArC), 130.1 (ArC), 132.0 (ArC), 134.5 (CH=CHSO$_2$), 143.6 (ArC), 145.1 (ArC), 154.3 (NCOO), 154.8 (NCOO); HRMS-EI(M+): C$_{26}$H$_{31}$F$_3$N$_2$O$_6$S, calcd: 556.1855, found: 556.1865.

Example 2: Preparation of (E)-4-[2-(3-phenylpropylsulfonyl)ethenyl]-1,2-phenylenebis(diethylcarbamate) (Compound C1-1)

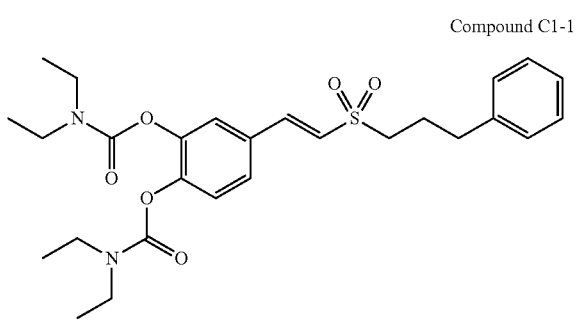 [SMILES: CCN(CC)C(=O)Oc1ccc(/C=C/S(=O)(=O)CCCc2ccccc2)cc1OC(=O)N(CC)CC]

Compound C1-1

With (E)-4-{2-[(3-phenylpropyl)sulfonyl]ethenyl}benzene-1,2-diol as starting material and in accordance with the preparation method in Example 1, Compound C1-1 was prepared by two steps, as a light yellow solid (yield: 42% over two steps).

Melting point: 96-99° C.

$^1$H NMR (CDCl$_3$) δ:1.26 (m, 12H, NCH$_2$CH$_3$), 2.19 (tt, 2H, J=7.6, 5.4 Hz, SO$_2$CH$_2$CH$_2$CH$_2$), 2.81 (t, 2H, J=7.6 Hz, SO$_2$CH$_2$CH$_2$CH$_2$), 3.06 (t, 2H, J=5.4 Hz, SO$_2$CH$_2$CH$_2$CH$_2$), 3.43 (m, 8H, NCH$_2$CH$_3$), 6.77 (d, 1H, J=15.4 Hz, CH=CHSO$_2$), 7.20-7.42 (m, 8H, ArH), 7.54 (d, 1H, J=15.4 Hz, CH=CHSO$_2$); $^{13}$C NMR (CDCl$_3$) δ:13.3 (NCH$_2$CH$_3$*2), 14.1 (NCH$_2$CH$_3$*2), 24.2 (SO$_2$CH$_2$CH$_2$CH$_2$), 34.2 (SO$_2$CH$_2$CH$_2$CH$_2$), 42.0 (NCH$_2$CH$_3$*2), 42.4 (NCH$_2$CH$_3$*2), 54.4 (SO$_2$CH$_2$CH$_2$CH$_2$), 123.4 (ArC), 124.3 (ArC), 125.0 (CH=CHSO$_2$), 126.5 (ArC), 126.6 (ArC), 128.5 (ArC*2), 128.7 (ArC*2), 130.1 (ArC), 139.9 (CH=CHSO$_2$), 143.6 (ArC), 143.9 (ArC), 146.0 (ArC), 152.8 (NCOO), 153.0 (NCOO); HRMS-EI(M+):C$_{27}$H$_{36}$N$_2$O$_6$S, calcd: 516.2294, found: 516.2282.

Example 3: Preparation of (E)-4-{2-[(4-chlorophenyl)mesyl]ethenyl}-1,2-phenylenebis(diethylcarbamate) (Compound D1-1)

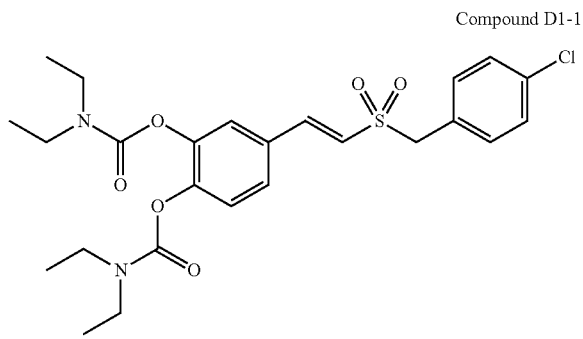 [SMILES: CCN(CC)C(=O)Oc1ccc(/C=C/S(=O)(=O)Cc2ccc(Cl)cc2)cc1OC(=O)N(CC)CC]

Compound D1-1

With (E)-4-{2-[(4-chlorophenyl)mesyl]ethenyl}benzene-1,2-diol as starting material and in accordance with the preparation method in Example 1, Compound D1-1 was prepared by two steps, as a light yellow solid (yield: 53% over two steps).

Melting point: 108-110° C.

$^1$H NMR (CDCl$_3$) δ:1.28 (m, 12H, NCH$_2$CH$_3$), 3.46 (m, 8H, NCH$_2$CH$_3$), 4.31 (s, 2H, SO$_2$CH$_2$), 6.71 (d, 1H, J=15.4 Hz, CH=CHSO$_2$), 7.32-7.45 (m, 8H, CH=CHSO$_2$, ArH); $^{13}$C NMR (CDCl$_3$) δ:13.3 (NCH$_2$CH$_3$), 14.2 (NCH$_2$CH$_3$), 42.0 (NCH$_2$CH$_3$), 42.4 (NCH$_2$CH$_3$), 61.2 (SO$_2$CH$_2$), 123.5 (ArC), 124.1 (CH=CHSO$_2$), 124.4 (ArC), 126.5 (ArC), 129.2 (ArC*2), 130.0 (ArC), 132.3 (ArC*2), 134.9 (ArC), 135.3 (CH=CHSO$_2$), 144.0 (ArC), 144.7 (ArC), 146.1 (ArC), 152.8 (NCOO), 153.0 (NCOO); HRMS-EI(M+): C$_{25}$H$_{31}$ClN$_2$O$_6$S, calcd: 522.1591, found: 522.1585.

Example 4: Preparation of (E)-4-{2-[(4-t-butylphenyl)mesyl]ethenyl}-1,2-phenylenebis(diethylcarbamate) (Compound G1-1)

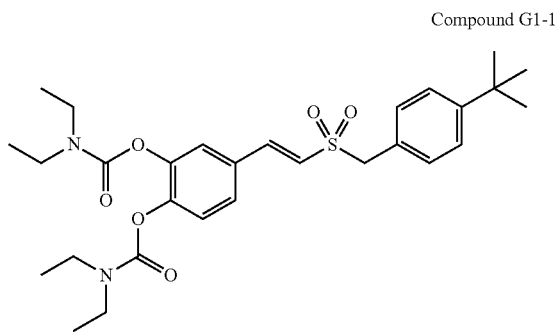 [SMILES: CCN(CC)C(=O)Oc1ccc(/C=C/S(=O)(=O)Cc2ccc(C(C)(C)C)cc2)cc1OC(=O)N(CC)CC]

Compound G1-1

With (E)-4-{2-[(4-t-butylphenyl)mesyl]ethenyl}benzene-1,2-diol as starting material and in accordance with the preparation method in Example 1, Compound G1-1 was prepared by two steps, as a white solid (yield: 56% over two steps).

Melting point: 95-98° C.

$^1$H NMR (CDCl$_3$) δ: 1.23 (m, 12H, NCH$_2$CH$_3$), 1.36 (m, 9H, t-Bu), 3.42 (m, 8H, NCH$_2$CH$_3$), 4.30 (s, 2H, SO$_2$CH$_2$), 6.70 (d, 1H, J=15.5 Hz, CH=CHSO$_2$), 7.24-7.33 (m, 5H, ArH), 7.40 (d, 1H, J=15.5 Hz, CH=CHSO$_2$), 7.45 (d, 2H, J=7.6 Hz, ArH); $^{13}$C NMR (CDCl$_3$) δ: 13.3 (NCH$_2$CH$_3$), 14.1 (NCH$_2$CH$_3$), 31.3 (C(CH$_3$)$_3$), 34.7 (C(CH$_3$)$_3$), 42.0 (NCH$_2$CH$_3$), 42.4 (NCH$_2$CH$_3$), 61.6 (SO$_2$CH$_2$), 123.4 (ArC), 124.3 (ArC), 124.6 (ArC), 124.9 (CH=CHSO$_2$), 125.9 (ArC*2), 126.4 (ArC), 130.2 (ArC), 130.6 (ArC*2), 143.9 (ArC), 144.1 (CH=CHSO$_2$), 145.9 (ArC), 152.0 (t-Bu-ArC), 152.8 (NCOO), 153.0 (NCOO); HRMS-EI(M+):C$_{29}$H$_{40}$N$_2$O$_6$S, calcd: 544.2607, found: 544.2604.

Example 5: Preparation of (E)-4-{2-[2-chloro-2-(4-chloro-3-nitrophenyl)ethylsulfonyl]ethenyl}-2-hydroxyphenyl-N-methylcarbamate (Compound E2-2)

Step 1. Preparation of (E)-4-{2-[2-chloro-2-(4-chloro-3-nitrophenyl)ethylsulfonyl]ethenyl}-2-hydroxyphenylchloroformate (Compound E2-2-a)

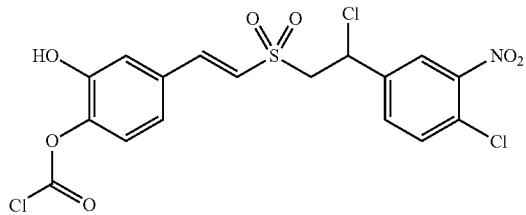

Compound E2-2-a

The solid phosgene (237 mg, 0.8 mmol) was dissolved in dichloromethane (10 mL), cooled to 0° C. in an ice-water bath, and a solution of (E)-4-{2-[2-chloro-2-(4-chloro-3-nitrophenyl)ethylsulfonyl]ethenyl}benzene-1,2-diol (1003 mg, 2.4 mmol) in dichloromethane (20 mL) was slowly dropwise added over 30 min. After stirring for 15 min, a solution of pyridine (0.20 mL, 2.5 mmol) in dichloromethane (5 mL) was slowly dropwise added over 15 min. In the process of the above dropwise addition, the temperature of the reaction solution should be controlled to be no higher than 5° C. After the dropwise addition was completed, the reaction solution was allowed to be naturally warmed to room temperature, and reacted under stirring for 2 h. The reaction solution was washed with pre-cooled water (25 mL×3 times), dried over anhydrous magnesium sulfate and then filtered, and the filtrate was concentrated under reduced pressure to obtain Compound E2-2-a, as a yellow oily liquid, which can be used in the next step without purification.

Step 2. Preparation of (E)-4-{2-[2-chloro-2-(4-chloro-3-nitrophenyl)ethylsulfonyl]ethenyl}-2-hydroxyphenyl-N-methylcarbamate (Compound E2-2)

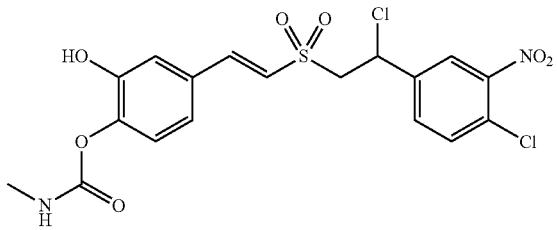

Compound E2-2

Compound E2-2-a obtained in step 1 was dissolved in tetrahydrofuran (5 mL), and added to a solution of methylamine (2 M solution in tetrahydrofuran, 1.25 mL, 2.5 mmol) in tetrahydrofuran (10 mL) at 0-5° C. The reaction was slowly warmed to room temperature and stirred overnight. After the reaction was completed under TLC monitoring, 30 mL of water was added, and extracted with diethyl ether (25 mL×3 times). The organic phases were combined, successively washed with 0.01 mol/L aqueous hydrochloric acid solution, saturated sodium bicarbonate aqueous solution, and saturated sodium chloride aqueous solution (each 50 mL), dried over anhydrous magnesium sulfate and then filtered, and the filtrate was concentrated under reduced pressure. The residue was purified by silica gel column chromatography (n-hexane/ethyl acetate system, v/v=15:2), to give a light yellow solid product, i.e., Compound E2-2 (403 mg, yield: 35% over two steps).

Melting point: 211-213° C.

$^1$H NMR (CDCl$_3$) δ:2.89 (s, 3H, NHC$\underline{H}_3$), 3.85 (dd, 1H, J=12.5, 7.0 Hz, SO$_2$C$\underline{H}_2$), 4.11 (dd, 1H, J=12.5, 7.0 Hz, SO$_2$C$\underline{H}_2$), 4.82 (brs, 1H, CONH), 5.67 (m, 1H, CHCl), 6.87 (d, 1H, J=7.5 Hz, ArH), 6.95-7.33 (m, 6H, CH═C$\underline{H}$SO$_2$, ArOH, ArH), 7.41 (d, 1H, J=7.4 Hz, ArH), 7.63 ($\underline{d}$, 1H, J=15.5 Hz, C$\underline{H}$═CHSO$_2$); $^{13}$C NMR (CDCl$_3$) δ:27.5 (NHCH$_3$), 49.3 (CHCl), 62.5 (SO$_2$CH$_2$), 115.2 (ArC), 120.9 (CH═$\underline{C}$HSO$_2$), 121.6 (ArC), 122.7 (ArC), 126.1 (ArC), 125.9 (ArC), 128.7 (ArC), 130.2 (ArC), 130.8 (ArC), 134.9 (ArC), 139.3 (ArC—OCO), 142.5 (ArC—NO$_2$), 143.8 ($\underline{C}$H═CHSO$_2$), 149.1 (ArC—OH), 155.2 (NCOO); HRMS-EI(M+):C$_{18}$H$_{16}$Cl$_2$N$_2$O$_7$S, calcd: 474.0055, found: 474.0072.

Example 6: Preparation of (E)-2-methoxy-4-{2-[(3,4,5-trimethoxyphenyl)mesyl]ethenyl}-phenyl-N,N-diphenylcarbamate (Compound K3-3)

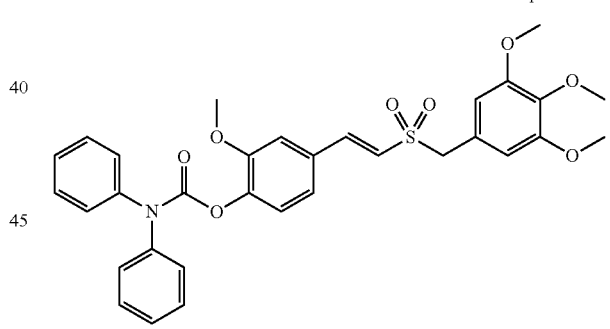

Compound K3-3

With (E)-2-methoxy-4-{2-[(3,4,5-trimethoxyphenyl)mesyl]ethenyl}phenol as starting material and in accordance with the preparation method in Example 5, Compound K3-3 was prepared by two steps, as a beige white solid product (yield: 51% over two steps).

Melting point: 195-197° C.

$^1$H NMR (CDCl$_3$) δ:3.85 (m, 12H, OCH$_3$), 4.66 (s, 2H, SO$_2$CH$_2$), 6.75-7.21 (m, 6H, CH═C$\underline{H}$SO$_2$, ArH), 7.35-7.51 (m, 10H, N—ArH), 7.90 (d, 1H, J=15.5 Hz, C$\underline{H}$═CHSO$_2$); $^{13}$C NMR (CDCl$_3$) δ:56.0 (OCH$_3$*2), 56.2 (OCH$_3$), 59.3 (SO$_2$CH$_2$), 60.7 (OCH$_3$), 108.9 (ArC*2), 111.4 (ArC), 120.5 (CH═$\underline{C}$HSO$_2$), 122.3 (ArC), 122.6 (ArC), 126.9 (ArC*4), 127.2 (ArC), 128.1 (ArC*2), 129.9 (ArC), 130.2 (ArC*4), 137.1 (ArC), 137.5 ($\underline{C}$H═CHSO$_2$), 141.2 (ArC*2), 144.6 (ArC), 149.9 (ArC*2), 150.7 (ArC), 154.7 (NCOO); HRMS-EI(M+):C$_{32}$H$_{31}$NO$_8$S, calcd: 589.1770, found: 589.1761.

Example 7: Preparation of 4-{(E)-2-[(E)-3-(4-allyloxyphenyl)prop-1-en-1-yl]sulfonylethenyl}-2-(N,N-diallylcarbamoyloxy)phenyl acetate (Compound K1-4)

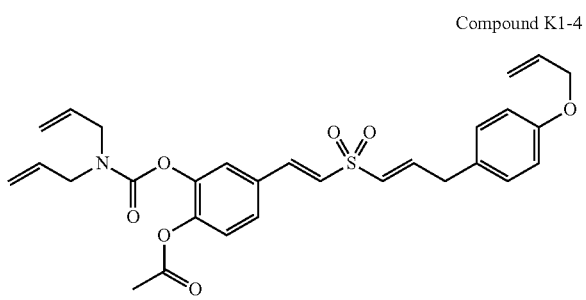 [SMILES: C=CCOc1ccc(C/C=C/S(=O)(=O)/C=C/c2ccc(OC(C)=O)c(OC(=O)N(CC=C)CC=C)c2)cc1]

Compound K1-4

With 4-{(E)-2-[(E)-3-(4-allyloxyphenyl)prop-1-en-1-yl]sulfonylethenyl}-2-hydroxyphenyl acetate as starting material and in accordance with the preparation method in Example 5, Compound K1-4 was prepared by two steps, as a white solid (yield: 38% over two steps).

Melting point: 146-149° C.

$^1$H NMR (CDCl$_3$) δ:2.54 (s, 3H, CH$_3$CO), 3.42 (m, 2H, CH$_2$Ar), 3.66 (d, 4H, J=6.1 Hz, CH$_2$=CHCH$_2$N), 4.63 (d, 2H, J=6.0 Hz, CH$_2$=CHCH$_2$O), 5.19-5.53 (m, 6H, CH$_2$=CHCH$_2$N, CH$_2$=CHCH$_2$O), 5.89-6.05 (m, 3H, CH$_2$=CHCH$_2$N, CH$_2$=CHCH$_2$O), 6.36 (d, 1H, J=15.2 Hz, SO$_2$CH=CHCH$_2$), 6.73-7.30 (m, 8H, ArCH=CHSO$_2$, ArH), 7.46 (dt, 1H, j=15.1 Hz, 6.2 Hz, SO$_2$CH=CHCH$_2$), 8.05 (d, 1H, J=15.3 Hz, ArCH=CHSO$_2$); $^{13}$C NMR (CDCl$_3$) δ:20.3 (CH$_3$CO), 38.1 (CH$_2$Ar), 49.8 (CH$_2$=CHCH$_2$N*2), 68.5 (CH$_2$=CHCH$_2$O), 115.0 (ArC*2), 117.5 (CH$_2$=CHCH$_2$N*2), 117.9 (CH$_2$=CHCH$_2$O), 122.1 (ArC), 122.6 (ArC), 124.7 (ArC), 126.1 (ArCH=CHSO$_2$), 129.1 (ArC*2), 130.8 (ArC), 132.7 (CH$_2$=CHCH$_2$N*2), 133.1 (CH$_2$=CHCH$_2$O), 133.9 (ArCH=CHSO$_2$), 135.0 (ArC), 137.4 (SO$_2$CH=CHCH$_2$), 142.1 (ArC), 142.9 (ArC), 143.3 (SO$_2$CH=CHCH$_2$), 153.6 (NCOO), 157.4 (ArC), 168.6 (CH$_3$COO); HRMS-EI(M+): C$_{29}$H$_{31}$NO$_7$S, calcd: 537.1821, found: 537.1804.

Example 8: Preparation of 4-{(E)-1-[(E)-3-(chloromethyldimethylsiloxy)-4-(N,N-dimethylcarbamoyloxy)styrylsulfonyl]prop-1-en-2-yl}phenyl-2-(4-methoxyphenyl) acetate (Compound P1-7)

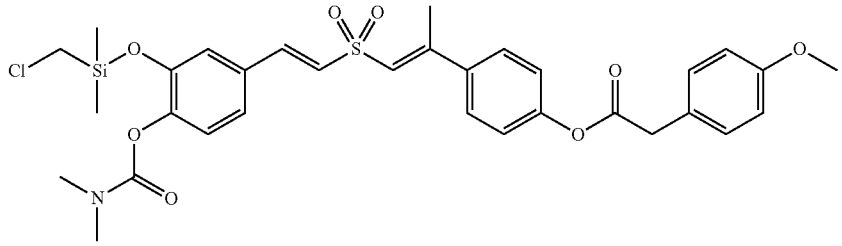

Compound P1-7

With 4-{(E)-1-[(E)-3-(chloromethyldimethylsiloxy)-4-hydroxystyrylsulfonyl]prop-1-en-2-yl}phenyl-2-(4-methoxyphenyl) acetate as starting material and in accordance with the preparation method in Example 5, Compound P1-7 was prepared by two steps, as a white solid (yield: 43% over two steps).

Melting point: 123-125° C.

$^1$H NMR (CDCl$_3$) δ:0.13 (s, 6H, SiCH$_3$*2), 2.24 (s, 3H, CH$_3$C=CH), 2.72 (s, 2H, ClCH$_2$Si), 3.15 (s 3H, CH$_3$N), 3.27 (s 3H, CH$_3$N), 3.81 (s, 3H, OCH$_3$), 4.11 (s, 2H, OCOCH$_2$), 6.75 (SO$_2$CH=C), 6.85-7.05 (m, 6H, CH=CHSO$_2$, ArH), 7.20-7.32 (m, 6H, ArH), 8.08 (CH=CHSO$_2$); $^{13}$C NMR (CDCl$_3$) δ:−1.8 (SiCH$_3$*2), 15.3 (CH$_3$C=CH), 29.8 (ClCH$_2$Si), 36.8 (NCH$_3$*2), 41.2 (OCOCH$_2$), 55.3 (OCH$_3$), 114.4 (ArC*2), 116.7 (ArC), 121.0 (ArC), 121.3 (ArC*2), 121.5 (ArC), 124.9 (CH=CHSO$_2$), 126.7 (ArC), 126.9 (ArC*2), 128.7 (SO$_2$CH=C), 130.0 (ArC), 130.5 (ArC*2), 131.7 (CH=CHSO$_2$), 137.6 (ArC), 142.2 (ArC), 147.8 (ArC), 148.8 (CH$_3$C=CH), 150.9 (ArC), 154.8 (NCOO), 158.0 (ArC), 169.7 (OCOCH$_2$); HRMS-EI(M+): C$_{32}$H$_{36}$ClNO$_8$SSi, calcd: 657.1619, found: 657.1633.

Example 9: Preparation of (E)-4-{2-[3-(4-benzyloxy-3-hydroxyphenyl)-2,3-diethoxypropyl]sulfonylethenyl}-2-[N-(4-methylaminophenyl)carbamoyloxy]phenyl acetate (Compound H2-4)

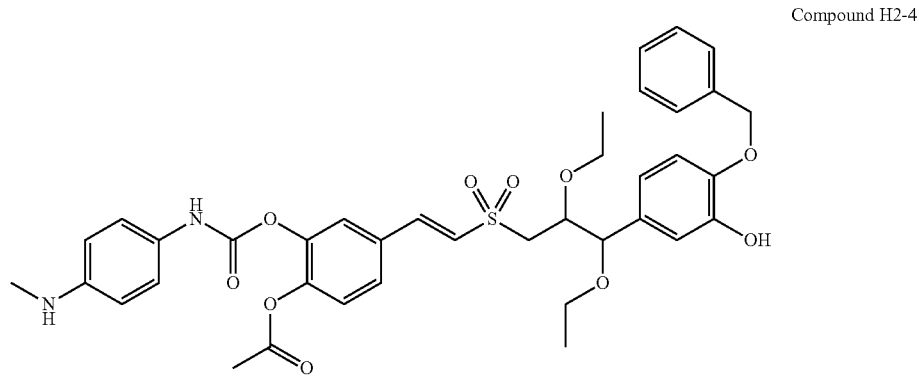 [SMILES: CCOC(CS(=O)(=O)/C=C/c1ccc(OC(C)=O)c(OC(=O)Nc2ccc(NC)cc2)c1)C(OCC)c1ccc(OCc2ccccc2)c(O)c1]

Compound H2-4

With (E)-4-{2-[3-(4-benzyloxy-3-hydroxyphenyl)-2,3-diethoxypropyl]sulfonylethenyl}-2-hydroxyphenyl acetate as starting material and in accordance with the preparation method in Example 5, Compound H2-4 was prepared by two steps, as a light yellow solid (yield: 18% over two steps).

Melting point: 182-183° C.

$^1$H NMR (CDCl$_3$) δ:1.19 (m, 6H, OCH$_2$CH$_3$*2), 2.49 (s, 3H, CH$_3$CO), 2.70 (s, 3H, CH$_3$NH), 3.03 (m, 2H, OCH$_2$CH$_3$), 3.40 (m, 1H, SO$_2$CH$_2$), 3.62 (m, 1H, SO$_2$CH$_2$), 3.81 (dq, 1H, J=12.5, 8.1 Hz, OCH$_2$CH$_3$), 4.19 (dq, 1H, J=12.5, 8.1 Hz, OCH$_2$CH$_3$), 4.30 (brs, 1H, CH$_3$NH), 4.55 (m, 1H, SO$_2$CH$_2$CH), 4.72 (m, 1H, OCHAr), 5.22 (m, 2H, OCH$_2$Ph), 5.90 (brs, 1H, Ar—OH), 6.48 (d, 2H, J=7.5 Hz, ArH), 6.68-6.81 (m, 3H, NHCOO, ArH), 6.98-7.09 (m, 2H, ArH), 7.16 (d, 1H, J=15.3 Hz, CH=CHSO$_2$), 7.25-7.45 (m, 9H, ArH), 8.11 (d, 1H, J=15.2 Hz, CH=CHSO$_2$); $^{13}$C NMR (CDCl$_3$) δ:15.3 (OCH$_2$CH$_3$), 15.4 (OCH$_2$CH$_3$), 20.5 (CH$_3$CO), 29.8 (CH$_3$NH), 50.7 (SO$_2$CH$_2$), 64.8 (OCH$_2$CH$_3$), 65.2 (OCH$_2$CH$_3$), 70.7 (OCH$_2$Ph), 71.9 (SO$_2$CH$_2$CH), 81.5 (OCHAr), 114.9 (ArC), 115.8 (ArC), 116.9 (CH=CHSO$_2$), 117.1 (ArC*2), 119.9 (ArC), 121.9 (ArC), 122.3 (ArC), 122.8 (ArC*2), 125.3 (ArC), 127.6 (ArC*2), 127.8 (ArC), 128.5 (ArC*2), 129.8 (ArC), 133.0 (ArC), 133.3 (ArC), 134.2 (CH=CHSO$_2$), 135.1 (ArC), 142.3 (ArC), 143.2 (ArC), 146.1 (ArC), 146.2 (ArC), 151.6 (ArC), 154.1 (NHCOO), 168.6 (CH$_3$CO); HRMS-EI(M+): C$_{38}$H$_{42}$N$_2$O$_{10}$S, calcd: 718.2560, found: 718.2537.

Example 10: Preparation of (E)-2-[(methylamino)methoxy]-4-{2-[1-(4'-nitro-[1,1'-biphenyl]-4-yl)ethylsulfonyl]ethenyl}phenylcarbamate (Compound M1-3)

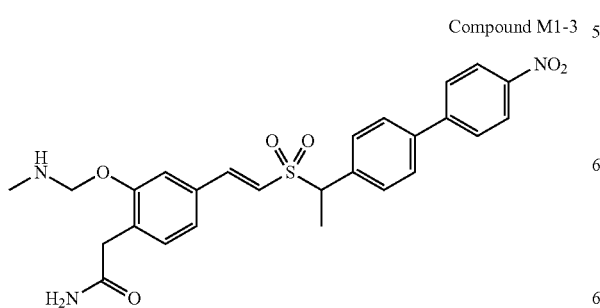

Compound M1-3

With (E)-2-[(methylamino)methoxy]-4-{2-[1-(4'-nitro-[1,1'-biphenyl]-4-yl)ethylsulfonyl]ethenyl}phenol as starting material and in accordance with the preparation method in Example 5, Compound M1-3 was prepared by two steps, as a yellow solid (yield: 33% over two steps).

Melting point: 256-258° C.

$^1$H NMR (CDCl$_3$) δ:1.12 (brs, 1H, CH$_3$NH), 1.73 (d, 3H, J=6.8 Hz, CHCH$_3$), 2.44 (s, 3H, CH$_3$NH), 4.39 (q, 1H, J=6.8 Hz, CHCH$_3$), 4.89 (brs, 2H, NH$_2$COO), 5.02 (d, 1H, J=12.5 Hz, NHCH$_2$O), 5.53 (d, 1H, J=12.5 Hz, NHCH$_2$O), 6.88 (d, 1H, J=7.6 Hz, ArH), 7.12-7.33 (m, 5H, CH=CHSO$_2$, ArH), 7.61 (d, 2H, J=7.6 Hz, ArH), 7.68 (m, 4H, ArH), 8.12 (d, 1H, J=15.2 Hz, CH=CHSO$_2$); $^{13}$C NMR (CDCl$_3$) δ:15.3 (CH$_3$CH), 35.0 (CH$_3$NH), 67.5 (CH$_3$CH), 82.1 (NHCH$_2$O), 113.8 (ArC), 122.6 (ArC), 123.9 (ArC), 124.6 (CH=CHSO$_2$), 126.7 (ArC*2), 128.2 (ArC*2), 128.9 (ArC*2), 129.5 (ArC*2), 130.9 (ArC), 134.7 (ArC), 136.0 (ArC), 137.5 (ArC), 138.5 (CH=CHSO$_2$), 138.9 (ArC), 142.7 (ArC), 148.5 (ArC), 156.1 (NH$_2$COO); HRMS-EI (M+):C$_{25}$H$_{25}$N$_3$O$_7$S, calcd: 511.1413, found: 511.1418.

Example 11: Preparation of (E)-5-{2-[(4-[pyridin-2-yl-oxy]phenyl)difluoromethylsulfonyl]ethenyl}-2-[N-(2,2,2-trifluoroacetyl)carbamoyloxy]phenyl-2,2,3,3,3-pentafluoropropionate (Compound L1-4)

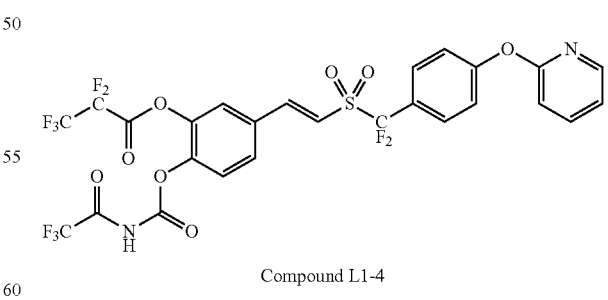

Compound L1-4

With (E)-5-{2-[(4-[pyridin-2-yl-oxy]phenyl)difluoromethylsulfonyl]ethenyl}-2-hydroxyphenyl-2,2,3,3,3-pentafluoropropionate as starting material and in accordance with the preparation method in Example 5, Compound L1-4 was prepared by two steps, as a light yellow solid (yield: 40% over two steps).

Melting point: 153-156° C.

$^1$H NMR (CDCl$_3$) δ:6.36 (brs, 1H, CF$_3$CONH), 6.79-6.91 (m, 2H, ArH), 7.03-7.09 (m, 3H, ArH), 7.16 (d, 1H, J=15.1 Hz, CH=CHSO$_2$), 7.23-7.32 (m, 1H, ArH), 7.33-7.54 (m, 4H, ArH), 8.09 (d, 1H, J=15.1 Hz, CH=CHSO$_2$), 8.79 (d, 1H, J=5.0 Hz, ArH); $^{13}$C NMR (CDCl$_3$) δ:9.3 (CF$_3$CF$_2$CO), 23.9 (CF$_3$CO), 27.2 (CF$_3$CF$_2$CO), 58.5 (SO$_2$CF$_2$), 112.9 (ArC), 119.1 (CH=CHSO$_2$), 120.4 (ArC), 120.9 (ArC), 121.5 (ArC*2), 123.8 (ArC), 125.2 (ArC), 126.9 (ArC), 129.5 (ArC*2), 130.7 (ArC), 134.6 (CH=CHSO$_2$), 139.4 (ArC), 141.8 (ArC), 143.6 (ArC), 147.7 (ArC), 151.9 (NHCOO), 153.0 (ArC), 162.8 (ArC), 169.1 (CF$_3$CO), 172.8 (CF$_3$CF$_2$CO); HRMS-EI(M+):C$_{26}$H$_{14}$F$_{10}$N$_2$O$_8$S, calcd: 704.0311, found: 704.0336.

Example 12: Preparation of (E)-2-(2,3-dibromobutoxy)-4-{2-[4-(2,2,2-trifluoroethoxy)phenylethylsulfonyl]ethenyl}phenyl-N-(thien-3-yl)carbamate (Compound K1-3)

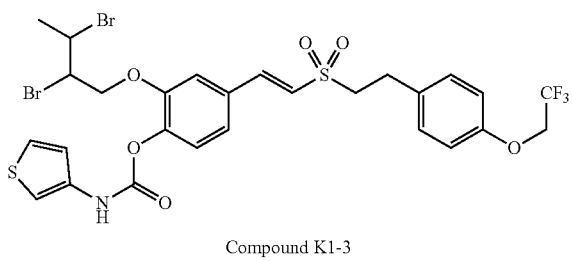 [SMILES: CC(Br)C(Br)COc1cc(/C=C/S(=O)(=O)CCc2ccc(OCC(F)(F)F)cc2)ccc1OC(=O)Nc1ccsc1]

Compound K1-3

With (E)-2-(2,3-dibromobutoxy)-4-{2-[4-(2,2,2-trifluoroethoxy)phenylethylsulfonyl]ethenyl}phenol as starting material and in accordance with the preparation method in Example 5, Compound K1-3 was prepared by two steps, as an orange-yellow solid (yield: 25% over two steps).

Melting point: 110-113° C.

$^1$H NMR (CDCl$_3$) δ:1.79 (d, 3H, J=7.0 Hz, CH$_3$CHBr), 3.09-3.28 (m, 4H, SO$_2$CH$_2$CH$_2$), 4.17 (m, 1H, OCH$_2$CHBr), 4.25-4.35 (m, 3H, CF$_3$CH$_2$O, CH$_3$CHBr), 4.65 (m, 1H, OCH$_2$CHBr), 4.97 (m, 1H, OCH$_2$CHBr), 6.12 (s, 1H, ArH), 6.45 (m, 1H, ArH), 6.63 (brs, 1H, NHCOO), 6.85 (m, 2H, ArH), 7.01 (d, 1H, J=7.6 Hz, ArH), 7.15-7.29 (m, 5H, CH=CHSO$_2$, ArH), 7.41 (d, 1H, J=7.5 Hz, ArH), 8.11 (d, 1H, J=15.4 Hz, CH=CHSO$_2$); $^{13}$C NMR (CDCl$_3$) δ:14.7 (CF$_3$), 23.0 (CH$_3$CHBr), 30.1 (SO$_2$CH$_2$CH$_2$), 49.5 (CH$_3$CHBr), 52.6 (SO$_2$CH$_2$CH$_2$), 60.2 (OCH$_2$CHBr), 64.2 (OCH$_2$CF$_3$), 70.1 (OCH$_2$CHBr), 105.7 (ArC), 113.8 (ArC), 114.7 (ArC*2), 120.3 (CH=CHSO$_2$), 122.6 (ArC), 123.4 (ArC), 124.1 (ArC), 126.8 (ArC), 129.5 (ArC*2), 130.4 (ArC), 130.8 (ArC), 133.1 (ArC), 136.0 (CH=CHSO$_2$), 144.4 (ArC), 149.2 (ArC), 154.1 (NHCOO), 157.1 (ArC); HRMS-EI(M+):C$_{27}$H$_{26}$Br$_2$F$_3$NO$_6$S$_2$, calcd: 740.9500, found: 740.9495.

Example 13: Preparation of (E)-2-[N-(2-methoxyethyl)-N-methylcarbamoyloxy]-4-{2-[3-(5-methylfur-2-yl)phenylethylsulfonyl]ethenyl}phenyl acetate (Compound J1-4)

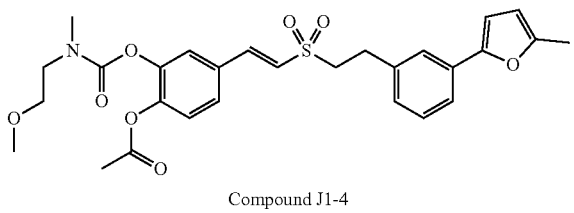 [SMILES: COCCN(C)C(=O)Oc1cc(/C=C/S(=O)(=O)CCc2cccc(-c3ccc(C)o3)c2)ccc1OC(C)=O]

Compound J1-4

With (E)-2-hydroxy-4-{2-[3-(5-methylfur-2-yl)phenylethylsulfonyl]ethenyl}phenyl acetate as starting material and in accordance with the preparation method in Example 5, Compound J1-4 was prepared by two steps, as a light yellow solid (yield: 43% over two steps).

Melting point: 191-193° C.

$^1$H NMR (CDCl$_3$) δ:2.34 (furan-CH$_3$), 2.52 (CH$_3$CO), 3.13 (m, 5H, SO$_2$CH$_2$CH$_2$, CH$_3$N), 3.36 (CH$_3$O), 3.60 (t, 2H, J=4.0 Hz, CH$_2$NCH$_3$), 3.75 (m, 4H, CH$_3$OCH$_2$, SO$_2$CH$_2$CH$_2$), 6.10 (d, 1H, J=7.5 Hz, ArH), 6.84 (d, 1H, J=7.5 Hz, ArH), 6.96 (d, 1H, J=7.4 Hz, ArH), 7.08 (d, 1H, J=15.1 Hz, CH=CHSO$_2$), 7.15-7.32 (m, 3H, ArH), 7.42 (t, 1H, J=7.5 Hz, ArH), 7.55 (m, 2H, ArH), 8.10 (d, 1H, J=15.2 Hz, CH=CHSO$_2$); $^{13}$C NMR (CDCl$_3$) δ:13.5 (furan-CH$_3$), 20.7 (CH$_3$CO), 30.2 (SO$_2$CH$_2$CH$_2$), 42.7 (CH$_3$N), 49.8 (CH$_2$NCH$_3$), 53.1 (SO$_2$CH$_2$CH$_2$), 58.2 (CH$_3$O), 72.7 (CH$_3$OCH$_2$), 107.1 (ArC), 108.5 (ArC), 120.4 (CH=CHSO$_2$), 121.9 (ArC), 122.5 (ArC), 122.8 (ArC), 124.8 (ArC), 127.1 (ArC), 127.9 (ArC), 129.6 (ArC), 130.0 (ArC), 130.9 (ArC), 135.9 (CH=CHSO$_2$), 138.0 (ArC), 142.1 (ArC), 143.2 (ArC), 150.9 (ArC), 152.6 (ArC), 154.5 (NCOO), 168.8 (CH$_3$COO); HRMS-EI(M+):C$_{28}$H$_{31}$NO$_8$S, calcd: 541.1770, found: 541.1793.

Example 14: Preparation of (E)-2-(2-benzyloxyethoxy)-4-{2-[4-(N,N-diisopropylamino)phenylethylsulfonyl]ethenyl}phenyl-N-(4-iodophenyl)-N-methylcarbamate (Compound A1-3)

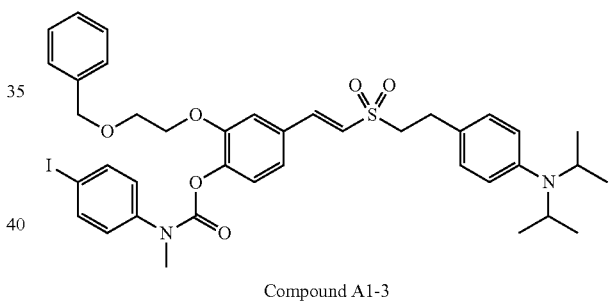

Compound A1-3

With (E)-2-(2-benzyloxyethoxy)-4-{2-[4-(N,N-diisopropylamino)phenylethylsulfonyl]ethenyl}phenol as starting material and in accordance with the preparation method in Example 5, Compound A1-3 was prepared by two steps, as an orange-red solid (yield: 31% over two steps).

Melting point: 170-172° C.

$^1$H NMR (CDCl$_3$) δ: 1.32 (m, 12H, CH(CH$_3$)$_2$*2), 3.02 (t, 2H, J=8.3 Hz, SO$_2$CH$_2$CH$_2$), 3.77 (t, 2H, J=8.3 Hz, SO$_2$CH$_2$CH$_2$), 3.84 (m, 5H, BzOCH$_2$, NCH$_3$), 4.18 (t, 2H, J=7.2 Hz, CH$_2$OAr), 4.47 (m, 4H, PhCH$_2$O, CH(CH$_3$)$_2$*2), 6.67 (d, 2H, J=7.4 Hz, ArH), 7.02 (d, 2H, J=7.5 Hz, ArH), 7.06-7.21 (m, 6H, CH=CHSO$_2$, ArH), 7.35 (m, 5H, ArH), 7.52 (d, 2H, J=7.5 Hz, ArH), 8.12 (d, 1H, J=15.3 Hz, CH=CHSO$_2$); $^{13}$C NMR (CDCl$_3$) δ: 20.9 (CH(CH$_3$)$_2$*2), 30.3 (SO$_2$CH$_2$CH$_2$), 35.1 (NCH$_3$), 48.9 (CH(CH$_3$)$_2$*2), 52.8 (SO$_2$CH$_2$CH$_2$), 69.3 (CH$_2$OAr), 70.2 (BzOCH$_2$), 73.0 (PhCH$_2$O), 88.2 (I—ArC), 114.1 (ArC), 118.1 (ArC*2), 119.7 (CH=CHSO$_2$), 120.6 (ArC*2), 122.8 (ArC), 123.0 (ArC), 127.9 (ArC*2), 128.1 (ArC), 128.8 (ArC*2), 129.9 (ArC*2), 130.2 (ArC), 131.1 (ArC), 136.0 (CH=CHSO$_2$), 136.8 (ArC*2), 138.1 (ArC), 143.9 (ArC), 144.7 (ArC), 147.6 (ArC), 149.3 (ArC), 155.4 (NCOO); HRMS-EI(M+): C$_{39}$H$_{45}$IN$_2$O$_6$S, calcd: 796.2043, found: 796.2048.

Example 15: Preparation of (E)-4-{2-[2-(3',4'-dimethoxy-[1,1'-biphenyl]-4-yl)-2-nitroethylsulfonyl]ethenyl}-1,2-phenylenebis(N-ethyl-N-methylcarbamate) (Compound M1-1)

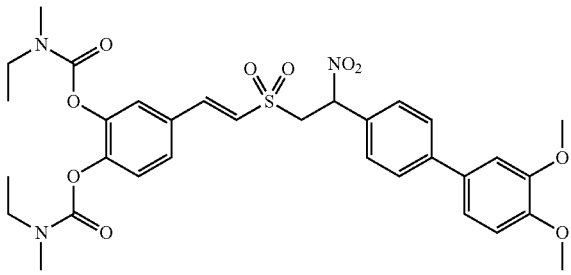

Compound M1-1

With (E)-4-{2-[2-(3',4'-dimethoxy-[1,1'-biphenyl]-4-yl)-2-nitroethylsulfonyl]ethenyl}benzene-1,2-diol as starting material and in accordance with the preparation method in Example 1, Compound M1-1 was prepared by two steps, as a white solid (yield: 67% over two steps).

Melting point: 159-161° C.

$^1$H NMR (CDCl$_3$) δ:1.22 (t, 6H, J=8.0 Hz, NCH$_2$CH$_3$*2), 3.16 (s, 6H, NCH$_3$*2), 3.38-3.55 (m, 4H, SO$_2$CH$_a$H$_b$CH, NCH$_a$H$_b$CH$_3$*2), 3.72 (m, 1H, SO$_2$CH$_a$H$_b$CH), 3.85 (s, 3H, OCH$_3$), 3.91 (s, 3H, OCH$_3$), 4.06 (m, 1H, NCH$_a$H$_b$CH$_3$), 4.20 (m, 1H, NCH$_a$H$_b$CH$_3$), 7.02 (d, 1H, J=7.6 Hz, ArH), 7.15-7.33 (m, 6H, CH=CHSO$_2$, ArH), 7.46 (m, 2H, ArH), 7.58 (d, 2H, J=7.5 Hz, ArH), 8.10 (d, 1H, J=15.3 Hz, CH=CHSO$_2$); $^{13}$C NMR (CDCl$_3$) δ:12.0 (NCH$_2$CH$_3$*2), 32.3 (CHNO$_2$), 36.1 (NCH$_3$*2), 46.3 (NCH$_2$CH$_3$*2), 54.3 (SO$_2$CH$_2$), 56.5 (OCH$_3$*2), 112.0 (ArC), 113.5 (ArC), 117.6 (CH=CHSO$_2$), 119.0 (ArC), 121.6 (ArC), 123.1 (ArC), 126.1 (ArC), 126.8 (ArC*2), 128.2 (ArC*2), 128.9 (ArC), 134.1 (ArC), 136.2 (CH=CHSO$_2$), 138.3 (ArC), 141.9 (ArC), 143.2 (ArC), 144.7 (ArC), 150.6 (ArC), 151.1 (ArC), 154.7 (NCOO), 154.9 (NCOO); HRMS-EI(M+): C$_{32}$H$_{37}$N$_3$O$_{10}$S, calcd: 655.2200, found: 655.2174.

Example 16: Preparation of (E)-4-{1-amino-2-[4-t-butoxy-3-(N-methyl-N-phenylcarbamoyloxy)styrylsulfonyl]ethyl}phenyl-2-(4-methoxyphenyl)acetate (Compound P1-3)

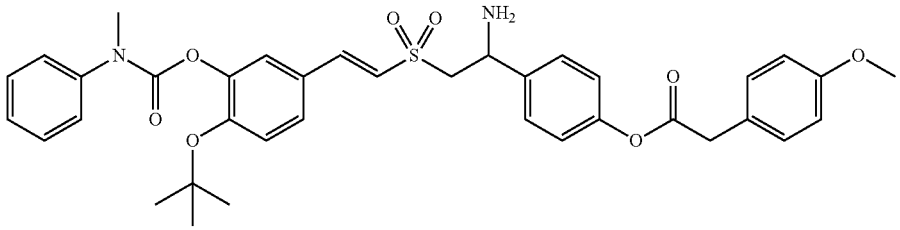

Compound P1-3

With (E)-4-{1-amino-2-[4-t-butoxy-3-hydroxystyrylsulfonyl]ethyl}phenyl-2-(4-methoxyphenyl)acetate as starting material and in accordance with the preparation method in Example 5, Compound P1-3 was prepared by two steps, as a beige yellow solid (yield: 58% over two steps).

Melting point: 146-149° C.

$^1$H NMR (CDCl$_3$) δ:1.36 (brs, 11H, NH$_2$, OC(CH$_3$)$_3$), 3.69 (m, 2H, SO$_2$CH$_a$H$_b$, OCOCH$_a$H$_b$), 3.81 (s, 3H, OCH$_3$), 3.98 (s, 3H, NCH$_3$), 4.11 (m, 2H, SO$_2$CH$_a$H$_b$, OCOCH$_a$H$_b$), 4.59 (m, 1H, NH$_2$CH), 6.84 (d, 2H, J=7.5 Hz, ArH), 6.93 (d, 2H, J=7.4 Hz, ArH), 7.10 (d, 1H, J=7.5 Hz, ArH), 7.18 (m, 3H, CH=CHSO$_2$, ArH), 7.30-7.42 (m, 5H, ArH), 7.55 (d, 2H, J=7.6 Hz, ArH), 7.73 (m, 2H, ArH), 8.09 (d, 1H, J=15.2 Hz, CH=CHSO$_2$); $^{13}$C NMR (CDCl$_3$) δ:28.2 (OC(CH$_3$)$_3$), 34.9 (NCH$_3$), 42.3 (OCOCH$_2$), 52.9 (SO$_2$CH$_2$), 54.6 (NH$_2$CH), 55.8 (OCH$_3$), 81.5 (OC(CH$_3$)$_3$), 112.7 (ArC*2), 116.9 (CH=CHSO$_2$), 120.3 (ArC), 121.9 (ArC*2), 122.2 (ArC*2), 123.5 (ArC), 125.3 (ArC*2), 127.1 (ArC), 128.2 (ArC*2), 128.9 (ArC), 129.7 (ArC*2), 130.8 (ArC*2), 134.9 (CH=CHSO$_2$), 137.8 (ArC), 142.5 (ArC), 143.1 (ArC), 145.9 (ArC), 151.0 (ArC), 154.7 (NCOO), 158.3 (ArC), 170.1 (OCOCH$_2$); HRMS-EI(M+):C$_{37}$H$_{40}$N$_2$O$_8$S, calcd: 672.2505, found: 672.2501.

Example 17: Preparation of (E)-4-{2-[4-(4-dimethylaminobenzyl)phenylbromomethylsulfonyl]ethenyl}-2-[2-(4-dimethylaminophenyl)acetyl]phenyl-2-trifluoromethylpyrrolidine-1-carboxylate (Compound M1-5)

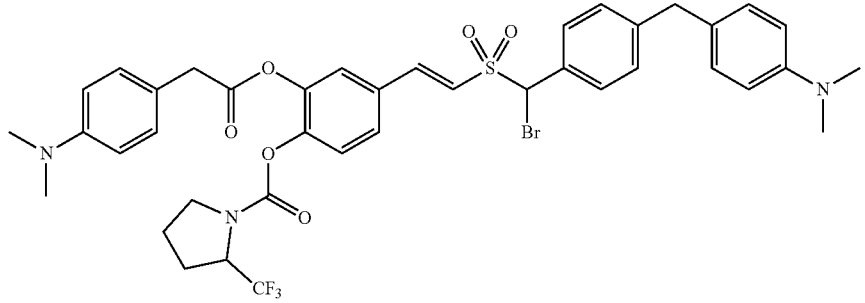

Compound M1-5

With (E)-5-{2-[4-(4-dimethylaminobenzyl)phenylbromomethylsulfonyl]ethenyl}-2-hydroxyphenyl-2-(4-dimethylaminophenyl)acetate as starting material and in accordance with the preparation method in Example 5, Compound M1-5 was prepared by two steps, as a light yellow solid (yield: 44% over two steps).

Melting point: 213-215° C.

$^1$H NMR (CDCl$_3$) δ:1.73-2.01 (m, 4H, NCH$_2$CH$_2$CH$_2$), 2.98 (s, 12H, NCH$_3$*4), 3.16 (m, 1H, NCH$_a$H$_b$), 3.55 (m, 1H, NCH$_a$H$_b$), 3.68 (m, 2H, NCHCF$_3$, CH$_a$H$_b$COO), 3.83 (s, 2H, PhCH$_2$Ph), 4.25 (d, 1H, J=12.5 Hz, CH$_a$H$_b$COO), 6.58 (m, 5H, CHBr, ArH), 6.83 (d, 1H, J=7.5 Hz, ArH), 6.91 (d, 2H, J=7.4 Hz, ArH), 7.13 (d, 1H, J=15.0 Hz, CH=CHSO$_2$), 7.22 (m, 3H, ArH), 7.38 (m, 3H, ArH), 7.63 (d, 2H, J=7.4 Hz, ArH), 8.12 (d, 1H, J=15.1 Hz, CH=CHSO$_2$); $^{13}$C NMR (CDCl$_3$) δ:17.6 (CF$_3$), 24.9 (NCH$_2$CH$_2$), 35.1 (NCH$_2$CH$_2$CH$_2$), 40.5 (CH$_2$COO), 41.2 (NCH$_3$*4), 41.9 (PhCH$_2$Ph), 47.0 (NCH$_2$), 56.4 (NCHCF$_3$), 61.5 (CHBr), 114.0 (ArC*2), 114.5 (ArC*2), 117.6 (CH=CHSO$_2$), 120.9 (ArC), 121.7 (ArC), 125.0 (ArC), 126.3 (ArC), 128.1 (ArC*2), 129.6 (ArC*2), 129.8 (ArC*2), 129.9 (ArC*2), 130.7 (ArC), 131.5 (ArC), 132.5 (ArC), 135.0 (CH=CHSO$_2$), 140.2 (ArC), 142.3 (ArC), 144.0 (ArC), 151.1 (ArC*2), 155.3 (NCOO), 170.4 (CH$_2$COO); HRMS-EI(M+):C$_{40}$H$_{41}$BrF$_3$N$_3$O$_6$S, calcd: 827.1852, found: 827.1829.

Example 18: Preparation of (E)-4-{2-[4-(diethylphenylsiloxy)phenylchloromesyl]ethenyl}-2-(3-chloro-2-methoxybenzoyloxy)phenyl-2,6-dimethylmorpholine-4-carboxylate (Compound R1-5)

With (E)-5-{2-[4-(diethylphenylsiloxy)phenylchloromesyl]ethenyl}-2-hydroxyphenyl-3-chloro-2-methoxybenzoate as starting material and in accordance with the preparation method in Example 5, Compound R1-5 was prepared by two steps, as a yellow solid (yield: 37% over two steps).

Melting point: 167-170° C.

$^1$H NMR (CDCl$_3$) δ:0.78 (m, 4H, SiCH$_2$*2), 1.02 (t, 6H, J=7.9 Hz, SiCH$_2$CH$_3$*2), 1.25 (d, 3H, J=6.8 Hz, CHCH$_3$), 1.34 (d, 3H, J=6.8 Hz, CHCH$_3$), 3.32 (dd, 1H, J=12.5, 6.9 Hz, NCH$_a$H$_b$), 3.41 (dd, 1H, J=12.5, 6.9 Hz, NCH$_a$H$_b$), 3.63 (s, 3H, OCH$_3$), 3.72 (m, 2H, OCHCH$_3$*2), 3.99 (dd, 1H, J=12.5, 6.9 Hz, NCH$_a$H$_b$), 4.08 (dd, 1H, J=12.5, 6.9 Hz, NCH$_a$H$_b$), 6.29 (s, 1H, ClCH), 7.15 (m, 4H, CH=CHSO$_2$, ArH), 7.24-7.43 (m, 8H, ArH), 7.55 (d, 2H, J=7.6 Hz, ArH), 7.61 (dd, 1H, J=7.5, 1.7 Hz, ArH), 7.73 (dd, 1H, J=7.3, 2.0 Hz, ArH), 8.10 (d, 1H, J=15.0 Hz, CH=CHSO$_2$); $^{13}$C NMR (CDCl$_3$) δ:6.9 (SiCH$_2$CH$_3$*2), 11.2 (SiCH$_2$CH$_3$*2), 18.9 (OCHCH$_3$*2), 52.1 (NCH$_2$*2), 62.8 (OCH$_3$), 71.4 (OCHCH$_3$*2), 79.5 (ClCH), 120.1 (ArC), 121.5 (ArC*2), 121.8 (ArC), 123.5 (ArC), 124.6 (ArC), 124.9 (ArC), 125.3 (ArC), 125.8 (CH=CHSO$_2$), 126.1 (ArC*2), 127.9 (ArC), 130.2 (ArC*2), 130.4 (ArC), 131.1 (ArC), 132.5 (ArC), 134.1 (ArC), 134.6 (ArC*2), 140.2 (ArC), 142.3 (ArC), 144.0 (ArC), 152.8 (ArC), 154.0 (NCOO), 155.7 (CH=CHSO$_2$), 159.2 (ArC), 167.3 (ArCOO); HRMS-EI (M+):C$_{40}$H$_{43}$Cl$_2$NO$_9$SSi, calcd: 811.1805, found: 811.1788.

Example 19: Preparation of (E)-2-[N-(3-methyl-4-nitrobenzoyl)carbamoyloxy]-4-{2-[(perfluorophenyl)mesyl]ethenyl}phenyl acetate (Compound D5-4)

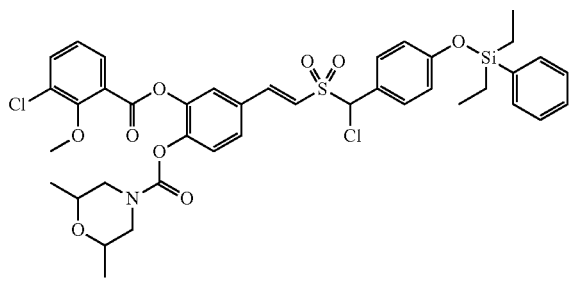

Compound R1-5

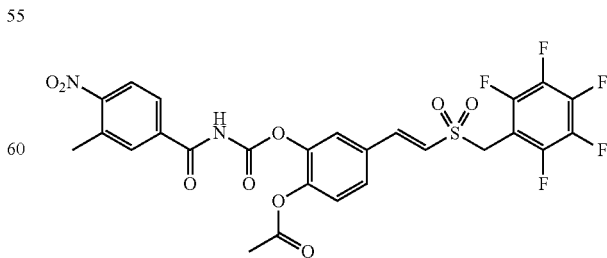

Compound D5-4

With (E)-2-hydroxy-4-{2-[(perfluorophenyl)mesyl]ethenyl}phenyl acetate as starting material and in accordance with the preparation method in Example 5, Compound D5-4 was prepared by two steps, as a yellow solid (yield: 42% over two steps).

Melting point: 264-267° C.

$^1$H NMR (CDCl$_3$) δ:2.32 (s, 3H, Ph-C$\underline{H}_3$), 2.54 (s, 3H, C$\underline{H}_3$CO), 4.69 (s, 2H, SO$_2$C$\underline{H}_2$), 5.50 (brs, 1H, CONH), 7.01 (d, 1H, J=7.5 Hz, ArH), 7.09 (s, 1H, ArH), 7.18 (d, 1H, J=15.2 Hz, CH=C$\underline{H}$SO$_2$), 7.23 (d, 1H, J=7.5 Hz, ArH), 7.49 (m, 2H, ArH), 7.58 (dd, 1H, J=7.5, 2.0 Hz, ArH), 8.13 (d, 1H, J=15.2 Hz, C$\underline{H}$=CHSO$_2$); $^{13}$C NMR (CDCl$_3$) δ:19.9 (Ph-$\underline{C}$H$_3$), 20.8 ($\underline{C}$H$_3$CO), 56.1 (SO$_2$$\underline{C}$H$_2$), 105.3 (ArC), 118.6 (CH=$\underline{C}$HSO$_2$), 122.3 (ArC), 123.1 (ArC), 125.2 (ArC), 127.6 (ArC), 129.1 (ArC), 130.4 (ArC), 130.6 (ArC), 133.5 (ArC), 134.8 ($\underline{C}$H=CHSO$_2$), 136.7 (ArC), 137.8 (ArC), 138.8 (ArC), 141.7 (ArC), 142.2 (ArC*2), 143.1 (ArC), 144.0 (ArC), 145.8 (ArC), 152.4 (NHCOO), 165.7 (CONHCOO), 169.1 (CH$_3$$\underline{C}$O); HRMS-EI(M+): C$_{26}$H$_{17}$F$_5$N$_2$O$_9$S, calcd: 628.0575, found: 628.0553.

Example 20: Preparation of (E)-4-{[4-(ethylsulfonyloxy)-3-(N-methyl-N-mesylaminomesyloxy)styrylsulfonyl]methyl}phenylesilate (Compound S1-6)

With (E)-4-{[4-(ethylsulfonyloxy)-3-hydroxystyrylsulfonyl]methyl}phenylesilate as starting material and in accordance with the preparation method in Example 5, Compound S1-6 was prepared by two steps, as a light yellow solid (yield: 29% over two steps).

Melting point: 255-257° C.

$^1$H NMR (CDCl$_3$) δ:1.41 (t, 3H, J=8.1 Hz, C$\underline{H}_3$CH$_2$SO$_2$), 1.53 (t, 3H, J=8.0 Hz, C$\underline{H}_3$CH$_2$SO$_2$), 2.75 (s, 3H, CH$_3$N), 2.92 (s, 3H, CH$_3$SO$_2$), 3.07 (q, 4H, J=8.0 Hz, CH$_3$C$\underline{H}_2$SO$_2$*2), 4.68 (s, 2H, SO$_2$C$\underline{H}_2$Ph), 7.15 (d, 1H, J=15.1 Hz, CH=C$\underline{H}$SO$_2$), 7.25 (m, 2H, ArH), 7.38 (d, 1H, J=7.6 Hz, ArH), 7.44 (d, 2H, J=7.5 Hz, ArH), 7.67 (d, 2H, J=7.4 Hz, ArH), 8.10 (d, 1H, J=15.2 Hz, C$\underline{H}$=CHSO$_2$); $^{13}$C NMR (CDCl$_3$) δ:8.5 ($\underline{C}$H$_3$CH$_2$SO$_2$*2), 31.5 (CH$_3$N), 42.3 (CH$_3$SO$_2$), 45.7 (CH$_3$$\underline{C}$H$_2$SO$_2$*2), 59.3 (SO$_2$$\underline{C}$H$_2$Ph), 118.8 (CH=$\underline{C}$HSO$_2$), 120.6 (ArC), 122.3 (ArC), 123.5 (ArC*2), 125.0 (ArC), 126.9 (ArC), 127.6 (ArC*2), 128.1 (ArC), 134.8 ($\underline{C}$H=CHSO$_2$), 141.5 (ArC), 146.3 (ArC), 148.6 (ArC), 150.2 (NCOO); HRMS-EI(M+):C$_{22}$H$_{27}$NO$_{12}$S$_4$, calcd: 625.0416, found: 625.0404.

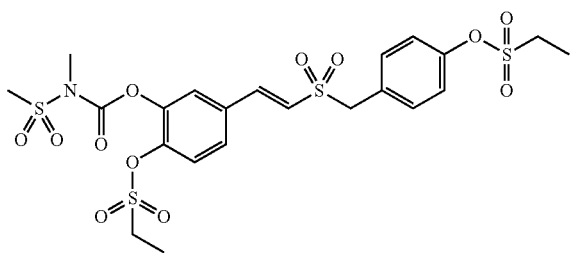

Compound S1-6

Example 21: Preparation of (E)-2-(N-methyl-N-p-tosylcarbamoyloxy)-4-{2-[(4-p-tosyloxyphenyl)mesyl]ethenyl}phenyl p-toluenesulfonate (Compound S6-6)

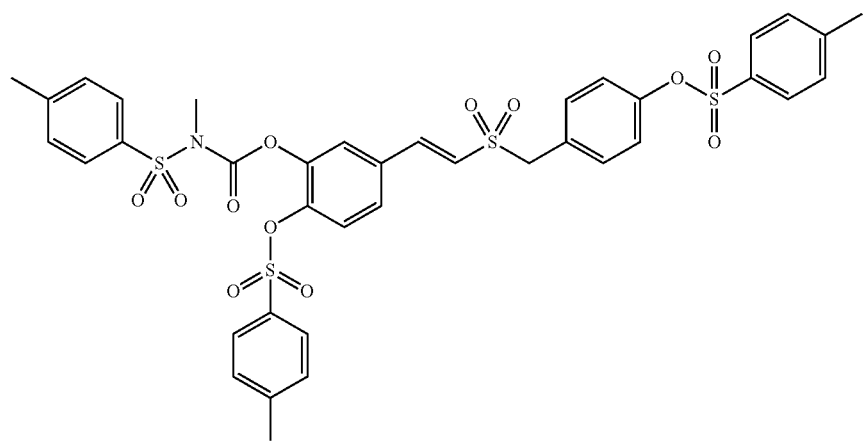

Compound S6-6

With (E)-2-hydroxy-4-{2-[(4-p-tosyloxyphenyl)mesyl]ethenyl}phenyl p-toluenesulfonate as starting material and in accordance with the preparation method in Example 5, Compound S6-6 was prepared by two steps, as a beige white solid product (yield: 47% over two steps).

Melting point: 271-274° C.

$^1$H NMR (CDCl$_3$) δ:2.42 (s, 9H, C$\underline{H}_3$Ph*3), 3.03 (s, 3H, C$\underline{H}_3$N), 4.68 (s, 2H, SO$_2$C$\underline{H}_2$Ph), 7.11 (m, 1H, ArH), 7.15-7.23 (m, 4H, C$\underline{H}$=CHSO$_2$, ArH), 7.26-7.35 (m, 5H, ArH), 7.48 (m, 4H, ArH), 7.73 (m, 4H, ArH), 8.01 (d, 2H, J=7.6 Hz, ArH), 8.11 (d, 1H, J=15.3 Hz, C$\underline{H}$=CHSO$_2$); $^{13}$C NMR (CDCl$_3$) δ:21.5 ($\underline{C}$H$_3$Ph*3), 32.6 ($\underline{C}$H$_3$N), 59.5 (SO$_2$$\underline{C}$H$_2$Ph), 119.3 ($\underline{C}$H=CHSO$_2$), 121.3 (ArC), 122.0 (ArC), 124.1 (ArC), 124.6 (ArC*2), 126.5 (ArC), 127.9 (ArC*2), 128.6 (ArC*2), 128.8 (ArC*2), 128.9 (ArC), 129.3 (ArC*2), 129.5 (ArC*2), 130.1 (ArC*4), 134.6 ($\underline{C}$H=CHSO$_2$), 136.3 (ArC), 136.8 (ArC), 137.2 (ArC), 140.4 (ArC*2), 142.1 (ArC), 143.0 (ArC), 144.5 (ArC), 146.9 (ArC), 149.9 (NCOO); HRMS-EI(M+): C$_{38}$H$_{35}$NO$_{12}$S$_4$, calcd: 825.1042, found: 825.1019.

Example 22: Preparation of (E)-4-{2-[4-(dimethylamino)-4-(4-(N,N-dimethylglycyloxy)phenyl)butylsulfonyl]ethenyl}-2-(N-methyl-N-phenylcarbamoyloxy)phenyl-4-(p-methylphenyl)piperazine-1-carboxylate (Compound P1-1)

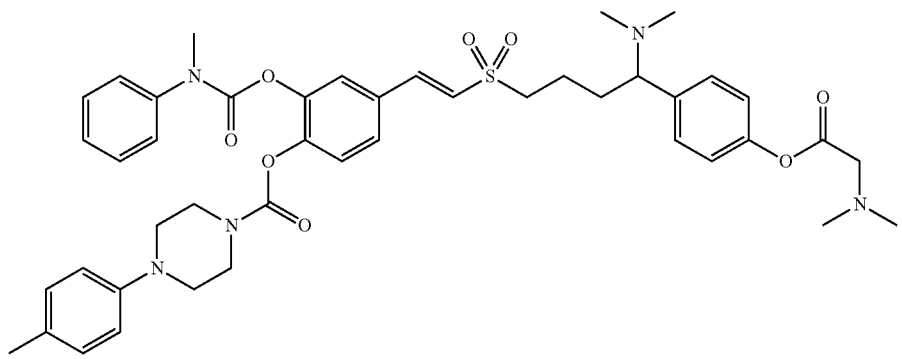

Compound P1-1

With (E)-4-{4-[(3,4-dihydroxystyryl)sulfonyl]-1-(dimethylamino)butyl}phenyl-N,N-dimethylglycinate as starting material and in accordance with the preparation method in Example 5, (E)-4-{2-[4-(dimethylamino)-4-(4-(N,N-dimethylglycyloxy)phenyl)butylsulfonyl]ethenyl}-2-hydroxyphenyl-4-(p-methylphenyl)piperazine-1-carboxylate (Compound P1-1-a) was prepared by two steps (yield: 26% over two steps); then using Compound P1-1-a as starting material and in accordance with the preparation method in Example 5, Compound P1-1 was prepared by two steps, as a light yellow solid (yield: 43% over two steps).

Melting point: 271-274° C.

$^1$H NMR (CDCl$_3$) δ:1.44 (m, 1H, NCHC$\underline{H}_a$H$_b$), 1.77 (m, 1H, SO$_2$CH$_2$C$\underline{H}_a$H$_b$), 2.03 (m, 1H, SO$_2$CH$_2$CH$_a$$\underline{H}_b$), 2.24 (s, 3H, CHNC$\underline{H}_3$), 2.27 (s, 3H, CHNC$\underline{H}_3$), 2.32 (s, 3H, C$\underline{H}_3$Ph), 2.39 (s, 3H, C$\underline{H}_3$NCH$_2$), 2.48 (s, 3H, C$\underline{H}_3$NCH$_2$), 2.85 (m, 1H, SO$_2$C$\underline{H}_a$H$_b$), 2.99-3.08 (m, 3H, NCHCH$_a$$\underline{H}_b$, CH$_a$$\underline{H}_b$NCO, SO$_2$CH$_a$$\underline{H}_b$), 3.18-3.30 (m, 3H, ArNC$\underline{H}_a$H$_b$*2, COC$\underline{H}_a$H$_b$N), 3.39-3.43 (m, 2H, ArC$\underline{H}$N, C$\underline{H}_a$H$_b$NCO), 3.59 (s, 3H, PhNC$\underline{H}_3$), 3.72 (m, 2H, ArNCH$_a$$\underline{H}_b$, COCH$_a$$\underline{H}_b$N), 3.88 (m, 1H, CH$_a$$\underline{H}_b$NCO), 4.17 (m, 1H, ArNCH$_a$$\underline{H}_b$), 4.33 (m, 1H, CH$_a$$\underline{H}_b$NCO), 6.63 (d, 2H, J=7.5 Hz, ArH), 6.95 (d, 2H, J=7.5 Hz, ArH), 7.03 (m, 0.3H, ArH), 7.05 (s, 1H, ArH), 7.16 (d, 1H, J=15.2 Hz, CH=C$\underline{H}$SO$_2$), 7.22 (m, 1H, ArH), 7.31-7.37 (m, 3H, ArH), 7.40 (d, 2H, J=7.4 Hz, ArH), 7.49 (dd, 2H, J=7.5, 2.0 Hz, ArH), 8.15 (d, 1H, J=15.2 Hz, C$\underline{H}$=CHSO$_2$); $^{13}$C NMR (CDCl$_3$) δ:18.9 (SO$_2$CH$_2$$\underline{C}$H$_2$), 21.0 ($\underline{C}$H$_3$Ph), 32.6 ($\underline{C}$H$_2$CHN), 35.7 (PhN$\underline{C}$H$_3$), 42.7 (CHN($\underline{C}$H$_3$)$_2$), 45.8 (CON($\underline{C}$H$_2$)$_2$), 46.5 (ArN($\underline{C}$H$_2$)$_2$), 47.2 (CH$_2$N($\underline{C}$H$_3$)$_2$), 55.1 (SO$_2$$\underline{C}$H$_2$), 60.6 (CO$\underline{C}$H$_2$N), 72.1 (Ar$\underline{C}$HN), 112.9 (ArC*2), 119.3 (CH=$\underline{C}$HSO$_2$), 120.8 (ArC), 121.5 (ArC), 121.8 (ArC*2), 122.3 (ArC*2), 125.0 (ArC), 125.5 (ArC), 127.3 (ArC), 128.6 (ArC*2), 129.1 (ArC), 129.4 (ArC*2), 130.1 (ArC*2), 135.6 ($\underline{C}$H=CHSO$_2$), 137.5 (ArC), 140.1 (ArC), 141.3 (ArC), 143.2 (ArC), 149.0 (ArC), 149.5 (ArC), 152.3 (CH$_2$N$\underline{C}$OO), 154.7 (CH$_3$N$\underline{C}$OO), 168.3 (CH$_2$$\underline{C}$OO); HRMS-EI(M+):C$_{44}$H$_{53}$N$_5$O$_8$S, calcd: 811.3615, found: 811.3652.

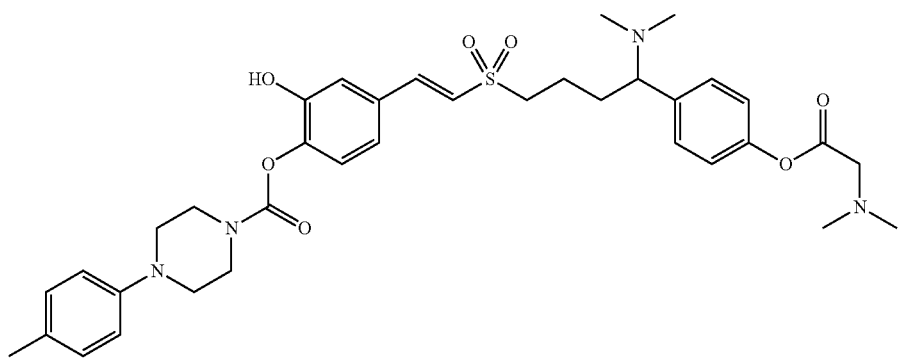

Compound P1-1-a

Example 23: Evaluation of the Inhibitory Activity of the Target Compounds on the Damage from Parkinson's Disease in Fetal Rat Midbrain Neurons (Using the Survival Rate of Primary Midbrain Neurons Induced by MPP+ as the Evaluation Indicator)

1. Experiment Principle

The main pathological feature of Parkinson's disease (PD) lies in the degeneration and loss of dopaminergic neuron in the substantia nigra-striatum of the midbrain. 1-Methyl-4-phenylpyridinium (MPP+) has a high affinity to dopamine carriers and a selective toxicity on dopaminergic neurons. Thus, MPP+ is one of the most ideal classic neurotoxins for establishing PD cell models. The primary cell culture of fetal rat midbrain is often used to establish PD cell models in recent years. Although it is more cumbersome and has higher technical requirements than cell line culture, it is closer to the pathological characteristics of PD. Thus, a PD cell model is established using neurons from the primary cell culture of fetal rat midbrain under MPP+ induction, to evaluate the protective effect of target compounds on the model neurons.

2. Experiment Method

The midbrain was separated from a fetal rat of a 15-day-pregnant SD rat and cut into pieces, then subjected to trypsin digestion, pipetting, screen filtration, and resuspension steps, and inoculated in a 24-well cell culture plate pre-coated with poly-D-lysine. 12 hours after culture, cytarabine was added to inhibit the growth of glial cells. On the $5^{th}$ day of neuron growth, the toxin MPP+ can be added to make a PD cell model. When detecting the activity of a target compound, the target compound was pre-incubated with midbrain neurons for 3 h, then MPP+ was added, and after 48 h co-incubation the neuronal viability was detected by CCK-8 method and the neuronal survival rate was calculated to evaluate the inhibitory activity of the target compound on the midbrain neuronal PD damage. The experiment included blank control group, MPP+ model group, positive control group (caffeic acid phenethyl ester, CAPE), prototype control group (styryl sulfone compounds 3B, 3C, 3D, and 3G), and target compound group (prepared according to Examples 1-22 in the invention).

Among them, the prototype control group has a structure formula as follows:

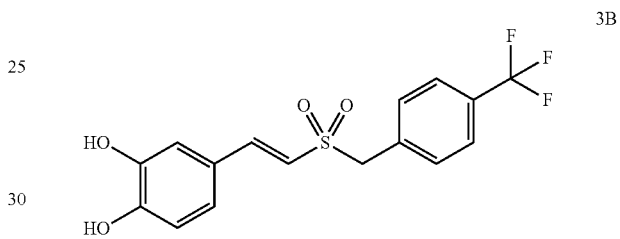

3B

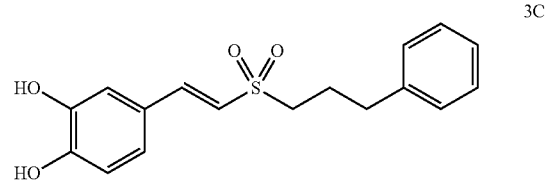

3C

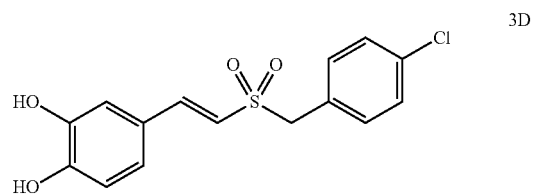

3D

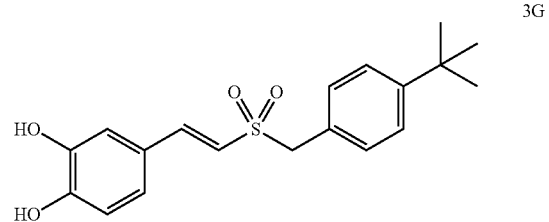

3G

3. Experiment Results

The effect of each group on the primary midbrain neuron damage induced by MPP+ is shown in the table below:

| Group | Con. (μM) | Survival rate (%) | Compared with the model group | Compared with the positive group* | Compared with the prototype group** |
|---|---|---|---|---|---|
| Blank control group | / | 100 ± 1.53 | / | / | / |
| MPP+ model group | / | 48.92 ± 2.19 | / | / | / |
| Positive control group | 5 | 54.97 ± 3.78 | Increased, P < 0.05 | / | / |
| | 10 | 67.08 ± 2.98 | Increased, P < 0.01 | / | / |
| | 20 | 82.56 ± 2.13 | Increased, P < 0.01 | / | / |
| Prototype control group 3B | 5 | 65.94 ± 1.47 | Increased, P < 0.01 | Increased, P < 0.01 | / |
| | 10 | 76.41 ± 6.54 | Increased, P < 0.01 | Increased, P < 0.05 | / |
| | 20 | 84.92 ± 2.65 | Increased, P < 0.01 | Equivalent, P > 0.05 | / |
| Prototype control group 3C | 5 | 61.33 ± 3.22 | Increased, P < 0.01 | Increased, P < 0.05 | / |
| | 10 | 75.69 ± 1.98 | Increased, P < 0.01 | Increased, P < 0.01 | / |
| | 20 | 74.25 ± 4.55 | Increased, P < 0.01 | Decreased, P < 0.01 | / |
| Prototype control group 3D | 5 | 69.54 ± 5.21 | Increased, P < 0.01 | Increased, P < 0.01 | / |
| | 10 | 84.1 ± 1.87 | Increased, P < 0.01 | Increased, P < 0.01 | / |
| | 20 | 91.49 ± 2.32 | Increased, P < 0.01 | Increased, P < 0.01 | / |
| Prototype control group 3G | 5 | 51.38 ± 3.54 | Equivalent, P > 0.05 | Equivalent, P > 0.05 | / |
| | 10 | 68.41 ± 1.89 | Increased, P < 0.01 | Equivalent, P > 0.05 | / |
| | 20 | 71.18 ± 3.75 | Increased, P < 0.01 | Decreased, P < 0.01 | / |
| Group B1-1 | 5 | 78.46 ± 4.12 | Increased, P < 0.01 | Increased, P < 0.01 | Increased, P < 0.01 |
| | 10 | 89.74 ± 2.89 | Increased, P < 0.01 | Increased, P < 0.01 | Increased, P < 0.01 |
| | 20 | 93.85 ± 1.59 | Increased, P < 0.01 | Increased, P < 0.01 | Increased, P < 0.01 |
| Group C1-1 | 5 | 69.54 ± 3.89 | Increased, P < 0.01 | Increased, P < 0.01 | Increased, P < 0.01 |
| | 10 | 82.15 ± 3.07 | Increased, P < 0.01 | Increased, P < 0.01 | Increased, P < 0.01 |
| | 20 | 90.33 ± 2.17 | Increased, P < 0.01 | Increased, P < 0.01 | Increased, P < 0.01 |
| Group D1-1 | 5 | 80.31 ± 2.67 | Increased, P < 0.01 | Increased, P < 0.01 | Increased, P < 0.01 |
| | 10 | 94.56 ± 3.76 | Increased, P < 0.01 | Increased, P < 0.01 | Increased, P < 0.01 |
| | 20 | 97.95 ± 1.32 | Increased, P < 0.01 | Increased, P < 0.01 | Increased, P < 0.01 |
| Group G1-1 | 5 | 78.53 ± 3.59 | Increased, P < 0.01 | Increased, P < 0.01 | Increased, P < 0.01 |
| | 10 | 85.94 ± 2.67 | Increased, P < 0.01 | Increased, P < 0.01 | Increased, P < 0.01 |
| | 20 | 91.44 ± 1.59 | Increased, P < 0.01 | Increased, P < 0.01 | Increased, P < 0.01 |
| Group E2-2 | 5 | 58.13 ± 4.27 | Increased, P < 0.01 | Equivalent, P > 0.05 | / |
| | 10 | 69.29 ± 2.33 | Increased, P < 0.01 | Equivalent, P > 0.05 | / |
| | 20 | 86.12 ± 2.06 | Increased, P < 0.01 | Increased, P < 0.05 | / |
| Group K3-3 | 5 | 62.51 ± 3.58 | Increased, P < 0.01 | Equivalent, P < 0.05 | / |
| | 10 | 75.46 ± 2.37 | Increased, P < 0.01 | Increased, P < 0.01 | / |
| | 20 | 88.45 ± 1.73 | Increased, P < 0.01 | Increased, P < 0.01 | / |
| Group K1-4 | 5 | 76.71 ± 3.17 | Increased, P < 0.01 | Increased, P < 0.01 | / |
| | 10 | 87.13 ± 2.56 | Increased, P < 0.01 | Increased, P < 0.01 | / |
| | 20 | 93.22 ± 1.81 | Increased, P < 0.01 | Increased, P < 0.01 | / |
| Group P1-7 | 5 | 79.23 ± 3.72 | Increased, P < 0.01 | Increased, P < 0.01 | / |
| | 10 | 86.63 ± 2.93 | Increased, P < 0.01 | Increased, P < 0.01 | / |
| | 20 | 91.17 ± 2.08 | Increased, P < 0.01 | Increased, P < 0.01 | / |
| Group H2-4 | 5 | 68.95 ± 4.31 | Increased, P < 0.01 | Increased, P < 0.01 | / |
| | 10 | 81.53 ± 3.24 | Increased, P < 0.01 | Increased, P < 0.01 | / |
| | 20 | 89.37 ± 1.65 | Increased, P < 0.01 | Increased, P < 0.01 | / |
| Group M1-3 | 5 | 76.51 ± 4.82 | Increased, P < 0.01 | Increased, P < 0.01 | / |
| | 10 | 85.29 ± 2.97 | Increased, P < 0.01 | Increased, P < 0.01 | / |
| | 20 | 93.26 ± 2.26 | Increased, P < 0.01 | Increased, P < 0.01 | / |
| Group L1-4 | 5 | 67.49 ± 3.52 | Increased, P < 0.01 | Increased, P < 0.01 | / |
| | 10 | 75.37 ± 2.59 | Increased, P < 0.01 | Increased, P < 0.01 | / |
| | 20 | 86.18 ± 1.86 | Increased, P < 0.01 | Increased, P < 0.05 | / |
| Group K1-3 | 5 | 65.39 ± 4.31 | Increased, P < 0.01 | Increased, P < 0.01 | / |
| | 10 | 72.08 ± 2.77 | Increased, P < 0.01 | Increased, P < 0.05 | / |
| | 20 | 83.19 ± 1.76 | Increased, P < 0.01 | Equivalent, P > 0.05 | / |
| Group J1-4 | 5 | 75.23 ± 3.29 | Increased, P < 0.01 | Increased, P < 0.01 | / |
| | 10 | 84.79 ± 2.27 | Increased, P < 0.01 | Increased, P < 0.01 | / |
| | 20 | 90.34 ± 2.60 | Increased, P < 0.01 | Increased, P < 0.01 | / |
| Group A1-3 | 5 | 74.32 ± 3.75 | Increased, P < 0.01 | Increased, P < 0.01 | / |
| | 10 | 89.74 ± 1.95 | Increased, P < 0.01 | Increased, P < 0.01 | / |
| | 20 | 94.07 ± 1.87 | Increased, P < 0.01 | Increased, P < 0.01 | / |
| Group M1-1 | 5 | 82.36 ± 2.54 | Increased, P < 0.01 | Increased, P < 0.01 | / |
| | 10 | 89.93 ± 3.67 | Increased, P < 0.01 | Increased, P < 0.01 | / |
| | 20 | 95.07 ± 1.94 | Increased, P < 0.01 | Increased, P < 0.01 | / |
| Group P1-3 | 5 | 71.02 ± 3.56 | Increased, P < 0.01 | Increased, P < 0.01 | / |
| | 10 | 85.24 ± 2.94 | Increased, P < 0.01 | Increased, P < 0.01 | / |
| | 20 | 93.66 ± 3.08 | Increased, P < 0.01 | Increased, P < 0.01 | / |
| Group M1-5 | 5 | 68.16 ± 4.31 | Increased, P < 0.01 | Increased, P < 0.01 | / |
| | 10 | 78.24 ± 3.76 | Increased, P < 0.01 | Increased, P < 0.01 | / |
| | 20 | 86.91 ± 3.08 | Increased, P < 0.01 | Increased, P < 0.05 | / |
| Group R1-5 | 5 | 72.28 ± 2.94 | Increased, P < 0.01 | Increased, P < 0.01 | / |
| | 10 | 82.51 ± 2.83 | Increased, P < 0.01 | Increased, P < 0.01 | / |
| | 20 | 90.17 ± 1.76 | Increased, P < 0.01 | Increased, P < 0.01 | / |
| Group D5-4 | 5 | 60.45 ± 3.19 | Increased, P < 0.01 | Equivalent, P > 0.05 | / |
| | 10 | 73.18 ± 4.53 | Increased, P < 0.01 | Increased, P < 0.05 | / |
| | 20 | 87.46 ± 2.16 | Increased, P < 0.01 | Increased, P < 0.01 | / |

-continued

| Group | Con. (μM) | Survival rate (%) | Changes and statistical difference (P value) | | |
|---|---|---|---|---|---|
| | | | Compared with the model group | Compared with the positive group* | Compared with the prototype group** |
| Group S1-6 | 5 | 80.25 ± 5.19 | Increased, P < 0.01 | Increased, P < 0.01 | / |
| | 10 | 87.53 ± 3.61 | Increased, P < 0.01 | Increased, P < 0.01 | / |
| | 20 | 93.29 ± 3.07 | Increased, P < 0.01 | Increased, P < 0.01 | / |
| Group S6-6 | 5 | 71.96 ± 2.47 | Increased, P < 0.01 | Increased, P < 0.01 | / |
| | 10 | 83.16 ± 4.07 | Increased, P < 0.01 | Increased, P < 0.01 | / |
| | 20 | 91.72 ± 3.18 | Increased, P < 0.01 | Increased, P < 0.01 | / |
| Group P1-1 | 5 | 75.35 ± 3.12 | Increased, P < 0.01 | Increased, P < 0.01 | / |
| | 10 | 86.59 ± 2.39 | Increased, P < 0.01 | Increased, P < 0.01 | / |
| | 20 | 92.17 ± 3.05 | Increased, P < 0.01 | Increased, P < 0.01 | / |

*Comparison with the data of the positive drug control group at an equal concentration
**Only four groups of compounds (B1-1, C1-1, D1-1, and G1-1) were compared with the prototype compounds of corresponding structures (i.e., styryl sulfones 3B, 3C, 3D, and 3G)

It can be seen that compared with the model group, all the compounds showed a statistically significant increase in the survival rate, demonstrating that these compounds have a definite protective effect on the primary midbrain neuron damage induced by MPP+. Compared with the positive control CAPE, most of the compounds had a relatively significant or significant increase in the survival rate, demonstrating that the protective effect on the primary midbrain neuron damage inducted by MPP+ of these compounds were stronger than that of the positive control CAPE. The survival rates of the four groups of compounds B1-1, C1-1, D1-1, and G1-1 were significantly increased compared with those of the styryl sulfone prototype compounds 3B, 3C, 3D), and 3G, demonstrating that compared with the prototype compounds without the introduction of carbamate functional group, the protective effect on the primary midbrain neuron damage induced by MPP+ of these compounds was significantly enhanced.

Example 24: Evaluation of the Inhibitory Activity of the Target Compounds on the Inflammatory Response in Glial Cells (Inhibition of the NO Release of Primary Glial Cells Induced by LPS, Using the NO Content in the Cell Culture Medium as the Evaluation Indicator)

1. Experiment Principle

Lipopolysaccharide (LPS) is a main component of the cell wall of Gram-negative bacteria. It is a potent inflammatory factor that can directly activate gliocytes, and the activated gliocytes secrete a large amount of inflammation mediators such as tumor necrosis factor, interleukin, and nitric oxide, thus causing inflammatory reactions and oxidative stress reactions and eventually leading to neuronal denaturation and death. In recent years, the targeted injection of LPS into rat substantia nigra or striatum to induce neuroinflammation can successfully establish PD models, which can simulate most of the clinical manifestations and pathological features of PD, and are used for the study on the neuroinflammation mechanism associated with PD. LPS-induced primary glial cell PD inflammation model is suitable for the preliminary anti-neuroinflammation screening for neuroprotective agents. LPS is used to directly activate primary glial cells to simulate the pathogenesis mechanism of neuroinflammation, and the inhibitory activity of the target compounds on the inflammatory response of primary glial cells can be investigated.

2. Experiment Method

The materials were taken from the brain tissue of fetal rat, for primary glial cell culture. At 7 to 10 days of the culture, LPS was added for the activation of nitric oxide (NO) release in glial cells. When a target compound was added, the reduction value for NO content in the cell culture medium was measured, to evaluate the anti-neuroinflammation activity of the compound. The experiment included blank control group, LPS model group, positive control group (caffeic acid phenethyl ester, CAPE), prototype control group (styryl sulfone compounds 3B, 3C, 3D, and 3G, the structures of which compounds are shown as above), and target compound group.

3. Experiment Results

The inhibitory effect of each group on the NO release of primary glial cells induced by LPS is shown in the table below:

| Group* | Con. (μM) | NO inhibition (%) | Changes and statistical difference (P value)** | |
|---|---|---|---|---|
| | | | Compared with the positive group | Compared with the prototype group |
| Positive control group | 2 | 31.52 ± 5.43 | / | / |
| | 5 | 45.23 ± 3.85 | / | / |
| | 10 | 77.08 ± 4.37 | / | / |
| Prototype control group 3B | 5 | 17.18 ± 4.56 | Decreased, P < 0.05 | / |
| | 10 | 38.58 ± 2.13 | Decreased, P < 0.05 | / |
| | 20 | 92.02 ± 3.01 | / | / |
| Prototype control group 3C | 5 | 9.24 ± 4.88 | Decreased, P < 0.05 | / |
| | 10 | 24.56 ± 3.09 | Decreased, P < 0.05 | / |
| | 20 | 45.76 ± 5.25 | / | / |
| Prototype control group 3D | 2 | 23.48 ± 8.05 | Equivalent, P > 0.05 | / |
| | 5 | 34.65 ± 4.89 | Decreased, P < 0.05 | / |
| | 10 | 74.72 ± 3.32 | Equivalent, P > 0.05 | / |

-continued

| Group* | Con. (μM) | NO inhibition (%) | Changes and statistical difference (P value)** Compared with the positive group | Compared with the prototype group |
|---|---|---|---|---|
| Prototype control group 3G | 5 | 41.20 ± 3.01 | Equivalent, P > 0.05 | / |
|  | 10 | 59.56 ± 2.44 | Decreased, P < 0.05 | / |
|  | 20 | 85.78 ± 3.88 | / | / |
| Group B1-1 | 5 | 21.58 ± 2.18 | Decreased, P < 0.05 | Equivalent, P > 0.05 |
|  | 10 | 42.75 ± 3.56 | Decreased, P < 0.05 | Equivalent, P > 0.05 |
|  | 20 | 97.65 ± 2.04 | / | Increased, P < 0.05 |
| Group C1-1 | 5 | 17.58 ± 3.24 | Decreased, P < 0.05 | Increased, P < 0.05 |
|  | 10 | 32.75 ± 5.25 | Decreased, P < 0.05 | Increased, P < 0.05 |
|  | 20 | 59.45 ± 4.33 | / | Increased, P < 0.05 |
| Group D1-1 | 2 | 24.78 ± 4.08 | Equivalent, P > 0.05 | Equivalent, P > 0.05 |
|  | 5 | 61.38 ± 2.77 | Increased, P < 0.05 | Increased, P < 0.05 |
|  | 10 | 84.54 ± 7.56 | Equivalent, P > 0.05 | Increased, P < 0.05 |
| Group G1-1 | 2 | 27.20 ± 3.98 | Equivalent, P > 0.05 | / |
|  | 5 | 64.23 ± 3.25 | Increased, P < 0.05 | Increased, P < 0.05 |
|  | 10 | 85.77 ± 5.01 | Increased, P < 0.05 | Increased, P < 0.05 |
| Group E2-2 | 5 | 20.27 ± 4.73 | Decreased, P < 0.05 | / |
|  | 10 | 36.78 ± 6.11 | Decreased, P < 0.05 | / |
|  | 20 | 68.93 ± 3.75 | / | / |
| Group K3-3 | 5 | 17.58 ± 3.24 | Decreased, P < 0.05 | / |
|  | 10 | 40.62 ± 3.11 | Decreased, P < 0.05 | / |
|  | 20 | 72.48 ± 6.08 | / | / |
| Group K1-4 | 2 | 30.18 ± 4.01 | Equivalent, P > 0.05 | / |
|  | 5 | 53.48 ± 5.52 | Increased, P < 0.05 | / |
|  | 10 | 77.41 ± 5.09 | Equivalent, P > 0.05 | / |
| Group P1-7 | 5 | 21.26 ± 4.43 | Decreased, P < 0.05 | / |
|  | 10 | 41.22 ± 1.95 | Decreased, P < 0.05 | / |
|  | 20 | 70.95 ± 3.67 | / | / |
| Group H2-4 | 2 | 32.18 ± 4.49 | Equivalent, P > 0.05 | / |
|  | 5 | 50.08 ± 5.37 | Equivalent, P > 0.05 | / |
|  | 10 | 85.41 ± 4.90 | Increased, P < 0.05 | / |
| Group M1-3 | 2 | 23.93 ± 4.67 | Decreased, P < 0.05 | / |
|  | 5 | 47.42 ± 4.43 | Equivalent, P > 0.05 | / |
|  | 10 | 73.41 ± 4.83 | Equivalent, P > 0.05 | / |
| Group L1-4 | 2 | 26.73 ± 6.93 | Equivalent, P > 0.05 | / |
|  | 5 | 50.92 ± 3.72 | Increased, P < 0.05 | / |
|  | 10 | 72.27 ± 4.80 | Equivalent, P > 0.05 | / |
| Group K1-3 | 5 | 33.26 ± 6.71 | Decreased, P < 0.05 | / |
|  | 10 | 54.19 ± 4.06 | Decreased, P < 0.05 | / |
|  | 20 | 81.36 ± 4.29 | / | / |
| Group J1-4 | 2 | 24.81 ± 5.02 | Equivalent, P > 0.05 | / |
|  | 5 | 40.92 ± 3.94 | Equivalent, P > 0.05 | / |
|  | 10 | 69.67 ± 5.85 | Equivalent, P > 0.05 | / |
| Group A1-3 | 5 | 19.58 ± 3.67 | Decreased, P < 0.05 | / |
|  | 10 | 43.17 ± 2.36 | Decreased, P < 0.05 | / |
|  | 20 | 62.09 ± 4.73 | / | / |
| Group M1-1 | 2 | 38.26 ± 3.42 | Increased, P < 0.05 | / |
|  | 5 | 52.92 ± 5.36 | Increased, P < 0.05 | / |
|  | 10 | 82.67 ± 2.47 | Increased, P < 0.05 | / |
| Group P1-3 | 5 | 25.78 ± 4.25 | Decreased, P < 0.05 | / |
|  | 10 | 41.96 ± 5.34 | Decreased, P < 0.05 | / |
|  | 20 | 58.23 ± 3.66 | / | / |
| Group M1-5 | 5 | 21.19 ± 3.12 | Decreased, P < 0.05 | / |
|  | 10 | 45.63 ± 4.28 | Decreased, P < 0.05 | / |
|  | 20 | 66.73 ± 4.02 | / | / |
| Group R1-5 | 5 | 23.78 ± 4.32 | Decreased, P < 0.05 | / |
|  | 10 | 48.55 ± 3.68 | Decreased, P < 0.05 | / |
|  | 20 | 73.61 ± 3.92 | / | / |
| Group D5-4 | 2 | 24.26 ± 2.82 | Decreased, P < 0.05 | / |
|  | 10 | 80.67 ± 4.06 | Equivalent, P > 0.05 | / |
| Group S1-6 | 2 | 23.19 ± 1.87 | Decreased, P < 0.05 | / |
|  | 5 | 37.18 ± 3.41 | Decreased, P < 0.05 | / |
|  | 10 | 76.67 ± 3.56 | Equivalent, P > 0.05 | / |
| Group S6-6 | 5 | 30.18 ± 2.97 | Decreased, P < 0.05 | / |
|  | 10 | 59.23 ± 3.49 | Decreased, P < 0.05 | / |
|  | 20 | 85.10 ± 4.41 | / | / |
| Group P1-1 | 2 | 25.85 ± 3.54 | Equivalent, P > 0.05 | / |
|  | 5 | 39.98 ± 2.66 | Decreased, P < 0.05 | / |
|  | 10 | 78.38 ± 3.96 | Equivalent, P > 0.05 | / |

*The test results of the blank control group and the LPS model group were only used as calculation basis, and did not shown as the inhibition rate.
**Only the comparison with the positive group or prototype group at an equal concentration was conducted for the comparison for the Changes; only four groups of compounds (B1-1, C1-1, D1-1, and G1-1) were compared with the prototype compounds of corresponding structures (i.e., styryl sulfones 3B, 3C, 3D, and 3G)

It can be seen that every concentration group for all the compounds had a certain NO inhibitory rate, demonstrating that these compounds have a definite inhibitory effect on the NO release of primary glial cells induced by LPS. Among them, part of compounds had a higher inhibitory rate than the positive control group at an equal concentration, demonstrating that the inhibitory effect on the NO release of primary glial cells induced by LPS of these compounds were stronger than that of the positive control CAPE. The four groups of compounds B1-1, C1-1, D1-1, and G1-1 had a equivalent or higher inhibitory rate compared with those of the styryl sulfone prototype compounds 3B, 3C, 3D, and 3G, respectively, demonstrating that compared with the prototype compounds without the introduction of carbamate functional group, the inhibitory effect on the NO release of primary glial cells induced by LPS has a certain enhancement.

Example 25: Evaluation of the Neuroprotective Activity of the Target Compounds in the Parkinson's Disease Model Mouse (Using the Midbrain p-α-s as the Evaluation Indicator)

1. Experiment Principle

Neurotoxins can be used to establish PD animal models. Currently, 1-methyl-4-phenyl-1,2,3,6-tetrahydropyridine (MPTP) is the sole synthetic toxin which is recognized to induce PD symptoms in human and non-human primates and in mice. Using MPTP subacute modeling method, C57BL/6J male mice were intraperitoneally injected with MPTP 30 mg/kg, once a day for 5 consecutive days. The experiment animals were divided into blank control group, MPTP model group, and compound treatment group. For the MPTP model group and compound treatment group, the compound was administrated by gavage for 21 consecutive days after the completion of modeling; for the MPTP model group, the normal saline was administrated by gavage for 21 consecutive days after the completion of modeling; and for the blank control group, the normal saline was first intraperitoneally injected for 5 days, and then administrated by gavage for 21 days.

Alpha-synuclein is an "unfolded protein" in its natural state. It exists in a monomeric form, and participates in the physiological functions such as the release of neurotransmitters, the establishment of synaptic junctions, and the regulation of synaptic plasticity. Under pathological conditions, more than 90% of alpha-synuclein is phosphorylated at serine of position 129 and converted into phosphorylated alpha-synuclein (p-α-s), thereby forming Lewy bodies. The formation of Lewy bodies is one of the main pathological manifestations and pathological mechanisms for Parkinson's disease, and plays an important role in the formation and development of PD. The detection of the p-α-s expression in the midbrain and substantia nigra of PD model mice can evaluate the neuroprotective activity of the compound.

2. Experiment Method

Half of experiment mice in each group were taken to extract the total midbrain protein, and the change in the midbrain P-α-s protein expression was determined by western-blotting using GAPDH as the internal reference. The experiment included blank control group, MPTP model group, positive control group (caffeic acid phenethyl ester, CAPE), prototype control group (styryl sulfone compounds 3B, 3C, 3D, and 3G, whose structures are shown as above), and target compound group.

3. Experiment Results

The effect of each group on the change in the midbrain p-α-s protein expression in the Parkinson's disease model mouse is shown in the table below:

| Group | Expression (p-α-s/GAPDH) | Changes and statistical difference (P value) | | |
|---|---|---|---|---|
| | | Compared with the model group | Compared with the positive group | Compared with the prototype group* |
| Blank control group | 0.50 ± 0.08 | / | / | / |
| MPTP model group | 1.66 ± 0.10 | / | / | / |
| Positive control group | 0.54 ± 0.12 | Decreased, P < 0.01 | / | / |
| Prototype control group 3B | 0.93 ± 0.04 | Decreased, P < 0.01 | Increased, P < 0.01 | / |
| Prototype control group 3C | 0.92 ± 0.13 | Decreased, P < 0.01 | Increased, P < 0.01 | / |
| Prototype control group 3D | 0.49 ± 0.12 | Decreased, P < 0.01 | Equivalent, P > 0.05 | / |
| Prototype control group 3G | 0.61 ± 0.08 | Decreased, P < 0.01 | Equivalent, P > 0.05 | / |
| Group B1-1 | 0.23 ± 0.12 | Decreased, P < 0.01 | Decreased, P < 0.01 | Decreased, P < 0.01 |
| Group C1-1 | 0.63 ± 0.06 | Decreased, P < 0.01 | Equivalent, P > 0.05 | Decreased, P < 0.01 |
| Group D1-1 | 0.42 ± 0.10 | Decreased, P < 0.01 | Equivalent, P > 0.05 | Equivalent, P > 0.05 |
| Group G1-1 | 0.34 ± 0.09 | Decreased, P < 0.01 | Decreased, P < 0.05 | Decreased, P < 0.01 |
| Group E2-2 | 0.45 ± 0.07 | Decreased, P < 0.01 | Equivalent, P > 0.05 | / |
| Group K3-3 | 0.62 ± 0.11 | Decreased, P < 0.01 | Equivalent, P > 0.05 | / |
| Group K1-4 | 0.45 ± 0.12 | Decreased, P < 0.01 | Equivalent, P > 0.05 | / |
| Group P1-7 | 0.27 ± 0.08 | Decreased, P < 0.01 | Decreased, P < 0.01 | / |
| Group H2-4 | 0.53 ± 0.13 | Decreased, P < 0.01 | Equivalent, P > 0.05 | / |
| Group M1-3 | 0.42 ± 0.05 | Decreased, P < 0.01 | Equivalent, P > 0.05 | / |
| Group L1-4 | 0.38 ± 0.08 | Decreased, P < 0.01 | Decreased, P < 0.05 | / |
| Group K1-3 | 0.34 ± 0.10 | Decreased, P < 0.01 | Decreased, P < 0.05 | / |
| Group J1-4 | 0.47 ± 0.11 | Decreased, P < 0.01 | Equivalent, P > 0.05 | / |
| Group A1-3 | 0.56 ± 0.12 | Decreased, P < 0.01 | Equivalent, P > 0.05 | / |
| Group M1-1 | 0.27 ± 0.08 | Decreased, P < 0.01 | Decreased, P < 0.01 | / |
| Group P1-3 | 0.31 ± 0.05 | Decreased, P < 0.01 | Decreased, P < 0.01 | / |
| Group M1-5 | 0.24 ± 0.05 | Decreased, P < 0.01 | Decreased, P < 0.01 | / |
| Group R1-5 | 0.46 ± 0.11 | Decreased, P < 0.01 | Equivalent, P > 0.05 | / |
| Group D5-4 | 0.64 ± 0.12 | Decreased, P < 0.01 | Equivalent, P > 0.05 | / |
| Group S1-6 | 0.34 ± 0.09 | Decreased, P < 0.01 | Decreased, P < 0.05 | / |
| Group S6-6 | 0.28 ± 0.06 | Decreased, P < 0.01 | Decreased, P < 0.01 | / |
| Group P1-1 | 0.48 ± 0.12 | Decreased, P < 0.01 | Equivalent, P > 0.05 | / |

*Only four groups of compounds (B1-1, C1-1, D1-1, and G1-1) were compared with the prototype compounds of corresponding structures (i.e., styryl sulfones 3B, 3C, 3D, and 3G)

It can be seen that compared with the model group, all the compounds showed a statistically significant decrease in terms of the p-α-s protein expression, demonstrating that these compounds have a definite inhibitory effect on the increase of midbrain p-α-s protein expression in the Parkinson's disease model mouse. Compared with the positive control CAPE, all the compounds were equivalent in terms of the p-α-s protein expression or had a relatively significant or significant decrease in terms of the p-α-s protein expression, demonstrating that the inhibitory effect of these compounds on the increase of midbrain p-α-s protein expression in the Parkinson's disease model mouse were comparable to or even stronger than that of the positive control CAPE. The expressions of the four groups of compounds B1-1, C1-1, D1-1, and G1-1 were equivalent or significantly lower compared with those of the styryl sulfone prototype compounds 3B, 3C, 3D, and 3G, demonstrating that compared with the prototype compounds without the introduction of carbamate functional group, the inhibitory effect of these compounds on the increase of midbrain p-α-s protein expression in the Parkinson's disease model was significantly enhanced.

Example 26: Evaluation of the Neuroprotective Activity of the Target Compounds in the Parkinson's Disease Model Mouse (Using the Substantia Nigra p-α-s as the Evaluation Indicator)

1. Experiment Principle

Identical to that of Example 25.

2. Experiment Method

Half of experiment mice in each group were taken to separate the midbrain after perfusion and fixation. The tissue was trimmed, and the substantia nigra-striatum area was taken to prepare paraffin sections. The p-α-s immunofluorescence staining was performed in the brain sections of mice in each group. The p-α-s expression was observed for the statistics of the change in terms of the p-α-s protein expression. The experiment included blank control group, MPTP model group, positive control group (caffeic acid phenethyl ester, CAPE), prototype control group (styryl sulfone compounds 3B, 3C, 3D, and 3G, whose structures are shown as above), and target compound group.

3. Experiment Results

The effect of each group on the change in the substantia nigra p-α-s protein expression in the Parkinson's disease model mouse is shown in the table below:

| Group | Expression* (Immunofluorescence intensity %) | Changes and statistical difference (P value) Compared with the model group | Compared with the positive group | Compared with the prototype group** |
|---|---|---|---|---|
| Blank control group | 100.00 ± 5.46 | / | / | / |
| MPTP model group | 346.25 ± 5.24 | / | / | / |
| Positive control group | 202.07 ± 8.34 | Decreased, P < 0.01 | / | / |
| Prototype control group 3B | 236.55 ± 13.78 | Decreased, P < 0.01 | Increased, P < 0.01 | / |
| Prototype control group 3C | 132.98 ± 7.78 | Decreased, P < 0.01 | Decreased, P < 0.01 | / |
| Prototype control group 3D | 104.89 ± 7.56 | Decreased, P < 0.01 | Decreased, P < 0.01 | / |
| Prototype control group 3G | 203.66 ± 8.37 | Decreased, P < 0.01 | Equivalent, P > 0.05 | / |
| Group B1-1 | 82.54 ± 9.34 | Decreased, P < 0.01 | Decreased, P < 0.01 | Decreased, P < 0.01 |
| Group C1-1 | 123.59 ± 8.25 | Decreased, P < 0.01 | Decreased, P < 0.01 | Equivalent, P > 0.05 |
| Group D1-1 | 42.52 ± 5.43 | Decreased, P < 0.01 | Decreased, P < 0.01 | Decreased, P < 0.01 |
| Group G1-1 | 77.36 ± 9.15 | Decreased, P < 0.01 | Decreased, P < 0.01 | Decreased, P < 0.01 |
| Group E2-2 | 128.26 ± 11.62 | Decreased, P < 0.01 | Decreased, P < 0.01 | / |
| Group K3-3 | 180.11 ± 13.51 | Decreased, P < 0.01 | Decreased, P < 0.05 | / |
| Group K1-4 | 106.95 ± 9.27 | Decreased, P < 0.01 | Decreased, P < 0.01 | / |
| Group P1-7 | 61.28 ± 5.36 | Decreased, P < 0.01 | Decreased, P < 0.01 | / |
| Group H2-4 | 136.53 ± 8.94 | Decreased, P < 0.01 | Decreased, P < 0.01 | / |
| Group M1-3 | 79.17 ± 5.10 | Decreased, P < 0.01 | Decreased, P < 0.01 | / |
| Group L1-4 | 58.37 ± 6.11 | Decreased, P < 0.01 | Decreased, P < 0.01 | / |
| Group K1-3 | 90.04 ± 7.43 | Decreased, P < 0.01 | Decreased, P < 0.01 | / |
| Group J1-4 | 116.95 ± 8.06 | Decreased, P < 0.01 | Decreased, P < 0.01 | / |
| Group A1-3 | 134.19 ± 11.28 | Decreased, P < 0.01 | Decreased, P < 0.01 | / |
| Group M1-1 | 95.64 ± 9.25 | Decreased, P < 0.01 | Decreased, P < 0.01 | / |
| Group P1-3 | 48.33 ± 5.37 | Decreased, P < 0.01 | Decreased, P < 0.01 | / |
| Group M1-5 | 67.90 ± 3.29 | Decreased, P < 0.01 | Decreased, P < 0.01 | / |
| Group R1-5 | 125.28 ± 9.35 | Decreased, P < 0.01 | Decreased, P < 0.01 | / |
| Group D5-4 | 186.19 ± 11.02 | Decreased, P < 0.01 | Decreased, P < 0.05 | / |
| Group S1-6 | 101.02 ± 5.94 | Decreased, P < 0.01 | Decreased, P < 0.01 | / |
| Group S6-6 | 72.57 ± 6.63 | Decreased, P < 0.01 | Decreased, P < 0.01 | / |
| Group P1-1 | 182.99 ± 12.70 | Decreased, P < 0.01 | Decreased, P < 0.05 | / |

*Expression was expressed in the percentage for the immunofluorescence intensity of each group in the mean immunofluorescence intensity of blank control group.
**Only four groups of compounds (B1-1, C1-1, D1-1, and G1-1) were compared with the prototype compounds of corresponding structures (i.e., styryl sulfones 3B, 3C, 3D, and 3G)

It can be seen that compared with the model group, all the compounds showed a statistically significant decrease in terms of the p-α-s protein expression, demonstrating that these compounds have a definite inhibitory effect on the increase of substantia nigra p-α-s protein expression in the Parkinson's disease model mouse. Compared with the positive control CAPE, most of the compounds had a significant decrease in terms of the p-α-s protein expression, demonstrating that the inhibitory effect of these compounds on the increase of substantia nigra p-α-s protein expression in the Parkinson's disease model mouse were stronger than that of the positive control CAPE. The expressions of the four groups of compounds B1-1, C1-1, D1-1, and G1-1 were equivalent or significantly lower compared with those of the styryl sulfone prototype compounds 3B, 3C, 3D, and 3G, demonstrating that compared with the prototype compounds without the introduction of carbamate functional group, the inhibitory effect of these compounds on the increase of substantia nigra p-α-s protein expression in the Parkinson's disease model was significantly enhanced.

Example 27: Evaluation of the Neuroprotective Activity of the Target Compounds in the Parkinson's Disease Model Mouse (Using the Midbrain TH as the Evaluation Indicator)

1. Experiment Principle

The principle and establishment method of PD model mice are identical to those of Example 25.

The main cause of PD lies in the pathological changes in the substantia nigra-striatum projection system of the brain and the progressive degeneration and loss of dopaminergic neurons. Tyrosine hydroxylase (TH) is the first enzyme in the biosynthesis of catecholamine neurotransmitters, as well as the first rate-limiting enzyme in the dopamine synthesis. It plays an important role in the synthesis and metabolism of the neurotransmitter DA. The TH in PD animal models and patients has a wide range of abnormal changes, from the gene expression to the enzyme protein content and enzyme activity. The detection of the TH expression in the midbrain and substantia nigra of PD model mice can be used to evaluate the neuroprotective activity of the compound.

2. Experiment Method

Half of experiment mice in each group were taken to extract the total midbrain protein, and the change in the midbrain TH was determined by western-blotting using GAPDH as the internal reference. The experiment included blank control group, MPTP model group, positive control group (caffeic acid phenethyl ester, CAPE), prototype control group (styryl sulfone compounds 3B, 3C, 3D, and 3G, whose structures are shown as above), and target compound group.

3. Experiment Results

The effect of each group on the change in the midbrain TH expression in the Parkinson's disease model mouse is shown in the table below:

| Group | Expression (TH/GAPDH) | Compared with the model group | Compared with the positive group | Compared with the prototype group* |
|---|---|---|---|---|
| Blank control group | 1.29 ± 0.03 | / | / | / |
| MPTP model group | 0.44 ± 0.03 | / | / | / |
| Positive control group | 0.85 ± 0.04 | Increased, P < 0.01 | / | / |
| Prototype control group 3B | 0.53 ± 0.03 | Increased, P < 0.01 | Decreased, P < 0.01 | / |
| Prototype control group 3C | 0.63 ± 0.03 | Increased, P < 0.01 | Decreased, P < 0.01 | / |
| Prototype control group 3D | 0.93 ± 0.06 | Increased, P < 0.01 | Increased, P < 0.05 | / |
| Prototype control group 3G | 0.45 ± 0.05 | Increased, P < 0.01 | Decreased, P < 0.01 | / |
| Group B1-1 | 0.92 ± 0.02 | Increased, P < 0.01 | Increased, P < 0.01 | Increased, P < 0.01 |
| Group C1-1 | 1.20 ± 0.06 | Increased, P < 0.01 | Increased, P < 0.01 | Increased, P < 0.01 |
| Group D1-1 | 1.27 ± 0.05 | Increased, P < 0.01 | Increased, P < 0.01 | Increased, P < 0.01 |
| Group G1-1 | 0.70 ± 0.03 | Increased, P < 0.01 | Decreased, P < 0.01 | Increased, P < 0.01 |
| Group E2-2 | 0.97 ± 0.03 | Increased, P < 0.01 | Increased, P < 0.01 | / |
| Group K3-3 | 1.15 ± 0.05 | Increased, P < 0.01 | Increased, P < 0.01 | / |
| Group K1-4 | 0.74 ± 0.08 | Increased, P < 0.01 | Equivalent, P > 0.05 | / |
| Group P1-7 | 0.88 ± 0.06 | Increased, P < 0.01 | Equivalent, P > 0.05 | / |
| Group H2-4 | 1.02 ± 0.04 | Increased, P < 0.01 | Increased, P < 0.01 | / |
| Group M1-3 | 0.84 ± 0.06 | Increased, P < 0.01 | Equivalent, P > 0.05 | / |
| Group L1-4 | 0.79 ± 0.04 | Increased, P < 0.01 | Decreased, P < 0.05 | / |
| Group K1-3 | 0.91 ± 0.04 | Increased, P < 0.01 | Increased, P < 0.05 | / |
| Group J1-4 | 0.89 ± 0.04 | Increased, P < 0.01 | Equivalent, P > 0.05 | / |
| Group A1-3 | 0.93 ± 0.07 | Increased, P < 0.01 | Increased, P < 0.05 | / |
| Group M1-1 | 1.35 ± 0.04 | Increased, P < 0.01 | Increased, P < 0.01 | / |
| Group P1-3 | 0.77 ± 0.03 | Increased, P < 0.01 | Decreased, P < 0.05 | / |
| Group M1-5 | 0.83 ± 0.06 | Increased, P < 0.01 | Equivalent, P > 0.05 | / |
| Group R1-5 | 0.94 ± 0.03 | Increased, P < 0.01 | Increased, P < 0.01 | / |
| Group D5-4 | 1.19 ± 0.05 | Increased, P < 0.01 | Increased, P < 0.01 | / |
| Group S1-6 | 0.91 ± 0.06 | Increased, P < 0.01 | Equivalent, P > 0.05 | / |
| Group S6-6 | 1.07 ± 0.06 | Increased, P < 0.01 | Increased, P < 0.01 | / |
| Group P1-1 | 0.88 ± 0.04 | Increased, P < 0.01 | Equivalent, P > 0.05 | / |

*Only four groups of compounds (B1-1, C1-1, D1-1, and G1-1) were compared with the prototype compounds of corresponding structures (i.e., styryl sulfones 3B, 3C, 3D, and 3G).

It can be seen that compared with the model group, all the compounds showed a statistically significant increase in the TH expression, demonstrating that these compounds have a definite protective effect on the midbrain TH expression in the Parkinson's disease model mouse. Compared with the positive control CAPE, most of the compounds were equivalent in the TH expression or had a relatively significant or significant increase in the TH expression, demonstrating that the protective effect of these compounds on the midbrain TH expression in the Parkinson's disease model mouse were comparable to or even stronger than that of the positive control CAPE. The expressions of the four groups of compounds B1-1, C1-1, D1-1, and G1-1 were significantly higher compared with those of the styryl sulfone prototype compounds 3B, 3C, 3D, and 3G, demonstrating that compared with the prototype compounds without the introduction of carbamate functional group, the protective effect of these compounds on the midbrain TH expression in the Parkinson's disease model was significantly enhanced.

Example 28: Evaluation of the Neuroprotective Activity of the Target Compounds in the Parkinson's Disease Model Mouse (Using the Substantia Nigra TH as the Evaluation Indicator)

1. Experiment Principle
Identical to that of Example 27.
2. Experiment Method
Half of experiment mice in each group were taken to separate the midbrain after perfusion and fixation. The tissue was trimmed, and the substantia nigra-striatum area was taken to prepare paraffin sections. The TH immunofluorescence staining was performed in the brain sections of mice in each group. The TH expression was observed for the statistics of the change in the number of neurons with TH positive expression. The experiment included blank control group, MPTP model group, positive control group (caffeic acid phenethyl ester, CAPE), prototype control group (styryl sulfone compounds 3B, 3C, 3D, and 3G, whose structures are shown as above), and target compound group.

3. Experiment Results
The effect of each group on the change in the substantia nigra TH expression in the Parkinson's disease model mouse is shown in the table below:

| Group | Expression* (Immunofluorescence intensity %) | Changes and statistical difference (P value) | | |
|---|---|---|---|---|
| | | Compared with the model group | Compared with the positive group | Compared with the prototype group** |
| Blank control group | 100.00 ± 2.32 | / | / | / |
| MPTP model group | 57.57 ± 7.70 | / | / | / |
| Positive control group | 79.21 ± 6.59 | Increased, P < 0.01 | / | / |
| Prototype control group 3B | 83.18 ± 5.87 | Increased, P < 0.01 | Equivalent, P > 0.05 | / |
| Prototype control group 3C | 74.63 ± 9.15 | Increased, P < 0.01 | Equivalent, P > 0.05 | / |
| Prototype control group 3D | 87.38 ± 4.01 | Increased, P < 0.01 | Increased, P < 0.05 | / |
| Prototype control group 3G | 76.08 ± 7.08 | Increased, P < 0.01 | Equivalent, P > 0.05 | / |
| Group B1-1 | 95.86 ± 4.43 | Increased, P < 0.01 | Increased, P < 0.01 | Increased, P < 0.01 |
| Group C1-1 | 96.58 ± 6.15 | Increased, P < 0.01 | Increased, P < 0.01 | Increased, P < 0.01 |
| Group D1-1 | 99.19 ± 3.67 | Increased, P < 0.01 | Increased, P < 0.01 | Increased, P < 0.01 |
| Group G1-1 | 77.13 ± 7.40 | Increased, P < 0.01 | Equivalent, P > 0.05 | Equivalent, P > 0.05 |
| Group E2-2 | 93.12 ± 4.56 | Increased, P < 0.01 | Increased, P < 0.01 | / |
| Group K3-3 | 98.53 ± 3.08 | Increased, P < 0.01 | Increased, P < 0.01 | / |
| Group K1-4 | 74.20 ± 6.58 | Increased, P < 0.01 | Equivalent, P > 0.05 | / |
| Group P1-7 | 88.07 ± 5.03 | Increased, P < 0.01 | Increased, P < 0.05 | / |
| Group H2-4 | 95.20 ± 6.06 | Increased, P < 0.01 | Increased, P < 0.01 | / |
| Group M1-3 | 84.07 ± 3.19 | Increased, P < 0.01 | Equivalent, P > 0.05 | / |
| Group L1-4 | 83.22 ± 5.98 | Increased, P < 0.01 | Equivalent, P > 0.05 | / |
| Group K1-3 | 87.28 ± 4.11 | Increased, P < 0.01 | Increased, P < 0.05 | / |
| Group J1-4 | 88.65 ± 5.41 | Increased, P < 0.01 | Increased, P < 0.05 | / |
| Group A1-3 | 89.68 ± 5.69 | Increased, P < 0.01 | Increased, P < 0.05 | / |
| Group M1-1 | 101.36 ± 5.21 | Increased, P < 0.01 | Increased, P < 0.01 | / |
| Group P1-3 | 79.20 ± 6.53 | Increased, P < 0.01 | Equivalent, P > 0.05 | / |
| Group M1-5 | 87.24 ± 2.97 | Increased, P < 0.01 | Increased, P < 0.05 | / |
| Group R1-5 | 92.45 ± 3.93 | Increased, P < 0.01 | Increased, P < 0.01 | / |
| Group D5-4 | 99.86 ± 6.27 | Increased, P < 0.01 | Increased, P < 0.01 | / |
| Group S1-6 | 87.73 ± 3.49 | Increased, P < 0.01 | Increased, P < 0.05 | / |
| Group S6-6 | 96.01 ± 7.32 | Increased, P < 0.01 | Increased, P < 0.01 | / |
| Group P1-1 | 88.13 ± 3.43 | Increased, P < 0.01 | Increased, P < 0.05 | / |

*Expression was expressed in the percentage for the immunofluorescence intensity of each group in the mean immunofluorescence intensity of blank control group.
**Only four groups of compounds (B1-1, C1-1, D1-1, and G1-1) were compared with the prototype compounds of corresponding structures (i.e., styryl sulfones 3B, 3C, 3D, and 3G).

It can be seen that compared with the model group, all the compounds showed a statistically significant increase in the TH expression, demonstrating that these compounds have a definite protective effect on the substantia nigra TH expression in the Parkinson's disease model mouse. Compared with the positive control CAPE, all the compounds were equivalent in the TH expression or had a relatively significant or significant increase in the TH expression, demonstrating that the protective effect of these compounds on the substantia nigra TH expression in the Parkinson's disease model mouse were comparable to or even stronger than that of the positive control CAPE. The expressions of the four groups of compounds B1-1, C1-1, D1-1, and G1-1 were equivalent or significantly higher compared with those of the styryl sulfone prototype compounds 3B, 3C, 3D, and 3G, demonstrating that compared with the prototype compounds without the introduction of carbamate functional group, the protective effect of these compounds on the substantia nigra TH expression in the Parkinson's disease model was significantly enhanced.

Example 29: Study on the Neuroprotection Mechanism of the Target Compounds in the Parkinson's Disease Model Mouse (i.e., the Inhibitory Effect on the Activation of p38 MAPK Phosphorylation, Using Midbrain Pp38 as the Evaluation Indicator)

1. Experiment Principle

The p38 mitogen-activated protein kinase (p38 MAPK) is expressed in both neurons and glial cells, and is the intersection point of neuron-glial cell network information regulations. The activation of p38 signaling pathway is an important initiator of neuronal degeneration, which continuously induces the apoptosis of dopaminergic neurons in multiple ways. It has become a research hotspot for the treatment of PD. Studies have shown that the protective mechanism of CAPE against the death of primary cultured cerebellar granule neurons induced by glutamate lies in inhibiting the activation of p38 phosphorylation and in turn inhibiting the activation of the caspase 3 apoptotic pathway to prevent neuronal apoptosis. Therefore, the MPTP-induced PD mouse model can be used to investigate the inhibitory effect of the target compounds on the activation of p38 phosphorylation on the overall animal level.

2. Experiment Method

Half of experiment mice in each group were taken to extract the total midbrain protein, and the change in the midbrain phosphorylated p38 protein expression was determined by western-blotting using GAPDH as the internal reference. The experiment included blank control group, MPTP model group, positive control group (caffeic acid phenethyl ester, CAPE), prototype control group (styryl sulfone compounds 3B, 3C, 3D, and 3G, whose structures are shown as above), and target compound group.

3. Experiment Results

The effect of each group on the change in the midbrain pp38 protein expression in the Parkinson's disease model mouse is shown in the table below:

| Group | Expression (pp38/GAPDH) | Changes and statistical difference (P value) | | |
|---|---|---|---|---|
| | | Compared with the model group | Compared with the positive group | Compared with the prototype group* |
| Blank control group | 0.24 ± 0.03 | / | / | / |
| MPTP model group | 1.73 ± 0.15 | / | / | / |
| Positive control group | 0.58 ± 0.12 | Decreased, P < 0.01 | / | / |
| Prototype control group 3B | 1.18 ± 0.08 | Decreased, P < 0.01 | Increased, P < 0.01 | / |
| Prototype control group 3C | 0.85 ± 0.22 | Decreased, P < 0.01 | Increased, P < 0.05 | / |
| Prototype control group 3D | 1.00 ± 0.11 | Decreased, P < 0.01 | Increased, P < 0.01 | / |
| Prototype control group 3G | 0.69 ± 0.22 | Decreased, P < 0.01 | Equivalent, P > 0.05 | / |
| Group B1-1 | 0.37 ± 0.12 | Decreased, P < 0.01 | Decreased, P < 0.05 | Decreased, P < 0.01 |
| Group C1-1 | 0.63 ± 0.06 | Decreased, P < 0.01 | Equivalent, P > 0.05 | Equivalent, P > 0.05 |
| Group D1-1 | 0.50 ± 0.13 | Decreased, P < 0.01 | Equivalent, P > 0.05 | Decreased, P < 0.01 |
| Group G1-1 | 0.33 ± 0.07 | Decreased, P < 0.01 | Decreased, P < 0.01 | Decreased, P < 0.01 |
| Group E2-2 | 0.43 ± 0.06 | Decreased, P < 0.01 | Decreased, P < 0.05 | / |
| Group K3-3 | 0.55 ± 0.08 | Decreased, P < 0.01 | Equivalent, P > 0.05 | / |
| Group K1-4 | 0.44 ± 0.05 | Decreased, P < 0.01 | Decreased, P < 0.05 | / |
| Group P1-7 | 0.40 ± 0.04 | Decreased, P < 0.01 | Decreased, P < 0.01 | / |
| Group H2-4 | 0.43 ± 0.05 | Decreased, P < 0.01 | Decreased, P < 0.05 | / |
| Group M1-3 | 0.42 ± 0.06 | Decreased, P < 0.01 | Decreased, P < 0.05 | / |
| Group L1-4 | 0.28 ± 0.04 | Decreased, P < 0.01 | Decreased, P < 0.01 | / |
| Group K1-3 | 0.35 ± 0.06 | Decreased, P < 0.01 | Decreased, P < 0.01 | / |
| Group J1-4 | 0.41 ± 0.08 | Decreased, P < 0.01 | Decreased, P < 0.05 | / |
| Group A1-3 | 0.27 ± 0.08 | Decreased, P < 0.01 | Decreased, P < 0.01 | / |
| Group M1-1 | 0.40 ± 0.05 | Decreased, P < 0.01 | Decreased, P < 0.05 | / |
| Group P1-3 | 0.33 ± 0.07 | Decreased, P < 0.01 | Decreased, P < 0.01 | / |
| Group M1-5 | 0.29 ± 0.06 | Decreased, P < 0.01 | Decreased, P < 0.01 | / |
| Group R1-5 | 0.44 ± 0.07 | Decreased, P < 0.01 | Decreased, P < 0.05 | / |
| Group D5-4 | 0.61 ± 0.07 | Decreased, P < 0.01 | Equivalent, P > 0.05 | / |
| Group S1-6 | 0.21 ± 0.04 | Decreased, P < 0.01 | Decreased, P < 0.01 | / |
| Group S6-6 | 0.27 ± 0.05 | Decreased, P < 0.01 | Decreased, P < 0.01 | / |
| Group P1-1 | 0.50 ± 0.09 | Decreased, P < 0.01 | Equivalent, P > 0.05 | / |

*Only four groups of compounds (B1-1, C1-1, D1-1, and G1-1) were compared with the prototype compounds of corresponding structures (i.e., styryl sulfones 3B, 3C, 3D, and 3G)

It can be seen that compared with the model group, all the compounds showed a statistically significant decrease in the pp38 protein expression, demonstrating that these compounds have a definite inhibitory effect on the increase of midbrain pp38 protein expression in the Parkinson's disease model mouse. Compared with the positive control CAPE, all the compounds were equivalent in the pp38 protein expression or had a relatively significant or significant decrease in the pp38 protein expression, demonstrating that the inhibitory effect of these compounds on the increase of midbrain pp38 protein expression in the Parkinson's disease model mouse were comparable to or even stronger than that of the positive control CAPE. The expressions of the four groups of compounds B1-1, C1-1, D1-1, and G1-1 were equivalent or significantly lower compared with those of the styryl sulfone prototype compounds 3B, 3C, 3D, and 3G, demonstrating that compared with the prototype compounds without the introduction of carbamate functional group, the inhibitory effect of these compounds on the increase of midbrain pp38 protein expression in the Parkinson's disease model was significantly enhanced.

Example 30: Study on the Neuroprotection Mechanism of the Target Compounds in the Parkinson's Disease Model Mouse (i.e., the Inhibitory Effect on the Activation of p38 MAPK Phosphorylation, Using Substantia Nigra Pp38 as the Evaluation Indicator)

1. Experiment Principle
Identical to that of Example 29.
2. Experiment Method
Half of experiment mice in each group were taken to separate the midbrain after perfusion and fixation. The tissue was trimmed, and the substantia nigra-striatum area was taken to prepare paraffin sections. The double immunofluorescence staining for TH and phosphorylated p38 was performed to observe the coexpression of TH and phosphorylated p38, for the statistics of the change in the phosphorylated p38 protein expression. The experiment included blank control group, MPTP model group, positive control group (caffeic acid phenethyl ester, CAPE), prototype control group (styryl sulfone compounds 3B, 3C, 3D, and 3G, whose structures are shown as above), and target compound group.
3. Experiment Results
The effect of each group on the change in the substantia nigra pp38 protein expression in the Parkinson's disease model mouse is shown in the table below:

CAPE, all the compounds had a relatively significant or significant decrease in the pp38 protein expression, demonstrating that the inhibitory effect of these compounds on the increase of substantia nigra pp38 protein expression in the Parkinson's disease model mouse were stronger than that of the positive control CAPE. The expressions of the four groups of compounds B1-1, C1-1, D1-1, and G1-1 were equivalent or significantly lower compared with those of the styryl sulfone prototype compounds 3B, 3C, 3D, and 3G, demonstrating that compared with the prototype compounds without the introduction of carbamate functional group, the inhibitory effect of these compounds on the increase of substantia nigra pp38 protein expression in the Parkinson's disease model was significantly enhanced.

Example 31: Study on the Neuroprotection Mechanism of the Target Compounds in the Parkinson's Disease Model Mouse (i.e., the Inhibitory Effect on the Glial Cell Activation, Using Midbrain CD11b as the Evaluation Indicator)

1. Experiment Principle
More and more evidences show that the glial cells play an important role in supporting the neuron development and maintaining the immune homeostasis of the central nervous system. Neuron-glial cell network homeostasis disorder is an important factor for the selective and progressive death of

| Group | Expression* (Immunofluorescence intensity %) | Changes and statistical difference (P value) | | |
|---|---|---|---|---|
| | | Compared with the model group | Compared with the positive group | Compared with the prototype group** |
| Blank control group | 100.00 ± 8.25 | / | / | / |
| MPTP model group | 255.23 ± 26.39 | / | / | / |
| Positive control group | 139.72 ± 25.32 | Decreased, P < 0.01 | / | / |
| Prototype control group 3B | 134.70 ± 31.07 | Decreased, P < 0.01 | Equivalent, P > 0.05 | / |
| Prototype control group 3C | 138.79 ± 27.44 | Decreased, P < 0.01 | Equivalent, P > 0.05 | / |
| Prototype control group 3D | 114.68 ± 21.42 | Decreased, P < 0.01 | Equivalent, P > 0.05 | / |
| Prototype control group 3G | 118.25 ± 10.60 | Decreased, P < 0.01 | Equivalent, P > 0.05 | / |
| Group B1-1 | 76.35 ± 21.90 | Decreased, P < 0.01 | Decreased, P < 0.01 | Decreased, P < 0.01 |
| Group C1-1 | 108.71 ± 12.51 | Decreased, P < 0.01 | Decreased, P < 0.05 | Equivalent, P > 0.05 |
| Group D1-1 | 57.50 ± 15.33 | Decreased, P < 0.01 | Decreased, P < 0.01 | Decreased, P < 0.01 |
| Group G1-1 | 82.16 ± 8.10 | Decreased, P < 0.01 | Decreased, P < 0.01 | Decreased, P < 0.01 |
| Group E2-2 | 96.01 ± 10.37 | Decreased, P < 0.01 | Decreased, P < 0.01 | / |
| Group K3-3 | 111.17 ± 9.62 | Decreased, P < 0.01 | Decreased, P < 0.05 | / |
| Group K1-4 | 100.80 ± 5.48 | Decreased, P < 0.01 | Decreased, P < 0.01 | / |
| Group P1-7 | 77.29 ± 13.06 | Decreased, P < 0.01 | Decreased, P < 0.01 | / |
| Group H2-4 | 103.17 ± 12.58 | Decreased, P < 0.01 | Decreased, P < 0.05 | / |
| Group M1-3 | 100.22 ± 14.12 | Decreased, P < 0.01 | Decreased, P < 0.05 | / |
| Group L1-4 | 62.93 ± 17.51 | Decreased, P < 0.01 | Decreased, P < 0.01 | / |
| Group K1-3 | 73.08 ± 18.10 | Decreased, P < 0.01 | Decreased, P < 0.01 | / |
| Group J1-4 | 100.62 ± 13.35 | Decreased, P < 0.01 | Decreased, P < 0.05 | / |
| Group A1-3 | 58.19 ± 12.07 | Decreased, P < 0.01 | Decreased, P < 0.01 | / |
| Group M1-1 | 98.35 ± 6.93 | Decreased, P < 0.01 | Decreased, P < 0.01 | / |
| Group P1-3 | 81.90 ± 9.52 | Decreased, P < 0.01 | Decreased, P < 0.01 | / |
| Group M1-5 | 87.45 ± 11.05 | Decreased, P < 0.01 | Decreased, P < 0.01 | / |
| Group R1-5 | 101.93 ± 7.44 | Decreased, P < 0.01 | Decreased, P < 0.01 | / |
| Group D5-4 | 103.25 ± 15.27 | Decreased, P < 0.01 | Decreased, P < 0.05 | / |
| Group S1-6 | 45.83 ± 9.29 | Decreased, P < 0.01 | Decreased, P < 0.01 | / |
| Group S6-6 | 105.30 ± 10.08 | Decreased, P < 0.01 | Decreased, P < 0.05 | / |
| Group P1-1 | 99.55 ± 8.46 | Decreased, P < 0.01 | Decreased, P < 0.01 | / |

*Expression was expressed in the percentage for the immunofluorescence intensity of each group in the mean immunofluorescence intensity of blank control group.
**Only four groups of compounds (B1-1, C1-1, D1-1, and G1-1) were compared with the prototype compounds of corresponding structures (i.e., styryl sulfones 3B, 3C, 3D, and 3G)

It can be seen that compared with the model group, all the compounds showed a statistically significant decrease in the pp38 protein expression, demonstrating that these compounds have a definite inhibitory effect on the increase of substantia nigra pp38 protein expression in the Parkinson's disease model mouse. Compared with the positive control substantia nigra dopaminergic neurons in PD. In the neurotoxic effect of MPTP, the excessive activations of microglial cells and astrocytes produce a variety of inflammatory cytokines and reactive oxygen species (ROS). These inflammatory factors and ROS amplify their respective toxicities and mediate malignant feedback loop, causing a cascade inflammation response and aggravating the pathological process of PD. CD11b and GFAP are the marker proteins for activations of microglial cells and astrocytes, respectively. Therefore, the effect of the target compounds on the activations of the microglial cells and astrocytes in the substantia nigra, hippocampus, and midbrain areas of MPTP-induced PD mice can be investigated, to explore the mechanism of the anti-PD effect of the target compounds by inhibiting the neuroinflammation.

2. Experiment Method

Half of experiment mice in each group were taken to extract the total midbrain protein, and the change in the midbrain P-α-s protein expression was determined by western-blotting using CD11b as the internal reference. The experiment included blank control group, MPTP model group, positive control group (caffeic acid phenethyl ester, CAPE), prototype control group (styryl sulfone compounds 3B, 3C, 3D), and 3G, whose structures are shown as above), and target compound group.

3. Experiment Results

The effect of each group on the change in the midbrain CD11b protein expression in the Parkinson's disease model mouse is shown in the table below:

groups of compounds B1-1, C1-1, D1-1, and G1-1 were equivalent or lower compared with those of the styryl sulfone prototype compounds 3B, 3C, 3D), and 3G, demonstrating that compared with the prototype compounds without the introduction of carbamate functional group, the inhibitory effect of these compounds on the increase of midbrain CD11b protein expression in the Parkinson's disease model was significantly enhanced.

Example 32: Study on the Neuroprotection Mechanism of the Target Compounds in the Parkinson's Disease Model Mouse (i.e., the Inhibitory Effect on the Glial Cell Activation, Using Substantia Nigra CD11b as the Evaluation Indicator)

1. Experiment Principle

Identical to that of Example 31.

2. Experiment Method

Half of experiment mice in each group were taken to separate the midbrain after perfusion and fixation. The tissue was trimmed, and the substantia nigra area was taken to prepare paraffin sections. The CD11b immunohistochemical

| Group | Expression (CD11b/GAPDH) | Changes and statistical difference (P value) | | |
|---|---|---|---|---|
| | | Compared with the model group | Compared with the positive group | Compared with the prototype group* |
| Blank control group | 0.76 ± 0.02 | / | / | / |
| MPTP model group | 1.85 ± 0.05 | / | / | / |
| Positive control group | 1.28 ± 0.10 | Decreased, $P < 0.01$ | / | / |
| Prototype control group 3B | 1.31 ± 0.10 | Decreased, $P < 0.01$ | Equivalent, $P > 0.05$ | / |
| Prototype control group 3C | 1.02 ± 0.13 | Decreased, $P < 0.01$ | Decreased, $P < 0.01$ | / |
| Prototype control group 3D | 1.30 ± 0.10 | Decreased, $P < 0.01$ | Equivalent, $P > 0.05$ | / |
| Prototype control group 3G | 0.67 ± 0.12 | Decreased, $P < 0.01$ | Decreased, $P < 0.01$ | / |
| Group B1-1 | 0.41 ± 0.05 | Decreased, $P < 0.01$ | Decreased, $P < 0.01$ | Decreased, $P < 0.01$ |
| Group C1-1 | 1.11 ± 0.08 | Decreased, $P < 0.01$ | Decreased, $P < 0.05$ | Equivalent, $P > 0.05$ |
| Group D1-1 | 0.33 ± 0.05 | Decreased, $P < 0.01$ | Decreased, $P < 0.01$ | Decreased, $P < 0.01$ |
| Group G1-1 | 0.50 ± 0.06 | Decreased, $P < 0.01$ | Decreased, $P < 0.01$ | Decreased, $P < 0.05$ |
| Group E2-2 | 1.17 ± 0.06 | Decreased, $P < 0.01$ | Equivalent, $P > 0.05$ | / |
| Group K3-3 | 1.15 ± 0.07 | Decreased, $P < 0.01$ | Decreased, $P < 0.05$ | / |
| Group K1-4 | 1.09 ± 0.10 | Decreased, $P < 0.01$ | Decreased, $P < 0.05$ | / |
| Group P1-7 | 0.39 ± 0.03 | Decreased, $P < 0.01$ | Decreased, $P < 0.01$ | / |
| Group H2-4 | 0.69 ± 0.04 | Decreased, $P < 0.01$ | Decreased, $P < 0.01$ | / |
| Group M1-3 | 0.84 ± 0.06 | Decreased, $P < 0.01$ | Decreased, $P < 0.01$ | / |
| Group L1-4 | 1.09 ± 0.09 | Decreased, $P < 0.01$ | Decreased, $P < 0.05$ | / |
| Group K1-3 | 1.01 ± 0.08 | Decreased, $P < 0.01$ | Decreased, $P < 0.01$ | / |
| Group J1-4 | 0.75 ± 0.06 | Decreased, $P < 0.01$ | Decreased, $P < 0.01$ | / |
| Group A1-3 | 1.12 ± 0.06 | Decreased, $P < 0.01$ | Decreased, $P < 0.05$ | / |
| Group M1-1 | 0.46 ± 0.04 | Decreased, $P < 0.01$ | Decreased, $P < 0.01$ | / |
| Group P1-3 | 1.09 ± 0.08 | Decreased, $P < 0.01$ | Decreased, $P < 0.01$ | / |
| Group M1-5 | 0.83 ± 0.07 | Decreased, $P < 0.01$ | Decreased, $P < 0.01$ | / |
| Group R1-5 | 1.25 ± 0.08 | Decreased, $P < 0.01$ | Equivalent, $P > 0.05$ | / |
| Group D5-4 | 1.11 ± 0.10 | Decreased, $P < 0.01$ | Decreased, $P < 0.05$ | / |
| Group S1-6 | 0.43 ± 0.05 | Decreased, $P < 0.01$ | Decreased, $P < 0.01$ | / |
| Group S6-6 | 0.62 ± 0.04 | Decreased, $P < 0.01$ | Decreased, $P < 0.01$ | / |
| Group P1-1 | 0.70 ± 0.06 | Decreased, $P < 0.01$ | Decreased, $P < 0.01$ | / |

*Only four groups of compounds (B1-1, C1-1, D1-1, and G1-1) were compared with the prototype compounds of corresponding structures (i.e., styryl sulfones 3B, 3C, 3D, and 3G).

It can be seen that compared with the model group, all the compounds showed a statistically significant decrease in the CD11b protein expression, demonstrating that these compounds have a definite inhibitory effect on the increase of midbrain CD11b protein expression in the Parkinson's disease model mouse. Compared with the positive control CAPE, most of the compounds had a relatively significant or significant decrease in the CD11b protein expression, demonstrating that the inhibitory effect of these compounds on the increase of midbrain CD11b protein expression in the Parkinson's disease model mouse were stronger than that of the positive control CAPE. The expressions of the four staining was performed for the statistics of the change in the number of microglial cells with CD11b positive expression. The experiment included blank control group, MPTP model group, positive control group (caffeic acid phenethyl ester, CAPE), prototype control group (styryl sulfone compounds 3B, 3C, 3D, and 3G, whose structures are shown as above), and target compound group.

3. Experiment Results

The effect of each group on the change in the number of substantia nigra microglial cells with CD11b positive expression in the Parkinson's disease model mouse is shown in the table below:

| Group | Positive cell number | Changes and statistical difference (P value) | | |
|---|---|---|---|---|
| | | Compared with the model group | Compared with the positive group | Compared with the prototype group* |
| Blank control group | 10 ± 2 | / | / | / |
| MPTP model group | 145 ± 11 | / | / | / |
| Positive control group | 49 ± 7 | Decreased, P < 0.01 | / | / |
| Prototype control group 3B | 44 ± 5 | Decreased, P < 0.01 | Equivalent, P > 0.05 | / |
| Prototype control group 3C | 70 ± 6 | Decreased, P < 0.01 | Increased, P < 0.01 | / |
| Prototype control group 3D | 39 ± 4 | Decreased, P < 0.01 | Decreased, P < 0.05 | / |
| Prototype control group 3G | 52 ± 5 | Decreased, P < 0.01 | Equivalent, P > 0.05 | / |
| Group B1-1 | 32 ± 4 | Decreased, P < 0.01 | Decreased, P < 0.01 | Decreased, P < 0.01 |
| Group C1-1 | 27 ± 4 | Decreased, P < 0.01 | Decreased, P < 0.01 | Decreased, P < 0.01 |
| Group D1-1 | 15 ± 3 | Decreased, P < 0.01 | Decreased, P < 0.01 | Decreased, P < 0.01 |
| Group G1-1 | 36 ± 3 | Decreased, P < 0.01 | Decreased, P < 0.01 | Decreased, P < 0.01 |
| Group E2-2 | 40 ± 5 | Decreased, P < 0.01 | Decreased, P < 0.05 | / |
| Group K3-3 | 39 ± 3 | Decreased, P < 0.01 | Decreased, P < 0.05 | / |
| Group K1-4 | 30 ± 4 | Decreased, P < 0.01 | Decreased, P < 0.01 | / |
| Group P1-7 | 15 ± 2 | Decreased, P < 0.01 | Decreased, P < 0.01 | / |
| Group H2-4 | 29 ± 4 | Decreased, P < 0.01 | Decreased, P < 0.01 | / |
| Group M1-3 | 33 ± 5 | Decreased, P < 0.01 | Decreased, P < 0.01 | / |
| Group L1-4 | 35 ± 2 | Decreased, P < 0.01 | Decreased, P < 0.01 | / |
| Group K1-3 | 32 ± 4 | Decreased, P < 0.01 | Decreased, P < 0.01 | / |
| Group J1-4 | 24 ± 5 | Decreased, P < 0.01 | Decreased, P < 0.01 | / |
| Group A1-3 | 38 ± 4 | Decreased, P < 0.01 | Decreased, P < 0.05 | / |
| Group M1-1 | 20 ± 3 | Decreased, P < 0.01 | Decreased, P < 0.01 | / |
| Group P1-3 | 31 ± 4 | Decreased, P < 0.01 | Decreased, P < 0.01 | / |
| Group M1-5 | 28 ± 3 | Decreased, P < 0.01 | Decreased, P < 0.01 | / |
| Group R1-5 | 39 ± 6 | Decreased, P < 0.01 | Decreased, P < 0.05 | / |
| Group D5-4 | 41 ± 3 | Decreased, P < 0.01 | Decreased, P < 0.05 | / |
| Group S1-6 | 18 ± 3 | Decreased, P < 0.01 | Decreased, P < 0.01 | / |
| Group S6-6 | 19 ± 2 | Decreased, P < 0.01 | Decreased, P < 0.01 | / |
| Group P1-1 | 26 ± 3 | Decreased, P < 0.01 | Decreased, P < 0.01 | / |

*Only four groups of compounds (B1-1, C1-1, D1-1, and G1-1) were compared with the prototype compounds of corresponding structures (i.e., styryl sulfones 3B, 3C, 3D, and 3G)

It can be seen that compared with the model group, all the compounds showed a statistically significant decrease in the number of microglial cells with CD11b positive expression, demonstrating that these compounds have a definite inhibitory effect on the increase of number of substantia nigra microglial cells with CD11b positive expression in the Parkinson's disease model mouse. Compared with the positive control CAPE, all the compounds had a relatively significant or significant decrease in the number of microglial cells with CD11b positive expression, demonstrating that the inhibitory effect of these compounds on the increase of number of substantia nigra microglial cells with CD11b positive expression in the Parkinson's disease model mouse were stronger than that of the positive control CAPE. The numbers of positive cells of the four groups of compounds B1-1, C1-1, D1-1, and G1-1 were significantly lower compared with those of the styryl sulfone prototype compounds 3B, 3C, 3D), and 3G, demonstrating that compared with the prototype compounds without the introduction of carbamate functional group, the inhibitory effect of these compounds on the increase of number of substantia nigra microglial cells with CD11b positive expression in the Parkinson's disease model mouse was significantly enhanced.

Example 33: Study on the Neuroprotection Mechanism of the Target Compounds in the Parkinson's Disease Model Mouse (i.e., the Inhibitory Effect on the Glial Cell Activation, Using Hippocampus CD11b as the Evaluation Indicator)

1. Experiment Principle

Identical to that of Example 35.

2. Experiment Method

Half of experiment mice in each group were taken to separate the midbrain after perfusion and fixation. The tissue was trimmed, and the hippocampus area was taken to prepare paraffin sections. The CD11b immunohistochemical staining was performed for the statistics of the change in the number of microglial cells with CD11b positive expression. The experiment included blank control group, MPTP model group, positive control group (caffeic acid phenethyl ester, CAPE), prototype control group (styryl sulfone compounds 3B, 3C, 3D, and 3G, whose structures are shown as above), and target compound group.

3. Experiment Results

The effect of each group on the change in the number of hippocampus microglial cell with CD11b positive expression in the Parkinson's disease model mouse is shown in the table below:

| Group | Positive cell number | Changes and statistical difference (P value) | | |
|---|---|---|---|---|
| | | Compared with the model group | Compared with the positive group | Compared with the prototype group* |
| Blank control group | 4 ± 1 | / | / | / |
| MPTP model group | 52 ± 3 | / | / | / |
| Positive control group | 24 ± 2 | Decreased, P < 0.01 | / | / |

-continued

| Group | Positive cell number | Compared with the model group | Compared with the positive group | Compared with the prototype group* |
|---|---|---|---|---|
| Prototype control group 3B | 16 ± 2 | Decreased, P < 0.01 | Decreased, P < 0.01 | / |
| Prototype control group 3C | 20 ± 3 | Decreased, P < 0.01 | Decreased, P < 0.05 | / |
| Prototype control group 3D | 18 ± 3 | Decreased, P < 0.01 | Decreased, P < 0.01 | / |
| Prototype control group 3G | 18 ± 3 | Decreased, P < 0.01 | Decreased, P < 0.01 | / |
| Group B1-1 | 9 ± 2 | Decreased, P < 0.01 | Decreased, P < 0.01 | Decreased, P < 0.01 |
| Group C1-1 | 7 ± 2 | Decreased, P < 0.01 | Decreased, P < 0.01 | Decreased, P < 0.01 |
| Group D1-1 | 7 ± 1 | Decreased, P < 0.01 | Decreased, P < 0.01 | Decreased, P < 0.01 |
| Group G1-1 | 6 ± 1 | Decreased, P < 0.01 | Decreased, P < 0.01 | Decreased, P < 0.01 |
| Group E2-2 | 15 ± 2 | Decreased, P < 0.01 | Decreased, P < 0.01 | / |
| Group K3-3 | 18 ± 1 | Decreased, P < 0.01 | Decreased, P < 0.01 | / |
| Group K1-4 | 13 ± 2 | Decreased, P < 0.01 | Decreased, P < 0.01 | / |
| Group P1-7 | 8 ± 2 | Decreased, P < 0.01 | Decreased, P < 0.01 | / |
| Group H2-4 | 7 ± 1 | Decreased, P < 0.01 | Decreased, P < 0.01 | / |
| Group M1-3 | 12 ± 2 | Decreased, P < 0.01 | Decreased, P < 0.01 | / |
| Group L1-4 | 15 ± 2 | Decreased, P < 0.01 | Decreased, P < 0.01 | / |
| Group K1-3 | 16 ± 1 | Decreased, P < 0.01 | Decreased, P < 0.01 | / |
| Group J1-4 | 10 ± 2 | Decreased, P < 0.01 | Decreased, P < 0.01 | / |
| Group A1-3 | 14 ± 2 | Decreased, P < 0.01 | Decreased, P < 0.01 | / |
| Group M1-1 | 5 ± 1 | Decreased, P < 0.01 | Decreased, P < 0.01 | / |
| Group P1-3 | 16 ± 2 | Decreased, P < 0.01 | Decreased, P < 0.01 | / |
| Group M1-5 | 11 ± 1 | Decreased, P < 0.01 | Decreased, P < 0.01 | / |
| Group R1-5 | 17 ± 2 | Decreased, P < 0.01 | Decreased, P < 0.01 | / |
| Group D5-4 | 12 ± 2 | Decreased, P < 0.01 | Decreased, P < 0.01 | / |
| Group S1-6 | 8 ± 1 | Decreased, P < 0.01 | Decreased, P < 0.01 | / |
| Group S6-6 | 9 ± 2 | Decreased, P < 0.01 | Decreased, P < 0.01 | / |
| Group P1-1 | 7 ± 2 | Decreased, P < 0.01 | Decreased, P < 0.01 | / |

*Only four groups of compounds (B1-1, C1-1, D1-1, and G1-1) were compared with the prototype compounds of corresponding structures (i.e., styryl sulfones 3B, 3C, 3D, and 3G)

It can be seen that compared with the model group, all the compounds showed a statistically significant decrease in the number of microglial cells with CD11b positive expression, demonstrating that these compounds have a definite inhibitory effect on the increase of number of hippocampus microglial cell with CD11b positive expression in the Parkinson's disease model mouse. Compared with the positive control CAPE, all the compounds had a significant decrease in the number of microglial cells with CD11b positive expression, demonstrating that the inhibitory effect of these compounds on the increase of number of hippocampus microglial cell with CD11b positive expression in the Parkinson's disease model mouse were stronger than that of the positive control CAPE. The numbers of positive cells of the four groups of compounds B1-1, C1-1, D1-1, and G1-1 were significantly lower compared with those of the styryl sulfone prototype compounds 3B, 3C, 3D, and 3G, demonstrating that compared with the prototype compounds without the introduction of carbamate functional group, the inhibitory effect of these compounds on the increase of number of hippocampus microglial cell with CD11b positive expression in the Parkinson's disease model mouse was significantly enhanced.

Example 34: Study on the Neuroprotection Mechanism of the Target Compounds in the Parkinson's Disease Model Mouse (i.e., the Inhibitory Effect on the Glial Cell Activation, Using Substantia Nigra GFAP as the Evaluation Indicator)

1. Experiment Principle

Identical to that of Example 31.

2. Experiment Method

Half of experiment mice in each group were taken to separate the midbrain after perfusion and fixation. The tissue was trimmed, and the substantia nigra area was taken to prepare paraffin sections. The GFAP immunohistochemical staining was performed for the statistics of the change in the number of astrocytes with GFAP positive expression. The experiment included blank control group, MPTP model group, positive control group (caffeic acid phenethyl ester, CAPE), prototype control group (styryl sulfone compounds 3B, 3C, 3D, and 3G, whose structures are shown as above), and target compound group.

3. Experiment Results

The effect of each group on the change in the number of substantia nigra astrocyte with GFAP positive expression in the Parkinson's disease model mouse is shown in the table below:

| Group | Positive cell number | Compared with the model group | Compared with the positive group | Compared with the prototype group* |
|---|---|---|---|---|
| Blank control group | 62 ± 5 | / | / | / |
| MPTP model group | 275 ± 12 | / | / | / |
| Positive control group | 132 ± 8 | Decreased, P < 0.01 | / | / |
| Prototype control group 3B | 121 ± 10 | Decreased, P < 0.01 | Equivalent, P > 0.05 | / |
| Prototype control group 3C | 121 ± 13 | Decreased, P < 0.01 | Equivalent, P > 0.05 | / |

-continued

| Group | Positive cell number | Changes and statistical difference (P value) | | |
|---|---|---|---|---|
| | | Compared with the model group | Compared with the positive group | Compared with the prototype group* |
| Prototype control group 3D | 110 ± 9 | Decreased, P < 0.01 | Decreased, P < 0.01 | / |
| Prototype control group 3G | 130 ± 6 | Decreased, P < 0.01 | Equivalent, P > 0.05 | / |
| Group B1-1 | 88 ± 5 | Decreased, P < 0.01 | Decreased, P < 0.01 | Decreased, P < 0.01 |
| Group C1-1 | 56 ± 4 | Decreased, P < 0.01 | Decreased, P < 0.01 | Decreased, P < 0.01 |
| Group D1-1 | 64 ± 3 | Decreased, P < 0.01 | Decreased, P < 0.01 | Decreased, P < 0.01 |
| Group G1-1 | 76 ± 4 | Decreased, P < 0.01 | Decreased, P < 0.01 | Decreased, P < 0.01 |
| Group E2-2 | 102 ± 5 | Decreased, P < 0.01 | Decreased, P < 0.01 | / |
| Group K3-3 | 96 ± 3 | Decreased, P < 0.01 | Decreased, P < 0.01 | / |
| Group K1-4 | 112 ± 4 | Decreased, P < 0.01 | Decreased, P < 0.01 | / |
| Group P1-7 | 73 ± 5 | Decreased, P < 0.01 | Decreased, P < 0.01 | / |
| Group H2-4 | 93 ± 6 | Decreased, P < 0.01 | Decreased, P < 0.01 | / |
| Group M1-3 | 110 ± 5 | Decreased, P < 0.01 | Decreased, P < 0.01 | / |
| Group L1-4 | 98 ± 4 | Decreased, P < 0.01 | Decreased, P < 0.01 | / |
| Group K1-3 | 86 ± 5 | Decreased, P < 0.01 | Decreased, P < 0.01 | / |
| Group J1-4 | 77 ± 4 | Decreased, P < 0.01 | Decreased, P < 0.01 | / |
| Group A1-3 | 105 ± 6 | Decreased, P < 0.01 | Decreased, P < 0.01 | / |
| Group M1-1 | 59 ± 3 | Decreased, P < 0.01 | Decreased, P < 0.01 | / |
| Group P1-3 | 69 ± 5 | Decreased, P < 0.01 | Decreased, P < 0.01 | / |
| Group M1-5 | 81 ± 4 | Decreased, P < 0.01 | Decreased, P < 0.01 | / |
| Group R1-5 | 90 ± 6 | Decreased, P < 0.01 | Decreased, P < 0.01 | / |
| Group D5-4 | 97 ± 5 | Decreased, P < 0.01 | Decreased, P < 0.01 | / |
| Group S1-6 | 67 ± 5 | Decreased, P < 0.01 | Decreased, P < 0.01 | / |
| Group S6-6 | 78 ± 4 | Decreased, P < 0.01 | Decreased, P < 0.01 | / |
| Group P1-1 | 73 ± 6 | Decreased, P < 0.01 | Decreased, P < 0.01 | / |

*Only four groups of compounds (B1-1, C1-1, D1-1, and G1-1) were compared with the prototype compounds of corresponding structures (i.e., styryl sulfones 3B, 3C, 3D, and 3G)

It can be seen that compared with the model group, all the compounds showed a statistically significant decrease in the number of astrocytes with GFAP positive expression, demonstrating that these compounds have a definite inhibitory effect on the increase of number of substantia nigra astrocyte with GFAP positive expression in the Parkinson's disease model mouse. Compared with the positive control CAPE, all the compounds had a significant decrease in the number of astrocytes with GFAP positive expression, demonstrating that the inhibitory effect of these compounds on the increase of number of substantia nigra astrocyte with GFAP positive expression in the Parkinson's disease model mouse were stronger than that of the positive control CAPE. The numbers of positive cells of the four groups of compounds B1-1, C1-1, D1-1, and G1-1 were significantly lower compared with those of the styryl sulfone prototype compounds 3B, 3C, 3D, and 3G, demonstrating that compared with the prototype compounds without the introduction of carbamate functional group, the inhibitory effect of these compounds on the increase of number of substantia nigra astrocyte with GFAP positive expression in the Parkinson's disease model mouse was significantly enhanced.

Example 35: Study on the Neuroprotection Mechanism of the Target Compounds in the Parkinson's Disease Model Mouse (i.e., the Inhibitory Effect on the Glial Cell Activation, Using Hippocampus GFAP as the Evaluation Indicator)

1. Experiment Principle

Identical to that of Example 31.

2. Experiment Method

Half of experiment mice in each group were taken to separate the midbrain after perfusion and fixation. The tissue was trimmed, and the hippocampus area was taken to prepare paraffin sections. The GFAP immunohistochemical staining was performed for the statistics of the change in the number of astrocytes with GFAP positive expression. The experiment included blank control group, MPTP model group, positive control group (caffeic acid phenethyl ester, CAPE), prototype control group (styryl sulfone compounds 3B, 3C, 3D, and 3G, whose structures are shown as above), and target compound group.

3. Experiment Results

The effect of each group on the change in the number of hippocampus astrocytes with GFAP positive expression in the Parkinson's disease model mouse is shown in the table below:

| Group | Positive cell number | Changes and statistical difference (P value) | | |
|---|---|---|---|---|
| | | Compared with the model group | Compared with the positive group | Compared with the prototype group* |
| Blank control group | 64 ± 3 | / | / | / |
| MPTP model group | 175 ± 10 | / | / | / |
| Positive control group | 86 ± 2 | Decreased, P < 0.01 | / | / |
| Prototype control group 3B | 118 ± 8 | Decreased, P < 0.01 | Increased, P < 0.01 | / |
| Prototype control group 3C | 147 ± 4 | Decreased, P < 0.01 | Increased, P < 0.01 | / |
| Prototype control group 3D | 106 ± 6 | Decreased, P < 0.01 | Increased, P < 0.01 | / |
| Prototype control group 3G | 130 ± 6 | Decreased, P < 0.01 | Increased, P < 0.01 | / |
| Group B1-1 | 64 ± 4 | Decreased, P < 0.01 | Decreased, P < 0.01 | Decreased, P < 0.01 |

-continued

| | | Changes and statistical difference (P value) | | |
|---|---|---|---|---|
| Group | Positive cell number | Compared with the model group | Compared with the positive group | Compared with the prototype group* |
| Group C1-1 | 78 ± 3 | Decreased, P < 0.01 | Decreased, P < 0.01 | Decreased, P < 0.01 |
| Group D1-1 | 58 ± 5 | Decreased, P < 0.01 | Decreased, P < 0.01 | Decreased, P < 0.01 |
| Group G1-1 | 66 ± 4 | Decreased, P < 0.01 | Decreased, P < 0.01 | Decreased, P < 0.01 |
| Group E2-2 | 50 ± 5 | Decreased, P < 0.01 | Decreased, P < 0.01 | / |
| Group K3-3 | 69 ± 3 | Decreased, P < 0.01 | Decreased, P < 0.01 | / |
| Group K1-4 | 71 ± 4 | Decreased, P < 0.01 | Decreased, P < 0.01 | / |
| Group P1-7 | 49 ± 4 | Decreased, P < 0.01 | Decreased, P < 0.01 | / |
| Group H2-4 | 61 ± 5 | Decreased, P < 0.01 | Decreased, P < 0.01 | / |
| Group M1-3 | 57 ± 3 | Decreased, P < 0.01 | Decreased, P < 0.01 | / |
| Group L1-4 | 76 ± 4 | Decreased, P < 0.01 | Decreased, P < 0.01 | / |
| Group K1-3 | 65 ± 5 | Decreased, P < 0.01 | Decreased, P < 0.01 | / |
| Group J1-4 | 79 ± 2 | Decreased, P < 0.01 | Decreased, P < 0.01 | / |
| Group A1-3 | 55 ± 3 | Decreased, P < 0.01 | Decreased, P < 0.01 | / |
| Group M1-1 | 51 ± 5 | Decreased, P < 0.01 | Decreased, P < 0.01 | / |
| Group P1-3 | 74 ± 3 | Decreased, P < 0.01 | Decreased, P < 0.01 | / |
| Group M1-5 | 67 ± 6 | Decreased, P < 0.01 | Decreased, P < 0.01 | / |
| Group R1-5 | 80 ± 2 | Decreased, P < 0.01 | Decreased, P < 0.01 | / |
| Group D5-4 | 59 ± 3 | Decreased, P < 0.01 | Decreased, P < 0.01 | / |
| Group S1-6 | 61 ± 4 | Decreased, P < 0.01 | Decreased, P < 0.01 | / |
| Group S6-6 | 58 ± 2 | Decreased, P < 0.01 | Decreased, P < 0.01 | / |
| Group P1-1 | 72 ± 3 | Decreased, P < 0.01 | Decreased, P < 0.01 | / |

*Only four groups of compounds (B1-1, C1-1, D1-1, and G1-1) were compared with the prototype compounds of corresponding structures (i.e., styryl sulfones 3B, 3C, 3D, and 3G)

It can be seen that compared with the model group, all the compounds showed a statistically significant decrease in the number of astrocytes with GFAP positive expression, demonstrating that these compounds have a definite inhibitory effect on the increase of number of hippocampus astrocytes with GFAP positive expression in the Parkinson's disease model mouse. Compared with the positive control CAPE, all the compounds had a significant decrease in the number of astrocytes with GFAP positive expression, demonstrating that the inhibitory effect of these compounds on the increase of number of hippocampus astrocytes with GFAP positive expression in the Parkinson's disease model mouse were stronger than that of the positive control CAPE. The numbers of positive cells of the four groups of compounds B1-1, C1-1, D1-1, and G1-1 were significantly lower compared with those of the styryl sulfone prototype compounds 3B, 3C, 3D, and 3G, demonstrating that compared with the prototype compounds without the introduction of carbamate functional group, the inhibitory effect of these compounds on the increase of number of hippocampus astrocytes with GFAP positive expression in the Parkinson's disease model mouse was significantly enhanced.

Example 36: Study on the Neuroprotection Mechanism of the Target Compounds in the Parkinson's Disease Model Mouse (i.e., the Inhibitory Effect on the Oxidative Stress Damage, Using HO-1 as the Evaluation Indicator)

1. Experiment Principle

Oxidative stress is an important pathogenic mechanism of PD. Dopaminergic neurons are more sensitive to oxidative stress and are more susceptible to oxidative stress damage. Heme oxygenase (HO-1), a phase II enzyme, is also a well-known antioxidase. It plays an important protective role by catalyzing the conversion of free radicals into non-toxic products and increasing their water solubility to facilitate the elimination of free radicals, and maintain the redox balance in the body. It plays an important role in the process of protecting cells against oxidative stress damage. The activation of p38 protein phosphorylation has a negative regulatory effect on phase II enzymes. Studies have found that in PD mouse models and cell models, the expression of NADPH oxidase is down-regulated by inhibiting the activation of p38, which can up-regulate the expression of HO-1 and resist oxidative damage. Using HO-1 as an indicator, the inhibitory effect of the target compounds on MPTP-induced oxidative stress damage in PD mice can be investigated.

2. Experiment Method

HO-1 is expressed in astrocytes, microglial cells, and neurons. The total proteins of the midbrain tissue of mice in each experiment group were extracted, to determine the expression of phase II enzyme HO-1 in the midbrain of mice by western blot using GAPDH as the internal reference. The experiment included blank control group, MPTP model group, positive control group (caffeic acid phenethyl ester, CAPE), prototype control group (styryl sulfone compounds 3B, 3C, 3D, and 3G, whose structures are shown as above), and target compound group.

3. Experiment Results

The effect of each group on the change in the midbrain HO-1 expression in the Parkinson's disease model mouse is shown in the table below:

| | | Changes and statistical difference (P value) | | |
|---|---|---|---|---|
| Group | Expression (HO-1/GAPDH) | Compared with the model group | Compared with the positive group | Compared with the prototype group* |
| Blank control group | 0.76 ± 0.06 | / | / | / |
| MPTP model group | 0.48 ± 0.03 | / | / | / |

-continued

| Group | Expression (HO-1/GAPDH) | Compared with the model group | Compared with the positive group | Compared with the prototype group* |
|---|---|---|---|---|
| Positive control group | 0.52 ± 0.07 | Equivalent, P > 0.05 | / | / |
| Prototype control group 3B | 0.56 ± 0.03 | Increased, P < 0.01 | Equivalent, P > 0.05 | / |
| Prototype control group 3C | 0.44 ± 0.05 | Equivalent, P > 0.05 | Equivalent, P > 0.05 | / |
| Prototype control group 3D | 1.03 ± 0.20 | Increased, P < 0.01 | Increased, P < 0.01 | / |
| Prototype control group 3G | 0.51 ± 0.07 | Equivalent, P > 0.05 | Equivalent, P > 0.05 | / |
| Group B1-1 | 0.90 ± 0.10 | Increased, P < 0.01 | Increased, P < 0.01 | Increased, P < 0.01 |
| Group C1-1 | 0.88 ± 0.09 | Increased, P < 0.01 | Increased, P < 0.01 | Increased, P < 0.01 |
| Group D1-1 | 1.63 ± 0.12 | Increased, P < 0.01 | Increased, P < 0.01 | Increased, P < 0.01 |
| Group G1-1 | 1.35 ± 0.10 | Increased, P < 0.01 | Increased, P < 0.01 | Increased, P < 0.01 |
| Group E2-2 | 1.58 ± 0.08 | Increased, P < 0.01 | Increased, P < 0.01 | / |
| Group K3-3 | 0.69 ± 0.07 | Increased, P < 0.01 | Increased, P < 0.01 | / |
| Group K1-4 | 1.02 ± 0.09 | Increased, P < 0.01 | Increased, P < 0.01 | / |
| Group P1-7 | 0.71 ± 0.09 | Increased, P < 0.01 | Increased, P < 0.01 | / |
| Group H2-4 | 0.95 ± 0.10 | Increased, P < 0.01 | Increased, P < 0.01 | / |
| Group M1-3 | 0.80 ± 0.09 | Increased, P < 0.01 | Increased, P < 0.01 | / |
| Group L1-4 | 1.13 ± 0.12 | Increased, P < 0.01 | Increased, P < 0.01 | / |
| Group K1-3 | 0.83 ± 0.08 | Increased, P < 0.01 | Increased, P < 0.01 | / |
| Group J1-4 | 1.25 ± 0.06 | Increased, P < 0.01 | Increased, P < 0.01 | / |
| Group A1-3 | 0.66 ± 0.05 | Increased, P < 0.01 | Increased, P < 0.01 | / |
| Group M1-1 | 1.29 ± 0.07 | Increased, P < 0.01 | Increased, P < 0.01 | / |
| Group P1-3 | 0.77 ± 0.10 | Increased, P < 0.01 | Increased, P < 0.01 | / |
| Group M1-5 | 0.96 ± 0.08 | Increased, P < 0.01 | Increased, P < 0.01 | / |
| Group R1-5 | 0.87 ± 0.06 | Increased, P < 0.01 | Increased, P < 0.01 | / |
| Group D5-4 | 0.93 ± 0.10 | Increased, P < 0.01 | Increased, P < 0.01 | / |
| Group S1-6 | 0.85 ± 0.06 | Increased, P < 0.01 | Increased, P < 0.01 | / |
| Group S6-6 | 1.08 ± 0.11 | Increased, P < 0.01 | Increased, P < 0.01 | / |
| Group P1-1 | 1.17 ± 0.05 | Increased, P < 0.01 | Increased, P < 0.01 | / |

*Only four groups of compounds (B1-1, C1-1, D1-1, and G1-1) were compared with the prototype compounds of corresponding structures (i.e., styryl sulfones 3B, 3C, 3D, and 3G)

It can be seen that compared with the model group, all the compounds showed a statistically significant increase in terms of the HO-1 expression, demonstrating that these compounds have a definite up-regulation effect on the midbrain HO-1 expression in the Parkinson's disease model mouse, and were beneficial for the resistance against oxidative damage. Compared with the positive control CAPE, all the compounds had a significant increase in the HO-1 expression, demonstrating that the up-regulation effects of these compounds on the midbrain HO-1 expression in the Parkinson's disease model mouse were stronger than that of the positive control CAPE, and have better resistance against oxidative damage. The expressions of the four groups of compounds B1-1, C1-1, D1-1, and G1-1 were significantly higher compared with those of the styryl sulfone prototype compounds 3B, 3C, 3D, and 3G, demonstrating that compared with the prototype compounds without the introduction of carbamate functional group, the up-regulation effect of these compounds on the midbrain HO-1 expression in the Parkinson's disease model was significantly enhanced.

Example 37: Study on the Neuroprotection Mechanism of the Target Compounds in the Parkinson's Disease Model Mouse (i.e., the Inhibitory Effect on the Oxidative Stress Damage, Using GCLC as the Evaluation Indicator)

1. Experiment Principle

Oxidative stress is an important pathogenic mechanism of PD. Dopaminergic neurons are more sensitive to oxidative stress and are more susceptible to oxidative stress damage. Glutathione (GSH) is an important antioxidant substance in the cell, and glutamate cysteine ligase (GCL) is the rate-limiting enzyme for GSH synthesis, which is composed of catalytic subunit (GCLC) and regulatory subunit (GCLM). The increase of GCLC expression can promote the synthesis of GSH and enhance the ability of tissue cells against oxidative stress. GCL, a phase II enzyme, plays an important protective role by catalyzing the conversion of free radicals into non-toxic products and increasing their water solubility to facilitate the elimination of free radicals, and maintain the redox balance in the body. It plays an important role in the process of protecting cells against oxidative stress damage. The activation of p38 protein phosphorylation has a negative regulatory effect on phase II enzymes. Studies have found that in PD mouse models and cell models, the expression of NADPH oxidase is down-regulated by inhibiting the activation of p38, which can up-regulate the expression of GCLC and resist oxidative damage. Using GCLC as an indicator, the inhibitory effect of the target compounds on MPTP-induced oxidative stress damage in PD mice can be investigated.

2. Experiment Method

GCLC is expressed in astrocytes, microglial cells, and neurons. The total proteins of the midbrain tissue of mice in each experiment group were extracted, to determine the expression of phase II enzyme GCLC in the midbrain of mice by western blot using GAPDH as the internal reference. The experiment included blank control group, MPTP model group, positive control group (caffeic acid phenethyl ester, CAPE), prototype control group (styryl sulfone compounds 3B, 3C, 3D), and 3G, whose structures are shown as above), and target compound group.

3. Experiment Results

The effect of each group on the change in the midbrain GCLC expression in the Parkinson's disease model mouse is shown in the table below:

| Group | Expression (GCLC/GAPDH) | Changes and statistical difference (P value) | | |
|---|---|---|---|---|
| | | Compared with the model group | Compared with the positive group | Compared with the prototype group* |
| Blank control group | 1.26 ± 0.12 | / | / | / |
| MPTP model group | 0.37 ± 0.04 | / | / | / |
| Positive control group | 0.77 ± 0.06 | Increased, $P < 0.01$ | / | / |
| Prototype control group 3B | 0.33 ± 0.04 | Equivalent, $P > 0.05$ | Decreased, $P < 0.01$ | / |
| Prototype control group 3C | 0.34 ± 0.05 | Equivalent, $P > 0.05$ | Decreased, $P < 0.01$ | / |
| Prototype control group 3D | 0.53 ± 0.04 | Increased, $P < 0.01$ | Decreased, $P < 0.01$ | / |
| Prototype control group 3G | 0.57 ± 0.09 | Increased, $P < 0.01$ | Decreased, $P < 0.01$ | / |
| Group B1-1 | 1.17 ± 0.06 | Increased, $P < 0.01$ | Increased, $P < 0.01$ | Increased, $P < 0.01$ |
| Group C1-1 | 1.34 ± 0.08 | Increased, $P < 0.01$ | Increased, $P < 0.01$ | Increased, $P < 0.01$ |
| Group D1-1 | 1.29 ± 0.05 | Increased, $P < 0.01$ | Increased, $P < 0.01$ | Increased, $P < 0.01$ |
| Group G1-1 | 1.05 ± 0.04 | Increased, $P < 0.01$ | Increased, $P < 0.01$ | Increased, $P < 0.01$ |
| Group E2-2 | 1.48 ± 0.11 | Increased, $P < 0.01$ | Increased, $P < 0.01$ | / |
| Group K3-3 | 0.86 ± 0.04 | Increased, $P < 0.01$ | Increased, $P < 0.05$ | / |
| Group K1-4 | 1.10 ± 0.07 | Increased, $P < 0.01$ | Increased, $P < 0.01$ | / |
| Group P1-7 | 0.87 ± 0.08 | Increased, $P < 0.01$ | Increased, $P < 0.05$ | / |
| Group H2-4 | 1.21 ± 0.08 | Increased, $P < 0.01$ | Increased, $P < 0.01$ | / |
| Group M1-3 | 0.82 ± 0.07 | Increased, $P < 0.01$ | Increased, $P < 0.05$ | / |
| Group L1-4 | 0.96 ± 0.10 | Increased, $P < 0.01$ | Increased, $P < 0.01$ | / |
| Group K1-3 | 1.13 ± 0.08 | Increased, $P < 0.01$ | Increased, $P < 0.01$ | / |
| Group J1-4 | 1.24 ± 0.10 | Increased, $P < 0.01$ | Increased, $P < 0.01$ | / |
| Group A1-3 | 0.84 ± 0.04 | Increased, $P < 0.01$ | Increased, $P < 0.05$ | / |
| Group M1-1 | 1.30 ± 0.09 | Increased, $P < 0.01$ | Increased, $P < 0.01$ | / |
| Group P1-3 | 0.91 ± 0.11 | Increased, $P < 0.01$ | Increased, $P < 0.05$ | / |
| Group M1-5 | 1.35 ± 0.08 | Increased, $P < 0.01$ | Increased, $P < 0.01$ | / |
| Group R1-5 | 1.02 ± 0.09 | Increased, $P < 0.01$ | Increased, $P < 0.01$ | / |
| Group D5-4 | 0.97 ± 0.07 | Increased, $P < 0.01$ | Increased, $P < 0.01$ | / |
| Group S1-6 | 1.44 ± 0.13 | Increased, $P < 0.01$ | Increased, $P < 0.01$ | / |
| Group S6-6 | 1.29 ± 0.08 | Increased, $P < 0.01$ | Increased, $P < 0.01$ | / |
| Group P1-1 | 0.98 ± 0.06 | Increased, $P < 0.01$ | Increased, $P < 0.01$ | / |

*Only four groups of compounds (B1-1, C1-1, D1-1, and G1-1) were compared with the prototype compounds of corresponding structures (i.e., styryl sulfones 3B, 3C, 3D, and 3G).

It can be seen that compared with the model group, all the compounds showed a statistically significant increase in terms of the GCLC expression, demonstrating that these compounds have a definite up-regulation effect on the midbrain GCLC expression in the Parkinson's disease model mouse, and were beneficial for the resistance of oxidative damage. Compared with the positive control CAPE, all the compounds had a relatively significant or significant increase in the GCLC expression, demonstrating that the up-regulation effects of these compounds on the midbrain GCLC expression in the Parkinson's disease model mouse were stronger than that of the positive control CAPE, and have better resistance against oxidative damage. The expressions of the four groups of compounds B1-1, C1-1, D1-1, and G1-1 were significantly higher compared with those of the styryl sulfone prototype compounds 3B, 3C, 3D), and 3G, demonstrating that compared with the prototype compounds without the introduction of carbamate functional group, the up-regulation effects of these compounds on the midbrain GCLC expression in the Parkinson's disease model was significantly enhanced.

Example 38: Evaluation of the Inhibitory Activity of the Target Compounds on Cholinesterase (Using IC50 Value of Acetylcholinesterase as the Evaluation Indicator)

1. Experiment Principle

The central cholinergic system is an important part of the central nervous system. Acetylcholine (ACh) and butyrylcholine (BCh) are important neurotransmitters synthesized and secreted by central cholinergic neurons, which specifically act on various types of cholinergic receptors and play an important role in regulating synaptic plasticity and learning and memory functions. Therefore, the dysfunction of metabolic function such as neurotransmitter synthesis, release, and uptake or the destroying of cholinergic receptors and post-receptor signaling can lead to the hypofunction of the learning and memory function. Studies have shown that the activity of choline transferase decreases in the cortex such as frontal lobe, temporal lobe, parietal lobe, and right hippocampus of PD patient, and cholinergic neuron damage may be the main biochemical mechanism of PD cognitive dysfunction and dementia. By evaluating the inhibitory activities of the target compounds on the two cholinesterases, their potential therapeutic effect on PD cognitive dysfunction and dementia can be evaluated.

2. Experiment Method

The modified Ellman method was used to determine the inhibitory activity on acetylcholinesterase. The principle lies in that acetylthiocholine iodide is decomposed under the action of acetylcholinesterase (AchE) to generate thiocholine. The thiocholine is quickly reacted with DTNB as the colour-developing agent to generate a yellow substance with light absorption at 405 nm. To a 96-well microplate, 50 μl of enzyme reaction buffer, 125 μl of DTNB (3 mM), 25 μl of test sample or positive control drug, and 25 μl of AchE (0.2 U/ml) were successively added. After incubation at room temperature for 5 min, 25 μl of ATCI (15 mM) was added. After incubation at room temperature for 8 min, the absorbance value was determined at 405 nm with a microplate reader. A blank control group without enzyme (25 μl PBS instead of the sample to be tested) was also established. The inhibition percentage was calculated based on the measurement results, using the negative logarithm of the molar concentration of the corresponding compound as the abscissa and the enzyme inhibition rate as the ordinate to obtain a linear equation. When the inhibition rate is 50%, the molar concentration of the compound, i.e., the $IC_{50}$ value of the compound, was calculated. The experiment included blank control group, CAPE control group, prototype control group (styryl sulfone compounds 3B, 3C, 3D, and 3G, whose structures are shown as above), positive drug control group (Rivastigmine), and target compound group.

3. Experiment Results

The inhibitory effect of each group on the acetylcholinesterase is shown in the table below:

| Group | IC$_{50}$ (μM) |
| --- | --- |
| CAPE control group | >100 |
| Prototype control group 3B | >100 |
| Prototype control group 3C | >100 |
| Prototype control group 3D | >100 |
| Prototype control group 3G | >100 |
| Positive drug control group | 53.38 ± 3.14 |
| Group B1-1 | 13.34 ± 2.85 |
| Group C1-1 | 14.66 ± 3.51 |
| Group D1-1 | 4.16 ± 1.07 |
| Group G1-1 | 10.76 ± 2.13 |
| Group E2-2 | 51.28 ± 3.94 |
| Group K3-3 | 38.26 ± 2.79 |
| Group K1-4 | 16.89 ± 1.22 |
| Group P1-7 | 21.38 ± 2.07 |
| Group H2-4 | 11.25 ± 1.34 |
| Group M1-3 | 17.56 ± 2.19 |
| Group L1-4 | 9.48 ± 1.34 |
| Group K1-3 | 22.31 ± 3.17 |
| Group J1-4 | 8.54 ± 1.65 |
| Group A1-3 | 25.16 ± 3.34 |
| Group M1-1 | 6.60 ± 0.71 |
| Group P1-3 | 14.39 ± 2.04 |
| Group M1-5 | 31.27 ± 4.63 |
| Group R1-5 | 27.51 ± 3.49 |
| Group D5-4 | 20.77 ± 3.12 |
| Group S1-6 | 13.64 ± 2.16 |
| Group S6-6 | 15.56 ± 3.07 |
| Group P1-1 | 11.27 ± 1.48 |

It can be seen that all the compounds have IC$_{50}$ values of less than 100 μM, demonstrating that these compounds have a definite inhibitory effect on acetylcholinesterase; while the IC$_{50}$ values in the CAPE control group and prototype control group were both greater than 100 μM, demonstrating that these compounds do not have a definite inhibitory effect. The inhibitory effect of the designed compound on acetylcholinesterase is derived from the newly introduced carbamate functional group. Compared with the positive control drug group, all the compounds have lower IC$_{50}$ values, demonstrating that the inhibitory effect of these compounds on acetylcholinesterase is stronger than that of the positive control drug.

What is claimed is:

1. A compound of general formula I or pharmaceutically acceptable salts thereof:

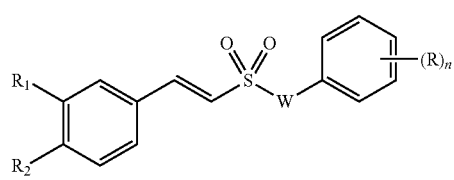

I wherein, at least one of $R_1$ and $R_2$ is independently selected from: carbamoyloxy unsubstituted or substituted by one or two $R_3$; the other one of $R_1$ and $R_2$ is independently selected from: carbamoyloxy unsubstituted or substituted by one or two $R_3$, $C_{1-6}$ alkoxy unsubstituted or substituted by one to six halogen, —N(R$_4$)$_2$ or —OR$_5$; $C_{1-6}$ alkylacyloxy or $C_{7-10}$ arylacyloxy unsubstituted or substituted by one to six halogen, —N(R$_4$)$_2$ or —OR$_5$, sulfonyloxy substituted by $C_{1-3}$ alkyl or $C_{6-8}$ aryl; —OSi(R$_6$)$_3$, and —OH;

W is $C_{1-6}$ alkylene or $C_{2-6}$ alkenylene unsubstituted or substituted by one to three halogen, nitro, $C_{1-6}$ alkyl, —N(R$_4$)$_2$ or —OR$_5$;

each R is independently selected from: halogen; nitro; —OR$_7$; —N(R$_4$)$_2$; and $C_{1-6}$ alkyl, $C_{6-10}$ aryl or $C_{5-9}$ heteroaryl, unsubstituted or substituted by one to six halogen, nitro, —N(R$_4$)$_2$ or —OR$_5$;

n is an integer from 0 to 5;

wherein, each $R_3$ is independently selected from: $C_{1-6}$ saturated alkyl, $C_{2-4}$ alkenyl, $C_{2-4}$ alkynyl, $C_{6-10}$ aryl, $C_{5-9}$ heteroaryl, $C_{1-6}$ alkylacyl or $C_{7-10}$ arylacyl, unsubstituted or substituted by one to six halogen, nitro, —N(R$_4$)$_2$ or —OR$_5$; sulfonyl substituted by $C_{1-3}$ alkyl or $C_{6-8}$ aryl; or two $R_3$ together with the nitrogen atom to which they are attached form a 5- to 7-membered nitrogen-containing saturated heterocyclyl, provided that at least one of $R_1$ and $R_2$ is carbamoyloxy substituted by two $R_3$, the 5- to 7-membered nitrogen-containing saturated heterocyclyl is unsubstituted or substituted by one or two $R_6$;

each $R_4$ is independently —H or $C_{1-6}$ saturated alkyl;

each $R_5$ is independently selected from —H, $C_{1-6}$ saturated alkyl, $C_{2-4}$ alkenyl, $C_{6-10}$ aryl, and $C_{5-9}$ heteroaryl;

each $R_6$ is independently selected from $C_{1-6}$ alkyl, $C_{1-6}$ alkoxy and $C_{6-8}$ aryl, unsubstituted or substituted by one to six halogen;

each $R_7$ is independently selected from H; $C_{1-6}$ saturated alkyl, $C_{2-4}$ alkenyl, $C_{2-4}$ alkynyl, $C_{6-10}$ aryl, $C_{5-9}$ heteroaryl, $C_{1-6}$ alkylacyl or $C_{7-10}$ arylacyl, unsubstituted or substituted by one to six halogen, N(R$_4$)$_2$ or OR$_5$; sulfonyl substituted by $C_{1-3}$ alkyl or $C_{6-8}$ aryl; and Si(R$_6$)$_3$.

2. The compound or pharmaceutically acceptable salts thereof according to claim 1, characterized in that: at least one of $R_1$ and $R_2$ is independently selected from carbamoyloxy unsubstituted or substituted by one or two $R_3$; the other one of $R_1$ and $R_2$ is independently selected from: carbamoyloxy unsubstituted or substituted by one or two $R_3$; $C_{1-6}$ alkoxy unsubstituted or substituted by one to six halogen or OR$_5$; $C_{1-6}$ alkylacyloxy unsubstituted or substituted by —N(R$_4$)$_2$ or —OR$_5$; sulfonyloxy substituted by $C_{1-3}$ alkyl or $C_{6-8}$ aryl; and —OSi(R$_6$)$_3$.

3. The compound or pharmaceutically acceptable salts thereof according to claim 1, characterized in that: W is $C_{1-6}$ alkylene or $C_{2-6}$ alkenylene unsubstituted or substituted by one or two halogen, nitro, $C_{1-6}$ alkyl or —OR$_5$.

4. The compound or pharmaceutically acceptable salts thereof according to claim 1, characterized in that: each R is independently selected from: halogen; nitro; —OR$_7$; —N(R$_4$)$_2$; and $C_{1-6}$ alkyl or $C_{6-10}$ aryl unsubstituted or substituted by one to six halogen, nitro or —OR$_5$.

5. The compound or pharmaceutically acceptable salts thereof according to claim 1, characterized in that: n is an integer from 0 to 3.

6. The compound or pharmaceutically acceptable salts thereof according to claim 1, characterized in that: at least one of $R_1$ and $R_2$ is independently selected from carbamoyloxy unsubstituted or substituted by one or two $R_3$; the other one of $R_1$ and $R_2$ is independently selected from: carbamoyloxy unsubstituted or substituted by one or two $R_3$; $C_{1-6}$ alkoxy unsubstituted or substituted by one to six halogen or OR$_5$; C$_{1-6}$ alkylacyloxy unsubstituted or substituted by —N(R$_4$)$_2$ or —OR$_5$; sulfonyloxy substituted by C$_{1-3}$ alkyl or C$_{6-8}$ aryl; and —OSi(R$_6$)$_3$;

W is C$_{1-6}$ alkylene or C$_{2-6}$ alkenylene unsubstituted or substituted by one or two halogen, nitro, C$_{1-6}$ alkyl or —OR$_5$;

each R is independently selected from: halogen; nitro, —OR$_7$; —N(R$_4$)$_2$; and C$_{1-6}$ alkyl or C$_{6-10}$ aryl unsubstituted or substituted by one to six halogen, nitro or —OR$_5$;

n is an integer from 0 to 3;

wherein each R$_3$ is independently selected from: C$_{1-6}$ saturated alkyl, C$_{6-10}$ aryl or C$_{5-9}$ heteroaryl, unsubstituted or substituted by one to six halogen, nitro, —N(R$_4$)$_2$ or —OR$_5$; and sulfonyl substituted by C$_{1-3}$ alkyl or C$_{6-8}$ aryl.

7. A method for preparing a compound of general formula I according to claim 1, comprising:

a) reacting a compound of general formula II with solid phosgene under an alkaline condition to produce a compound of general formula III;

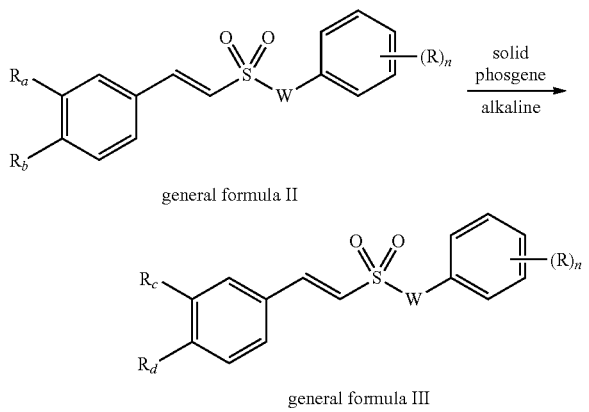

b) reacting the compound of general formula III with NH$_3$, R$_3$NH$_2$ or (R$_3$)$_2$NH to produce the compound of general formula I, and

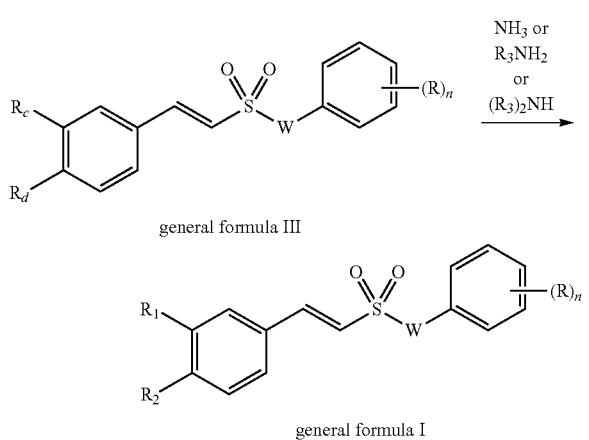

c) optionally, converting the compound of general formula I into its pharmaceutically acceptable salt; wherein at least one of R$_a$ and R$_b$ is independently —OH; the other one of R$_a$ and R$_b$ is independently selected from: —OH; C$_{1-6}$ alkoxy unsubstituted or substituted by one to six halogen, —N(R$_4$)$_2$ or —OR$_5$; C$_{1-6}$ alkylacyloxy or C$_{7-10}$ arylacyloxy unsubstituted or substituted by one to six halogen, —N(R$_4$)$_2$ or —OR$_5$; sulfonyloxy substituted by C$_{1-3}$ alkyl or C$_{6-8}$ aryl; and —OSi(R$_6$)$_3$;

at least one of R$_c$ and R$_d$ is independently —OCOCl; the other one of R$_c$ and R$_d$ is independently selected from —OCOCl; C$_{1-6}$ alkoxy unsubstituted or substituted by one to six halogen, —N(R$_4$)$_2$ or —OR$_5$; C$_{1-6}$ alkylacyloxy or C$_{7-10}$ arylacyloxy unsubstituted or substituted by one to six halogen, —N(R$_4$)$_2$ or —OR$_5$; sulfonyloxy substituted by C$_{1-3}$alkyl or C$_{6-8}$aryl; —OSi(R$_6$)$_3$; and —OH;

wherein the definitions for W, R, n, R$_3$, R$_4$, R$_5$, and R$_6$ are as recited in any claim 1.

8. A pharmaceutical composition, comprising a compound of general formula I or pharmaceutically acceptable salts thereof according to claim 1, as well as at least one pharmaceutically acceptable carrier.

9. A method for treating Parkinson's disease, comprising administrating a compound of general formula I or pharmaceutically acceptable salts thereof according to claim 1 or a pharmaceutical composition according to claim 8 to a patient in need thereof.

10. The compound or pharmaceutically acceptable salts thereof according to claim 1, wherein at least one of R$_1$ and R$_2$ is independently selected from carbamoyloxy, N-methylcarbamoyloxy, N,N-dimethylcarbamoyloxy, N,N-diethylcarbamoyloxy, N-methyl-N-ethylcarbamoyloxy, N-methyl-N-(2-methoxyethyl)carbamoyloxy, N-(5-methyl-2-nitroanilino)carbamoyloxy, N-(2-methyl-5-nitroanilino)carbamoyloxy, N-(p-methoxyphenyl)carbamoyloxy, N-(p-methylaminophenyl)carbamoyloxy, N-methyl-N-phenylcarbamoyloxy, N-methyl-N-p-chlorophenylcarbamoyloxy, N-methyl-N-p-bromophenylcarbamoyloxy, N-methyl-N-p-iodophenylcarbamoyloxy, N-thienylcarbamoyloxy, N-furylcarbamoyloxy, N-methyl-N-mesylcarbamoyloxy, and N-methyl-N-p-tosylcarbamoyloxy;

the other one of R$_1$ and R$_2$ is independently selected from carbamoyloxy, N-methylcarbamoyloxy, N,N-dimethylcarbamoyloxy, N,N-diethylcarbamoyloxy, N-methyl-N-ethylcarbamoyloxy, N-methyl-N-(2-methoxyethyl)carbamoyloxy, N-(5-methyl-2-nitroanilino) carbamoyloxy, N-(2-methyl-5-nitroanilino) carbamoyloxy, N-(p-methoxyphenyl)carbamoyloxy, N-(p-methylaminophenyl)carbamoyloxy, N-methyl-N-phenylcarbamoyloxy, N-methyl-N-p-chlorophenylcarbamoyloxy, N-methyl-N-p-bromophenylcarbamoyloxy, N-methyl-N-p-iodophenylcarbamoyloxy, N-thienylcarbamoyloxy, N-furylcarbamoyloxy, N-methyl-N-mesylcarbamoyloxy, and N-methyl-N-p-tosylcarbamoyloxy, or selected from methoxy, ethoxy, t-butoxy, trifluoromethoxy, 2,3-dibromobutoxy, 2-methoxyethoxy, 2-benzyloxyethoxy, acetyloxy, propionyloxy, pivaloyloxy, methoxyacetyloxy, 4-methoxybutyryloxy, 3-aminopropionyloxy, 2-aminopropionyloxy, mesyloxy, ethylsulfonyloxy, p-tosyloxy, trimethylsiloxy, triphenylsiloxy, chloromethyl(dimethyl)siloxy, and dimethoxy(phenyl)siloxy.

11. The compound or pharmaceutically acceptable salts thereof according to claim 1, wherein W is selected from —CH$_2$—, —CH$_2$CH$_2$—, —CH$_2$CH$_2$CH$_2$—, —CH(F)—, —CH(Cl)—, —CH(Br)—, —CF$_2$—, —CH(Cl)CH$_2$—, —CH$_2$CH(Cl)—, —CH(Cl)CH(Cl)—, —CH$_2$CH(Cl)CH$_2$—, —CH(NO$_2$)—, —CH$_2$CH(NO$_2$)—, —CH$_2$CH (NO₂)CH₂—, —CH(CH₃)—, —CH(CH₃)CH₂—, —CH(OCH₃)—, —CH₂CH(OCH₂CH₃)CH(OCH₂CH₃)—, —CH₂CH(OCH₂C₆H₅)CH₂—, —CH₂CH(OH)—, —CH═CH—, —CH₂CH═CHCH₂—, —CH═CHCH₂—, —CH═C(CH₃)—, and —CH(Cl)CH═CHCH₂—.

12. The compound or pharmaceutically acceptable salts thereof according to claim 1, wherein each R is independently selected from fluoro, chloro, bromo, iodo, nitro, hydroxy, methoxy, ethoxy, isopropoxy, t-butoxy, 2,2,2-trifluoroethoxy, 2-methylaminoethoxy, N,N-dimethylaminomethoxy, allyloxy, phenoxy, benzyloxy, p-methylaminobenzyloxy, 3,4-dimethoxybenzyloxy, formyloxy, acetyloxy, dimethylaminoacetyloxy, benzoyloxy, phenylacetyloxy, p-methoxyphenylacetyloxy, trimethylsiloxy, triphenylsiloxy, chloromethyl(dimethyl)siloxy, dimethoxy(phenyl)siloxy, amino, methylamino, ethylamino, diisopropylamino, methyl, ethyl, isopropyl, t-butyl, trifluoromethyl, phenyl, benzyl, phenethyl, p-chlorophenyl, p-nitrophenyl, and 3,4-dimethoxyphenyl.

13. The compound or pharmaceutically acceptable salts thereof according to claim 5, wherein each $R_3$ is independently selected from: $C_{1-6}$ saturated alkyl, $C_{6-10}$ aryl or $C_{5-9}$ heteroaryl, unsubstituted or substituted by one to six halogen, nitro, —N(R₄)₂ or —OR₅; and sulfonyl substituted by $C_{1-3}$ alkyl or $C_{6-8}$ aryl.

14. The compound or pharmaceutically acceptable salts thereof according to claim 1, wherein the compound is selected from the following compounds:

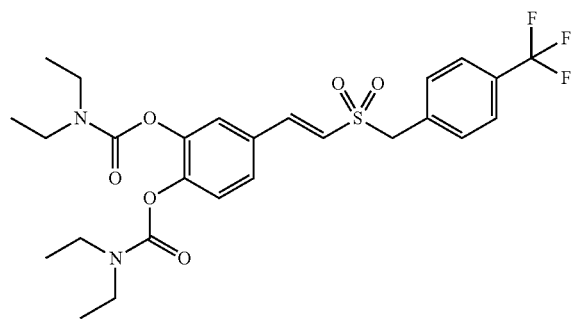

Compound B1-1

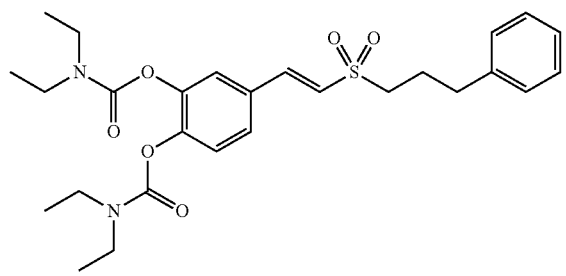

Compound C1-1

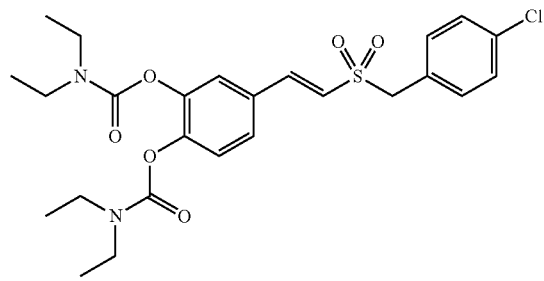

Compound D1-1

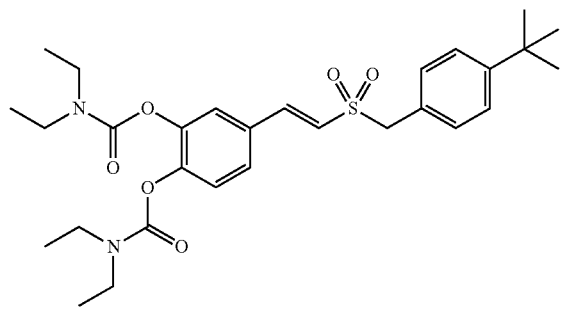

Compound G1-1

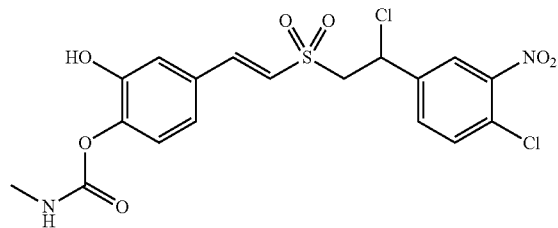

Compound E2-2

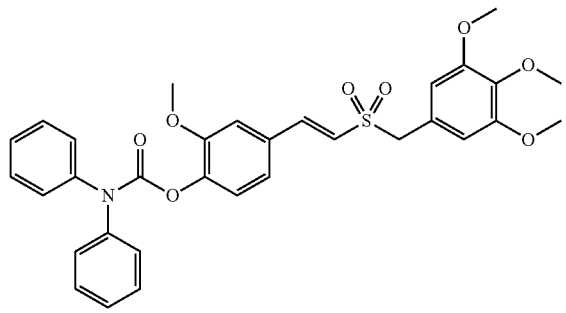

Compound K3-3

-continued
Compound K1-4
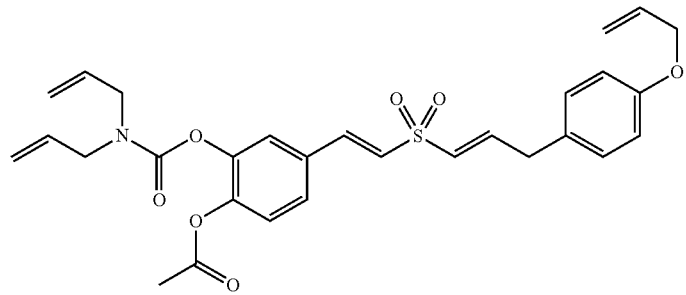
Compound P1-7
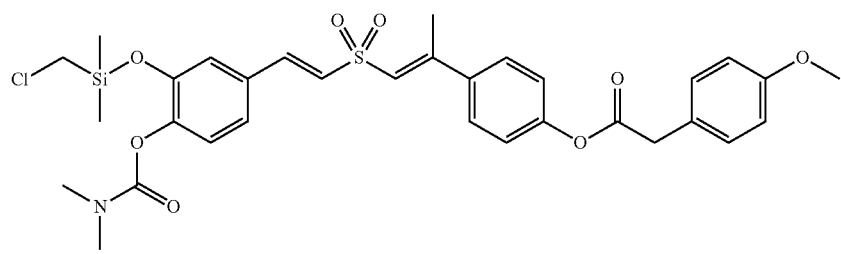
Compound H2-4
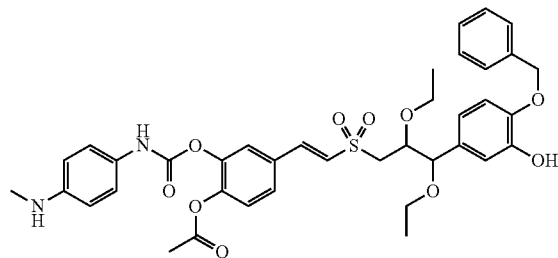
Compound M1-3
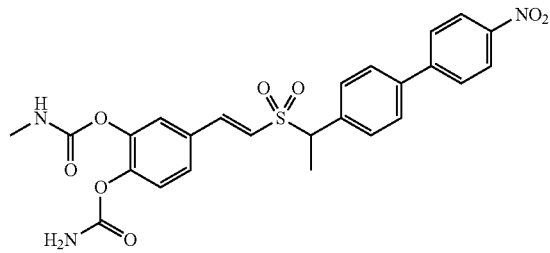
Compound L1-4
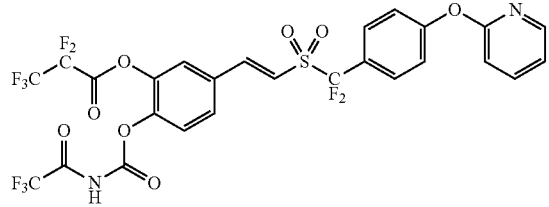
Compound K1-3
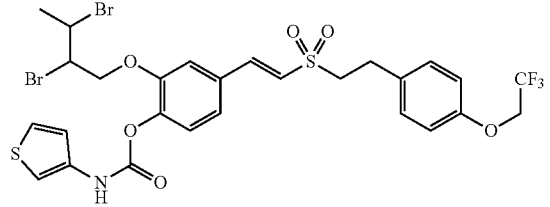
Compound J1-4
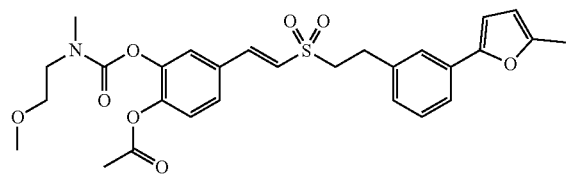
Compound A1-3
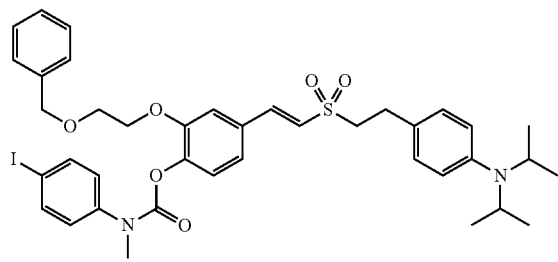

-continued
Compound M1-1
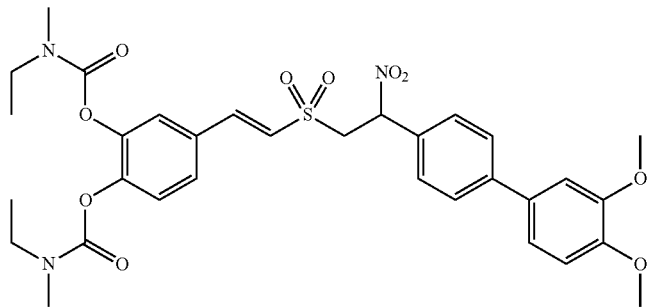
Compound P1-3
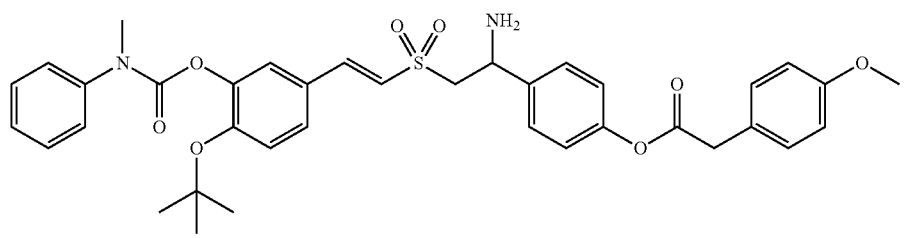
Compound M1-5
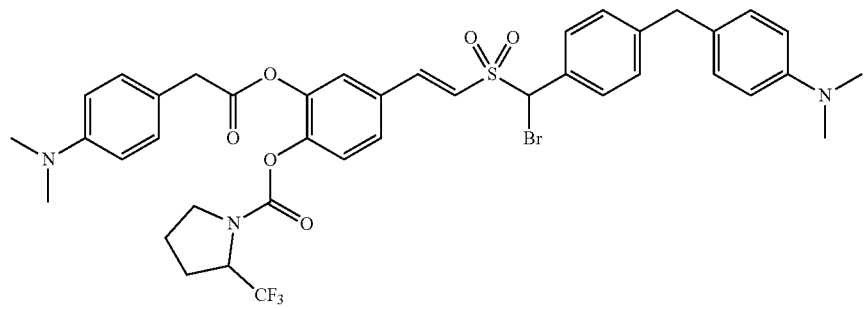
Compound R1-5
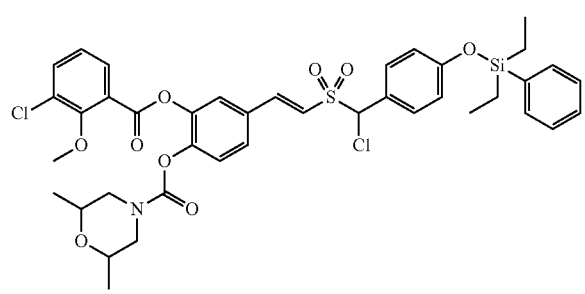
Compound D5-4
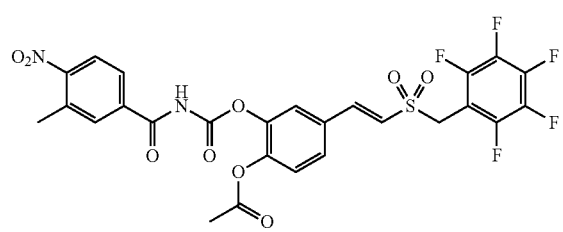
Compound S1-6
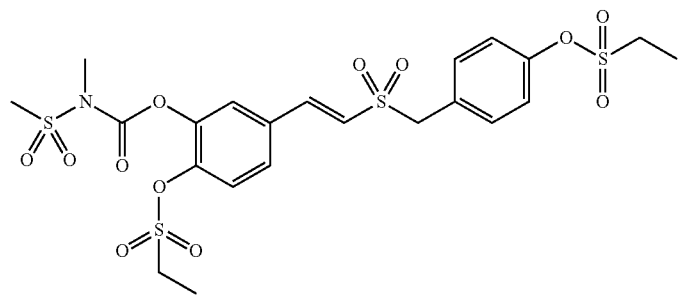

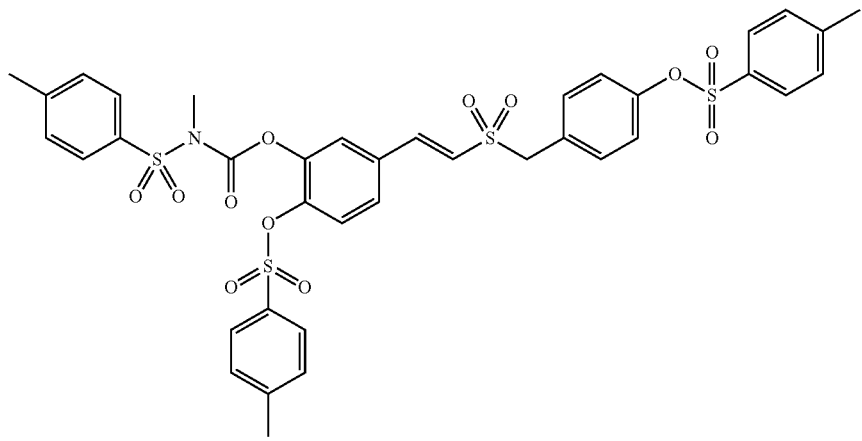

Compound S6-6

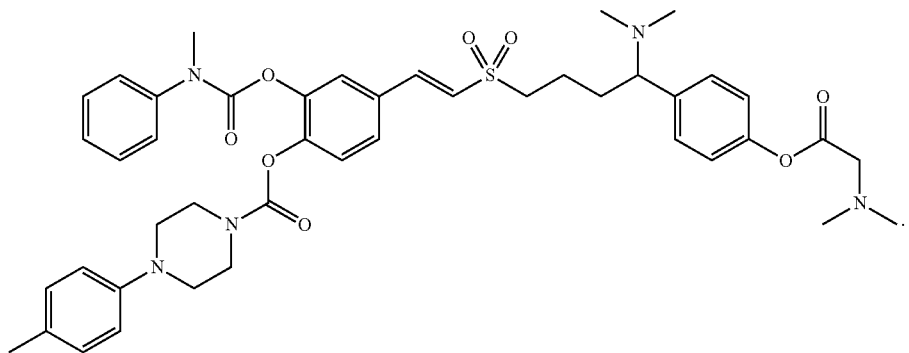

Compound P1-1

15. The method for preparing the compound of general formula I according to claim 7, wherein the base used in step a) is a moderately alkaline or weakly alkaline inorganic or organic base, wherein the inorganic base is selected from one or more of sodium hydroxide, potassium hydroxide, sodium bicarbonate, sodium carbonate, sodium acetate, and cesium carbonate; and the organic base is selected from pyridine, triethylamine, 4-dimethylaminopyridine, DBU (1,8-diazabicycloundec-7-ene), DBN (1,5-diazabicyclo[4.3.0]non-5-ene), and MTBD (7-methyl-1,5,7-triazabicyclo[4.4.0]dec-5-ene).

16. The method for preparing the compound of general formula I according to claim 7, wherein a base or no base is used in the step b), and when a base is used, the base used in the step b) is a moderately alkaline or weakly alkaline inorganic or organic base, wherein the inorganic base is selected from one or more of sodium hydroxide, potassium hydroxide, sodium bicarbonate, sodium carbonate, sodium acetate, and cesium carbonate; and the organic base is selected from pyridine, triethylamine, 4-dimethylaminopyridine, DBU (1,8-diazabicycloundec-7-ene), DBN (1,5-diazabicyclo[4.3.0]non-5-ene), and MTBD (7-methyl-1,5,7-triazabicyclo[4.4.0]dec-5-ene).

17. The compound or pharmaceutically acceptable salts thereof according to claim 1, wherein the 5- to 7-membered nitrogen-containing saturated heterocyclyl is 1-pyrrolidinyl, 1-piperidyl, 4-morpholinyl, or 1-piperazinyl.

* * * * *